(12) United States Patent
Liu et al.

(10) Patent No.: US 11,709,156 B2
(45) Date of Patent: Jul. 25, 2023

(54) USE OF VAPOR DEPOSITION COATED FLOW PATHS FOR IMPROVED ANALYTICAL ANALYSIS

(71) Applicant: Waters Technologies Corporation, Milford, MA (US)

(72) Inventors: Xiaoxiao Liu, Milford, MA (US); Anna Boardman, Watertown, MA (US); Mathew H. DeLano, Needham, MA (US); Matthew A. Lauber, North Smithfield, RI (US)

(73) Assignee: Waters Technologies Corporation, Milford, MA (US)

( * ) Notice: Subject to any disclaimer, the term of this patent is extended or adjusted under 35 U.S.C. 154(b) by 165 days.

(21) Appl. No.: 16/746,031

(22) Filed: Jan. 17, 2020

(65) Prior Publication Data

US 2020/0217827 A1 Jul. 9, 2020

Related U.S. Application Data

(63) Continuation-in-part of application No. 16/133,089, filed on Sep. 17, 2018.

(60) Provisional application No. 62/559,895, filed on Sep. 18, 2017.

(51) Int. Cl.
| | |
|---|---|
| *G01N 30/56* | (2006.01) |
| *G01N 30/52* | (2006.01) |
| *B05D 1/00* | (2006.01) |
| *G01N 30/60* | (2006.01) |
| *G01N 33/74* | (2006.01) |
| *G01N 33/68* | (2006.01) |
| *G01N 33/92* | (2006.01) |

(52) U.S. Cl.
CPC .............. *G01N 30/56* (2013.01); *B05D 1/60* (2013.01); *G01N 30/52* (2013.01); *G01N 30/6052* (2013.01); *B05D 2202/00* (2013.01); *B05D 2203/35* (2013.01); *B05D 2518/10* (2013.01); *G01N 33/6803* (2013.01); *G01N 33/74* (2013.01); *G01N 33/92* (2013.01); *G01N 2030/567* (2013.01)

(58) Field of Classification Search
None
See application file for complete search history.

(56) References Cited

U.S. PATENT DOCUMENTS

| | | | |
|---|---|---|---|
| 2,801,186 | A | 7/1957 | Alexander et al. |
| 4,708,782 | A | 11/1987 | Andresen et al. |
| 4,711,820 | A | 12/1987 | Arkles et al. |
| 4,833,093 | A | 5/1989 | Malmqvist et al. |
| 4,945,282 | A | 7/1990 | Kawamura et al. |
| 4,999,162 | A | 3/1991 | Wells et al. |
| 5,002,794 | A | 3/1991 | Ratner et al. |
| 5,153,072 | A | 10/1992 | Ratner et al. |
| 5,470,463 | A * | 11/1995 | Girot .............. B01D 15/20 210/198.2 |
| 5,550,184 | A | 8/1996 | Halling |
| 5,595,813 | A | 1/1997 | Ogawa et al. |
| 5,643,436 | A | 7/1997 | Ogawa et al. |
| 5,688,855 | A | 11/1997 | Stoy et al. |

(Continued)

FOREIGN PATENT DOCUMENTS

| | | |
|---|---|---|
| AU | 2020244497 A1 | 10/2020 |
| CA | 2538124 C | 7/2010 |

(Continued)

OTHER PUBLICATIONS

HPLC Hardware. Möller Medical. (2007).
NanoCoatings Product Information. Möller Medical. (2010).
Shih et al. "Silanization of Stainless-Steel Frits for Use in Trace Metal Analysis by High Performance Liquid Chromatography." Talanta. 28(1981): 411-414.
Al-Hamarneh et al. "Synthesis and characterization of di(ethylene glycol) vinyl ether films deposited by atmospheric pressure corona discharge plasma." Surface Coatings Technol. 234(2013):33-41.
Beigbeder et al. "Marine Fouling Release Silicone/Carbon Nanotube Nanocomposite Coatings: On the Importance of the Nanotube Dispersion State." J. Nanosci. Nanotech, 10(2010): 2972-2978.
Biocyl™ X1, Dec. 20, 2018.
Carretier et al. "Design of PVDF/PEGMA-b-PS-b-PEGMA membranes by VIPS for improved biofouling mitigation." J. Membrane Sci. 510(2016):355-369.

(Continued)

*Primary Examiner* — Ryan B Huang
(74) *Attorney, Agent, or Firm* — Womble Bond Dickinson (US) LLP; Deborah Vernon

(57) ABSTRACT

A device for processing samples is disclosed. Interior surfaces of the device, which come in contact with fluids, define wetted surfaces. A portion of the wetted surfaces are coated with an alkylsilyl coating having the Formula I:

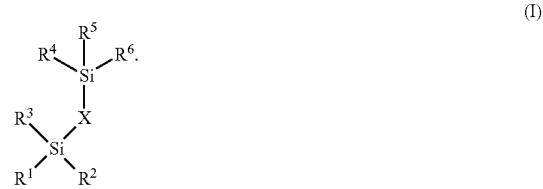

(I)

$R^1$, $R^2$, $R^3$, $R^4$, $R^5$, and $R^6$ are each independently selected from ($C_1$-$C_6$)alkoxy, —NH($C_1$-$C_6$)alkyl, —N(($C_1$-$C_6$)alkyl)$_2$, OH, $OR^4$, and halo. $R^4$ represents a point of attachment to the interior surfaces of the fluidic system. At least one of $R^1$, $R^2$, $R^3$, $R^4$, $R^5$, and $R^6$ is $OR^4$. X is ($C_1$-$C_{20}$)alkyl, —O[($CH_2$)$_2$O]$_{1-20}$—, —($C_1$-$C_{10}$)[NH(CO)NH($C_1$-$C_{10}$)]$_{1-20}$—, or —($C_1$-$C_{10}$)[alkylphenyl($C_1$-$C_{10}$)alkyl]$_{1-20}$—.

13 Claims, 35 Drawing Sheets

(56) References Cited

U.S. PATENT DOCUMENTS

| | | |
|---|---|---|
| 5,856,192 A | 1/1999 | Bloch |
| 5,876,753 A | 3/1999 | Timmons et al. |
| 5,909,314 A | 6/1999 | Oka et al. |
| 6,013,372 A | 1/2000 | Hayakawa et al. |
| 6,054,227 A | 4/2000 | Greenberg et al. |
| 6,074,981 A | 6/2000 | Tada et al. |
| 6,121,608 A | 9/2000 | Takada et al. |
| 6,194,346 B1 | 2/2001 | Tada et al. |
| 6,207,263 B1 | 3/2001 | Takematsu et al. |
| RE37,183 E | 5/2001 | Kawamura et al. |
| 6,265,026 B1 | 7/2001 | Wang |
| 6,306,506 B1 | 10/2001 | Timmons et al. |
| 6,329,024 B1 | 12/2001 | Timmons et al. |
| 6,329,209 B1 | 12/2001 | Wagner et al. |
| 6,337,129 B1 | 1/2002 | Watanabe et al. |
| 6,340,404 B1 | 1/2002 | Oka et al. |
| 6,383,642 B1 | 5/2002 | Le Bellac et al. |
| 6,440,565 B1 | 8/2002 | Kim et al. |
| 6,444,326 B1 | 9/2002 | Smith |
| 6,461,334 B1 | 10/2002 | Buch-Rasmussen et al. |
| 6,465,056 B1 | 10/2002 | Chabrecek et al. |
| 6,482,531 B1 | 11/2002 | Timmons et al. |
| 6,547,868 B1 | 4/2003 | Belmares et al. |
| 6,599,594 B1 | 7/2003 | Walther et al. |
| 6,660,338 B1 | 12/2003 | Hargreaves |
| 6,686,035 B2 | 2/2004 | Jiang et al. |
| 6,706,408 B2 | 3/2004 | Jelle |
| 6,743,516 B2 | 6/2004 | Murphy et al. |
| 6,763,437 B1 | 7/2004 | Nguyen et al. |
| 6,783,800 B2 | 8/2004 | Saito et al. |
| 6,844,028 B2 | 1/2005 | Mao et al. |
| 6,873,387 B2 | 3/2005 | Hokazono et al. |
| 6,905,772 B2 | 6/2005 | Shoup et al. |
| 6,916,541 B2 | 7/2005 | Pantano et al. |
| 6,991,826 B2 | 1/2006 | Pellerite et al. |
| 7,067,194 B2 | 6/2006 | Mao et al. |
| 7,138,186 B2 | 11/2006 | Luten, III |
| 7,250,214 B2 | 7/2007 | Walter et al. |
| 7,285,674 B2 | 10/2007 | Palma et al. |
| 7,294,365 B2 | 11/2007 | Hayakawa et al. |
| 7,351,477 B2 | 4/2008 | Yamaya et al. |
| 7,387,836 B2 | 6/2008 | Gianolio et al. |
| 7,413,774 B2 | 8/2008 | Kobrin et al. |
| 7,419,636 B2 | 9/2008 | Aker et al. |
| 7,419,699 B2 | 9/2008 | Kitada et al. |
| 7,431,969 B2 | 10/2008 | Gleason et al. |
| 7,553,514 B2 | 6/2009 | Fan et al. |
| 7,629,029 B2 | 12/2009 | Mao et al. |
| 7,638,167 B2 | 12/2009 | Kobrin et al. |
| 7,687,239 B2 | 3/2010 | Goldberg et al. |
| 7,695,775 B2 | 4/2010 | Kobrin et al. |
| 7,776,396 B2 | 8/2010 | Kobrin et al. |
| 7,785,649 B2 | 8/2010 | Jung et al. |
| 7,815,922 B2 | 10/2010 | Chaney et al. |
| 7,842,393 B2 | 11/2010 | Kuzuya et al. |
| 7,879,396 B2 | 2/2011 | Kobrin et al. |
| 7,901,744 B2 | 3/2011 | Denes et al. |
| 7,955,656 B2 | 6/2011 | Murayama et al. |
| 7,955,704 B2 | 6/2011 | Lowery et al. |
| 8,008,225 B2 | 8/2011 | Henze et al. |
| 8,025,915 B2 | 9/2011 | Haines et al. |
| 8,062,881 B2 | 11/2011 | Bookbinder et al. |
| 8,105,821 B2 | 1/2012 | McGall et al. |
| 8,147,954 B2 | 4/2012 | Lee et al. |
| 8,163,354 B2 | 4/2012 | Dang et al. |
| 8,178,168 B2 | 5/2012 | O'Neill et al. |
| 8,178,602 B2 | 5/2012 | Mao et al. |
| 8,323,166 B2 | 12/2012 | Haines et al. |
| 8,349,408 B2 | 1/2013 | Dulka et al. |
| 8,366,814 B2 | 2/2013 | Jones et al. |
| 8,404,621 B2 | 3/2013 | Ikeda et al. |
| 8,512,864 B2 | 8/2013 | Konno et al. |
| 8,557,748 B2 | 10/2013 | Ikeda et al. |
| 8,580,355 B2 | 11/2013 | Durandeau et al. |
| 8,652,588 B2 | 2/2014 | Teer et al. |
| 8,668,972 B2 | 3/2014 | Lewis et al. |
| 8,691,104 B2 | 4/2014 | Greer et al. |
| 8,709,588 B2 | 4/2014 | Cadet et al. |
| 8,741,158 B2 | 6/2014 | Aytug et al. |
| 8,778,278 B2 | 7/2014 | Xiong et al. |
| 8,784,565 B2 | 7/2014 | Hillabrand et al. |
| 8,795,787 B2 | 8/2014 | Jehle |
| 8,841,070 B2 | 9/2014 | Harnack et al. |
| 8,992,590 B2 | 3/2015 | Ott et al. |
| 8,993,479 B2 | 3/2015 | Zuilhof et al. |
| 9,034,660 B2 | 5/2015 | Boday et al. |
| 9,075,189 B2 | 7/2015 | West |
| 9,108,012 B2 | 8/2015 | Pryce Lewis et al. |
| 9,175,026 B2 | 11/2015 | Garrell et al. |
| 9,255,929 B2 | 2/2016 | Jiang et al. |
| 9,272,095 B2 | 3/2016 | Felts et al. |
| 9,308,520 B2 | 4/2016 | Ekeroth |
| 9,340,880 B2 | 5/2016 | Mattzela |
| 9,364,853 B2 | 6/2016 | Chen |
| 9,388,315 B2 | 7/2016 | Hoshino |
| 9,445,504 B2 | 9/2016 | Kang et al. |
| 9,475,225 B2 | 10/2016 | Giraud et al. |
| 9,523,004 B2 | 12/2016 | Hervieu et al. |
| 9,533,006 B2 | 1/2017 | Jiang et al. |
| 9,541,480 B2 | 1/2017 | Chang et al. |
| 9,556,360 B2 | 1/2017 | McGall et al. |
| 9,777,368 B2 | 10/2017 | Smith et al. |
| 9,915,001 B2 | 3/2018 | Yuan et al. |
| 9,925,521 B2 | 3/2018 | Wyndham et al. |
| 9,926,203 B2 | 3/2018 | Zhou |
| 9,975,143 B2 | 5/2018 | Smith et al. |
| 9,999,901 B2 | 6/2018 | Boscher et al. |
| 10,472,769 B2 | 11/2019 | Tuteja et al. |
| 10,813,609 B2 | 10/2020 | Goto et al. |
| 10,813,610 B2 | 10/2020 | Yoshida et al. |
| 10,814,253 B2 | 10/2020 | Lipkens et al. |
| 10,814,305 B2 | 10/2020 | Liao et al. |
| 10,814,319 B2 | 10/2020 | Dasgupta et al. |
| 10,814,320 B2 | 10/2020 | Le et al. |
| 10,814,740 B2 | 10/2020 | Wilhide |
| 10,815,247 B2 | 10/2020 | Flemming et al. |
| 10,815,269 B2 | 10/2020 | Maloisel et al. |
| 10,816,115 B2 | 10/2020 | Buerger et al. |
| 10,816,476 B2 | 10/2020 | Nunney et al. |
| 10,816,487 B2 | 10/2020 | Matney et al. |
| 10,816,515 B2 | 10/2020 | Hollnagel et al. |
| 10,816,518 B2 | 10/2020 | Jarrold et al. |
| 10,816,786 B2 | 10/2020 | Douglas-Hamilton et al. |
| 10,818,485 B2 | 10/2020 | Yamaguchi |
| 10,818,486 B2 | 10/2020 | Corr et al. |
| 10,828,665 B2 | 11/2020 | Stiff-Roberts et al. |
| 10,876,202 B2 | 12/2020 | Verbeck, IV et al. |
| 10,876,210 B1 | 12/2020 | Claussen et al. |
| 10,895,009 B2 | 1/2021 | Carr et al. |
| 10,912,714 B2 | 2/2021 | Weikart et al. |
| 2001/0021446 A1 | 9/2001 | Takematsu et al. |
| 2002/0016250 A1 | 2/2002 | Hayakawa et al. |
| 2002/0020053 A1 | 2/2002 | Fonash et al. |
| 2002/0026899 A1 | 3/2002 | McLaughlin et al. |
| 2002/0142621 A1 | 10/2002 | Wang |
| 2002/0172938 A1 | 11/2002 | Cuomo et al. |
| 2002/0195950 A1 | 12/2002 | Mikhael et al. |
| 2003/0059573 A1 | 3/2003 | Timmons et al. |
| 2003/0109062 A1 | 6/2003 | Inomata et al. |
| 2003/0113477 A1 | 6/2003 | Timmons et al. |
| 2003/0138645 A1 | 7/2003 | Gleason et al. |
| 2004/0261703 A1 | 12/2004 | Kobrin et al. |
| 2005/0118595 A1 | 6/2005 | Lahann |
| 2005/0164402 A1 | 7/2005 | Belisle et al. |
| 2005/0214803 A1 | 9/2005 | Wang |
| 2006/0073521 A1 | 4/2006 | Saito et al. |
| 2006/0110594 A1 | 5/2006 | Frutos et al. |
| 2006/0213441 A1 | 9/2006 | Kobrin et al. |
| 2006/0219598 A1 | 10/2006 | Cody et al. |
| 2006/0251795 A1 | 11/2006 | Kobrin et al. |
| 2007/0048747 A1 | 3/2007 | Leslie et al. |
| 2007/0065591 A1 | 3/2007 | Parbhu |
| 2007/0122308 A1 | 5/2007 | Ikeda et al. |
| 2007/0172666 A1 | 7/2007 | Denes et al. |

(56) References Cited

U.S. PATENT DOCUMENTS

| | | |
|---|---|---|
| 2008/0041105 A1 | 2/2008 | Hahn et al. |
| 2008/0075960 A1* | 3/2008 | Pocius ................. C09D 133/08 525/88 |
| 2008/0170230 A1 | 7/2008 | Gerion |
| 2008/0188010 A1 | 8/2008 | Saitoh et al. |
| 2008/0248589 A1 | 10/2008 | Belisle et al. |
| 2008/0312356 A1 | 12/2008 | Kobrin et al. |
| 2009/0020712 A1 | 1/2009 | Matsumoto |
| 2009/0081371 A1 | 3/2009 | Minami et al. |
| 2009/0162571 A1 | 6/2009 | Haines et al. |
| 2009/0176084 A1 | 7/2009 | Yoshihara et al. |
| 2009/0206034 A1* | 8/2009 | Nakajima ............... B01J 20/328 210/635 |
| 2009/0286435 A1 | 11/2009 | Badyal et al. |
| 2009/0318609 A1 | 12/2009 | Badyal et al. |
| 2010/0080903 A1 | 4/2010 | Tamitsuji et al. |
| 2010/0178512 A1 | 7/2010 | Giesenberg et al. |
| 2010/0196724 A1 | 8/2010 | Yamasaki et al. |
| 2010/0200207 A1 | 8/2010 | Fukuda et al. |
| 2010/0203646 A1 | 8/2010 | Larsen et al. |
| 2010/0330278 A1 | 12/2010 | Choi et al. |
| 2011/0000658 A1 | 1/2011 | Tanaka et al. |
| 2011/0062047 A1 | 3/2011 | Haines et al. |
| 2011/0120213 A1 | 5/2011 | Hirayama et al. |
| 2011/0120940 A1 | 5/2011 | Allen et al. |
| 2011/0189493 A1 | 8/2011 | Ott et al. |
| 2012/0069295 A1 | 3/2012 | Fukagawa et al. |
| 2012/0123345 A1 | 5/2012 | Felts et al. |
| 2012/0178848 A1 | 7/2012 | Adkinson et al. |
| 2012/0219697 A1 | 8/2012 | Chen |
| 2012/0219727 A1 | 8/2012 | Gandhiraman et al. |
| 2012/0251797 A1 | 10/2012 | Smith et al. |
| 2012/0252709 A1 | 10/2012 | Felts et al. |
| 2012/0288717 A1 | 11/2012 | Mao et al. |
| 2013/0004780 A1 | 1/2013 | Hervieu et al. |
| 2013/0025503 A1 | 1/2013 | Park et al. |
| 2013/0029138 A1 | 1/2013 | Benard et al. |
| 2013/0136937 A1 | 5/2013 | Fujii et al. |
| 2013/0157062 A1 | 6/2013 | Kihara et al. |
| 2013/0244025 A1 | 9/2013 | Smith et al. |
| 2013/0266762 A1 | 10/2013 | Mayers et al. |
| 2013/0337226 A1 | 12/2013 | Curran et al. |
| 2014/0004022 A1 | 1/2014 | Sagona et al. |
| 2014/0065368 A1 | 3/2014 | Aytug et al. |
| 2014/0147631 A1 | 5/2014 | Yang et al. |
| 2014/0154399 A1 | 6/2014 | Weikart et al. |
| 2014/0187666 A1 | 7/2014 | Aizenberg et al. |
| 2014/0202355 A1 | 7/2014 | Hoshino |
| 2014/0287240 A1 | 9/2014 | Murotani et al. |
| 2014/0299538 A1 | 10/2014 | Gleason et al. |
| 2014/0318748 A1 | 10/2014 | Svensson et al. |
| 2014/0323981 A1 | 10/2014 | Giraud et al. |
| 2014/0342954 A1 | 11/2014 | Ingber et al. |
| 2014/0357091 A1 | 12/2014 | Mattzela |
| 2014/0370300 A1 | 12/2014 | Smith |
| 2015/0021339 A1 | 1/2015 | Felts et al. |
| 2015/0024152 A1 | 1/2015 | Carr et al. |
| 2015/0030885 A1 | 1/2015 | Smith |
| 2015/0064376 A1 | 3/2015 | Smith et al. |
| 2015/0064451 A1 | 3/2015 | Kalaga et al. |
| 2015/0098084 A1 | 4/2015 | Felts et al. |
| 2015/0118502 A1 | 4/2015 | Mitsuhashi et al. |
| 2015/0118504 A1 | 4/2015 | Ohshita et al. |
| 2015/0122365 A1 | 5/2015 | Carr et al. |
| 2015/0152124 A1 | 6/2015 | Mori et al. |
| 2015/0175814 A1 | 6/2015 | Aizenberg et al. |
| 2015/0209846 A1 | 7/2015 | Aizenberg et al. |
| 2015/0210951 A1 | 7/2015 | Aizenberg et al. |
| 2015/0232806 A1 | 8/2015 | Jung et al. |
| 2015/0239773 A1 | 8/2015 | Aytug |
| 2015/0247051 A1 | 9/2015 | Ha et al. |
| 2015/0273522 A1 | 10/2015 | Boscher et al. |
| 2015/0283307 A1* | 10/2015 | Smith ...................... C23C 16/30 428/34.1 |
| 2015/0298165 A1 | 10/2015 | Smith |
| 2015/0307525 A1 | 10/2015 | Higano et al. |
| 2015/0307719 A1 | 10/2015 | Mitsuhashi et al. |
| 2015/0309216 A1 | 10/2015 | Fournand |
| 2015/0322272 A1 | 11/2015 | Pokroy et al. |
| 2015/0329725 A1 | 11/2015 | Liu |
| 2016/0002488 A1 | 1/2016 | Takao et al. |
| 2016/0002489 A1 | 1/2016 | Gleason et al. |
| 2016/0038972 A1 | 2/2016 | Lu |
| 2016/0040039 A1 | 2/2016 | Yamane et al. |
| 2016/0059260 A1 | 3/2016 | Smith et al. |
| 2016/0074862 A1 | 3/2016 | Breaux et al. |
| 2016/0168021 A1 | 6/2016 | Goh et al. |
| 2016/0200941 A1 | 7/2016 | Liu et al. |
| 2016/0231594 A1 | 8/2016 | Ang et al. |
| 2016/0243308 A1 | 8/2016 | Giraud et al. |
| 2016/0251261 A1 | 9/2016 | Bureau |
| 2016/0289824 A1 | 10/2016 | Mattzela et al. |
| 2016/0302723 A1 | 10/2016 | Chen |
| 2016/0340544 A1 | 11/2016 | Katsukawa et al. |
| 2017/0001956 A1 | 1/2017 | Chau et al. |
| 2017/0044315 A1 | 2/2017 | Mitsuhashi et al. |
| 2017/0173223 A1 | 6/2017 | Delaney, Jr. et al. |
| 2018/0049644 A1 | 2/2018 | Themelis |
| 2018/0357402 A1 | 12/2018 | Omata et al. |
| 2019/0032201 A1 | 1/2019 | Smith et al. |
| 2019/0077966 A1 | 3/2019 | Koguchi et al. |
| 2019/0390329 A1 | 12/2019 | Carr et al. |
| 2020/0024155 A1 | 1/2020 | Kano et al. |
| 2020/0024156 A1 | 1/2020 | Kano et al. |
| 2020/0024157 A1 | 1/2020 | Kano et al. |
| 2020/0062615 A1 | 2/2020 | Rajagopalan et al. |
| 2020/0189938 A1 | 6/2020 | Kano et al. |
| 2020/0215457 A1 | 7/2020 | DeLano et al. |
| 2020/0239641 A1 | 7/2020 | Kawakami et al. |
| 2020/0328073 A1 | 10/2020 | Peterson et al. |
| 2020/0332801 A1 | 10/2020 | Kimura |
| 2020/0333265 A1 | 10/2020 | Doki et al. |
| 2020/0333369 A1 | 10/2020 | Toyoda et al. |
| 2020/0334792 A1 | 10/2020 | Themelis |
| 2020/0335902 A1 | 10/2020 | Tanaka |
| 2020/0337659 A1 | 10/2020 | Sano et al. |
| 2020/0338528 A1 | 10/2020 | Dong et al. |
| 2020/0339322 A1 | 10/2020 | Christensen et al. |
| 2020/0339665 A1 | 10/2020 | Bruhlmann et al. |
| 2020/0339931 A1 | 10/2020 | Bremer et al. |
| 2020/0339977 A1 | 10/2020 | Lebofsky et al. |
| 2020/0339980 A1 | 10/2020 | Dellinger et al. |
| 2020/0340047 A1 | 10/2020 | Mollerup |
| 2020/0340468 A1 | 10/2020 | Kuntz et al. |
| 2020/0340889 A1 | 10/2020 | Mlcak et al. |
| 2020/0340890 A1 | 10/2020 | Mlcak |
| 2020/0340910 A1 | 10/2020 | Handique |
| 2020/0340946 A1 | 10/2020 | Bateman et al. |
| 2020/0340949 A1 | 10/2020 | Mlcak et al. |
| 2020/0340950 A1 | 10/2020 | Mlcak et al. |
| 2020/0340956 A1 | 10/2020 | Ortmann et al. |
| 2020/0340959 A1 | 10/2020 | Schultz et al. |
| 2020/0340961 A1 | 10/2020 | Kunimura |
| 2020/0340982 A1 | 10/2020 | Levin et al. |
| 2020/0341253 A1 | 10/2020 | Foelling |
| 2020/0341255 A1 | 10/2020 | Chan |
| 2020/0341259 A1 | 10/2020 | Chan et al. |
| 2020/0341278 A1 | 10/2020 | Tanaka |
| 2020/0341378 A1 | 10/2020 | Wolterink et al. |
| 2020/0342326 A1 | 10/2020 | Rahnama Moghaddam |
| 2020/0342672 A1 | 10/2020 | Schmelig et al. |
| 2020/0343082 A1 | 10/2020 | Richardson et al. |
| 2020/0365237 A1 | 11/2020 | Madden et al. |
| 2020/0375846 A1 | 12/2020 | Chang et al. |
| 2021/0009883 A1 | 1/2021 | Tuteja et al. |
| 2021/0032157 A1 | 2/2021 | Czihal et al. |
| 2021/0061049 A1 | 3/2021 | Lekon et al. |
| 2021/0098233 A1 | 4/2021 | Kapoor et al. |
| 2021/0101176 A1 | 4/2021 | Baltazar et al. |

FOREIGN PATENT DOCUMENTS

| | | |
|---|---|---|
| CA | 2881275 C | 10/2020 |
| CA | 2855353 C | 1/2021 |

(56) References Cited

FOREIGN PATENT DOCUMENTS

| | | |
|---|---|---|
| CN | 104327663 A | 2/2015 |
| CN | 109225113 A | 1/2019 |
| CN | 109608680 A | 4/2019 |
| CN | 111471977 A | 7/2020 |
| CN | 111560172 A | 8/2020 |
| CN | 111848755 A | 10/2020 |
| CN | 111855826 A | 10/2020 |
| CN | 111855827 A | 10/2020 |
| CN | 111863585 A | 10/2020 |
| CN | 111944153 A | 11/2020 |
| CN | 112011055 A | 12/2020 |
| CN | 112264272 A | 1/2021 |
| EP | 1816155 B1 | 6/2011 |
| EP | 2608219 B1 | 3/2015 |
| EP | 2915833 A1 | 9/2015 |
| EP | 3573646 A1 | 12/2019 |
| EP | 3633366 A1 | 4/2020 |
| EP | 2403621 B1 | 10/2020 |
| EP | 2798664 B1 | 10/2020 |
| EP | 2834837 B1 | 10/2020 |
| EP | 2900819 B1 | 10/2020 |
| EP | 3006980 B1 | 10/2020 |
| EP | 3060325 B1 | 10/2020 |
| EP | 3131657 B1 | 10/2020 |
| EP | 3139150 B1 | 10/2020 |
| EP | 3169232 B1 | 10/2020 |
| EP | 3169424 B1 | 10/2020 |
| EP | 3273674 B1 | 10/2020 |
| EP | 3344317 B1 | 10/2020 |
| EP | 3399074 B1 | 10/2020 |
| EP | 3545085 A4 | 10/2020 |
| EP | 3727152 A1 | 10/2020 |
| EP | 3727637 A1 | 10/2020 |
| EP | 3727679 A1 | 10/2020 |
| EP | 3727690 A1 | 10/2020 |
| EP | 3728046 A1 | 10/2020 |
| EP | 3728581 A1 | 10/2020 |
| EP | 3728621 A2 | 10/2020 |
| EP | 3728633 A1 | 10/2020 |
| EP | 3729055 A1 | 10/2020 |
| EP | 3729071 A1 | 10/2020 |
| EP | 3729077 A1 | 10/2020 |
| EP | 3729083 A1 | 10/2020 |
| EP | 3729162 A1 | 10/2020 |
| EP | 3729487 A1 | 10/2020 |
| EP | 3729488 A2 | 10/2020 |
| EP | 3730119 A1 | 10/2020 |
| EP | 3730324 A1 | 10/2020 |
| EP | 3730406 A1 | 10/2020 |
| EP | 3730538 A1 | 10/2020 |
| EP | 3730599 A1 | 10/2020 |
| EP | 3730922 A1 | 10/2020 |
| EP | 3730923 A1 | 10/2020 |
| EP | 3730927 A1 | 10/2020 |
| EP | 3731393 A1 | 10/2020 |
| EP | 3749719 A1 | 12/2020 |
| EP | 3788181 A1 | 3/2021 |
| FR | 3095337 A1 | 10/2020 |
| GB | 2108403 A | 5/1983 |
| GB | 2429428 A | 2/2007 |
| GB | 2481687 A | 1/2012 |
| GB | 2490243 A | 10/2012 |
| GB | 2501803 A | 11/2013 |
| GB | 2531126 A | 4/2016 |
| GB | 2549248 A | 10/2017 |
| GB | 2534477 B | 10/2020 |
| GB | 2574723 B | 10/2020 |
| IL | 174122 A | 9/2011 |
| IL | 239213 A | 3/2020 |
| IL | 253518 A | 6/2020 |
| IL | 262854 A | 6/2020 |
| JP | 2012232870 A | 11/2012 |
| JP | 2020507460 A | 3/2020 |
| JP | 2020507462 A | 3/2020 |
| JP | 2020507466 A | 3/2020 |
| JP | 2020510522 A | 4/2020 |
| JP | 6770727 B2 | 10/2020 |
| JP | 6771390 B2 | 10/2020 |
| JP | 6771801 B2 | 10/2020 |
| JP | 6772721 B2 | 10/2020 |
| JP | 6772764 B2 | 10/2020 |
| JP | 6772953 B2 | 10/2020 |
| JP | 6773138 B2 | 10/2020 |
| JP | 6773236 B2 | 10/2020 |
| JP | 2020169857 A | 10/2020 |
| JP | 2020171429 A | 10/2020 |
| JP | 2020171482 A | 10/2020 |
| JP | 2020171483 A | 10/2020 |
| JP | 2020171484 A | 10/2020 |
| JP | 2020171882 A | 10/2020 |
| JP | 2020172518 A | 10/2020 |
| JP | 2020172703 A | 10/2020 |
| JP | 2020173192 A | 10/2020 |
| JP | 2020173427 A | 10/2020 |
| JP | 2020176195 A | 10/2020 |
| JP | 2020177669 A | 10/2020 |
| JP | 2020530329 A | 10/2020 |
| JP | 2020530909 A | 10/2020 |
| JP | 2020536764 A | 12/2020 |
| KR | 960007179 B1 | 5/1996 |
| KR | 20000019936 A | 4/2000 |
| KR | 20060130959 A | 12/2006 |
| KR | 20080071942 A | 8/2008 |
| KR | 20120007817 A | 1/2012 |
| KR | 20130020869 A | 3/2013 |
| KR | 20140082838 A | 7/2014 |
| KR | 101711786 B1 | 3/2017 |
| KR | 20170021957 A | 3/2017 |
| KR | 101742683 B1 | 6/2017 |
| KR | 20180008427 A | 1/2018 |
| KR | 20200139842 A | 12/2020 |
| KR | 20210008523 A | 1/2021 |
| KR | 102218186 B1 | 2/2021 |
| KR | 20210013582 A | 2/2021 |
| TW | 202031738 A | 9/2020 |
| TW | 202039644 A | 11/2020 |
| WO | 1998017407 A1 | 4/1998 |
| WO | 1999040038 A1 | 8/1999 |
| WO | 199951773 A1 | 10/1999 |
| WO | 200032044 A1 | 6/2000 |
| WO | 200168240 A2 | 9/2001 |
| WO | 2002085250 A2 | 10/2002 |
| WO | 2002085330 A1 | 10/2002 |
| WO | 2006015982 A2 | 2/2006 |
| WO | 2007081387 A1 | 7/2007 |
| WO | 2007117191 A1 | 10/2007 |
| WO | 2007117213 A1 | 10/2007 |
| WO | 2007117214 A1 | 10/2007 |
| WO | 2009007150 A2 | 1/2009 |
| WO | 2010009311 A1 | 1/2010 |
| WO | 2010135660 A2 | 11/2010 |
| WO | 2012170549 A1 | 12/2012 |
| WO | 2014104495 A1 | 7/2014 |
| WO | 2014104573 A1 | 7/2014 |
| WO | 2014164928 A1 | 10/2014 |
| WO | 2015050449 A2 | 4/2015 |
| WO | 2015054652 A2 | 4/2015 |
| WO | 2015134488 A1 | 9/2015 |
| WO | 2016100923 A1 | 6/2016 |
| WO | 2016114850 A1 | 7/2016 |
| WO | 2016125272 A1 | 8/2016 |
| WO | 2016160702 A1 | 10/2016 |
| WO | 2016166816 A1 | 10/2016 |
| WO | 2017040623 A1 | 3/2017 |
| WO | 2017053891 A1 | 3/2017 |
| WO | 2017060991 A1 | 4/2017 |
| WO | 2017072893 A1 | 5/2017 |
| WO | 2017087032 A1 | 5/2017 |
| WO | 2017098758 A1 | 6/2017 |
| WO | 2017143246 A1 | 8/2017 |
| WO | 2017171546 A1 | 10/2017 |
| WO | 2017210223 A1 | 12/2017 |
| WO | 2018072862 A1 | 4/2018 |
| WO | 2018146318 A1 | 8/2018 |

(56) References Cited

FOREIGN PATENT DOCUMENTS

| | | | |
|---|---|---|---|
| WO | 2018202935 | A1 | 11/2018 |
| WO | 2019053693 | A1 | 3/2019 |
| WO | 2019063482 | A1 | 4/2019 |
| WO | 2019101980 | A1 | 5/2019 |
| WO | 2019116619 | A1 | 6/2019 |
| WO | 2019122100 | A1 | 6/2019 |
| WO | 2019126130 | A1 | 6/2019 |
| WO | 2019130536 | A1 | 7/2019 |
| WO | 2019138705 | A1 | 7/2019 |
| WO | 2019150573 | A1 | 8/2019 |
| WO | 2019152724 | A1 | 8/2019 |
| WO | 2019154758 | A1 | 8/2019 |
| WO | 2019155543 | A1 | 8/2019 |
| WO | 2019155545 | A1 | 8/2019 |
| WO | 2019165297 | A1 | 8/2019 |
| WO | 2019168989 | A1 | 9/2019 |
| WO | 2019171085 | A1 | 9/2019 |
| WO | 2019175441 | A1 | 9/2019 |
| WO | 2019176081 | A1 | 9/2019 |
| WO | 2019180045 | A1 | 9/2019 |
| WO | 2019185607 | A1 | 10/2019 |
| WO | 2019186999 | A1 | 10/2019 |
| WO | 2019191269 | A1 | 10/2019 |
| WO | 2019191587 | A2 | 10/2019 |
| WO | 2019193558 | A1 | 10/2019 |
| WO | 2019198280 | A1 | 10/2019 |
| WO | 2019200306 | A1 | 10/2019 |
| WO | 2019212799 | A1 | 11/2019 |
| WO | 2019218088 | A1 | 11/2019 |
| WO | 2019224201 | A1 | 11/2019 |
| WO | 2019224540 | A1 | 11/2019 |
| WO | 2019229171 | A1 | 12/2019 |
| WO | 2019238469 | A1 | 12/2019 |
| WO | 2019241394 | A1 | 12/2019 |
| WO | 2020068174 | A2 | 4/2020 |
| WO | 2020095566 | A1 | 5/2020 |
| WO | 2020104521 | A2 | 5/2020 |
| WO | 2020213061 | A1 | 10/2020 |
| WO | 2020213101 | A1 | 10/2020 |
| WO | 2020213209 | A1 | 10/2020 |
| WO | 2020216966 | A1 | 10/2020 |
| WO | 2020219451 | A1 | 10/2020 |
| WO | 2020219605 | A1 | 10/2020 |
| WO | 2020219659 | A1 | 10/2020 |
| WO | 2020219667 | A1 | 10/2020 |
| WO | 2020219671 | A1 | 10/2020 |
| WO | 2020219784 | A1 | 10/2020 |
| WO | 2020219869 | A1 | 10/2020 |
| WO | 2021019220 | A1 | 2/2021 |
| WO | 2021061049 | A1 | 4/2021 |
| WO | 2021072245 | A1 | 4/2021 |

OTHER PUBLICATIONS

Dursan® Coating for Improved, Metal-Free Liquid Chromatography. Dec. 20, 2018.
Dursan® Data Sheet 2018.
Hsieh et al. "Effective Enhancement of Fluorescence Detection Efficiency in Protein Microarray assays: Application of a Highly Fluorinated Organosilane as the Blocking Agent on the Background Surface by a Facile Vapor-Phase Deposition Process." Anal. Chem. 81(2009): 7908-7916.
Kaliaraj et al. "Bio-inspired YSZ coated titanium by EB-PVD for biomedical applications." Surface and Coatings Technol. 307(2016): 227-235.
Lauber et al. "Rapid Preparation of Released N-Glycans for HILIC Analysis Using a Labeling Reagent that Facilitates Sensitive Fluorescence and ESI-MS Detection." Anal Chem. 87.10(2015): 5401-9.
Lecloux et al. "The safe use of carbon nanotubes in coating applications." OECD Conference on Benefits of nanomaterials. Paris, Jul. 15-17, 2009.
Rosmaninho et al. "Modified stainless steel surfaces targeted to reduce fouling—Evaluation of fouling by milk components." J. Food Engineering. 80(2007): 1176-1187.
Sun et al. "Vapor-based Grafting of Crosslinked Poly(N-vinyl pyrrolidone) Coatings with Tuned Hydrophilicity and Anti-Biofouling Properties." J. Mater. Chem. B. 4(2016): 2669-2678.
Vaidya et al. "Protein-resistant properties of a chemical vapor deposited alkyl-functional carboxysilane coating characterized using quartz crystal microbalance." Appl. Surface Sci. 364(2016): 896-908.
Velox Plus, Dec. 20, 2018.
Xue et al. "Surface-modified anodic aluminum oxide membrane with hydroxyethyl celluloses as a matrix for bilirubin removal." J. Chromatog. B. 912(2013):1-7.
Yang et al. "Synergistic Prevention of Biofouling in Seawater Desalination by Zwitterionic Surfaces and Low-Level Chlorination." Adv. Mater. 26(2014): 1711-1718.
Cheong. "Fritting techniques in chromatography." J. Sep. Sci. 37(2014): 603-617.
Rahimi et al. "Application of copolymer coated frits for solid-phase extraction of poly cyclic aromatic hydrocarbons in water samples." Anal. Chim. Acta. 836(2014): 45-52.
International Search Report and Written Opinion issued in International Application No. PCT/IB2021/059534 dated Mar. 10, 2022.
Kanavarioti et al. "HPLC methods for purity evaluation of man-made single-stranded RNAs." Nature. 9(2019): 1019.
Wyndham et al. "Characterization and Evaluation of C18 HPLC Stationary Phases Based on Ethyl-Bridged Hybrid Organic/Inorganic Particles." Anal. Chem. 75.24(2003): 6781-6788.

* cited by examiner

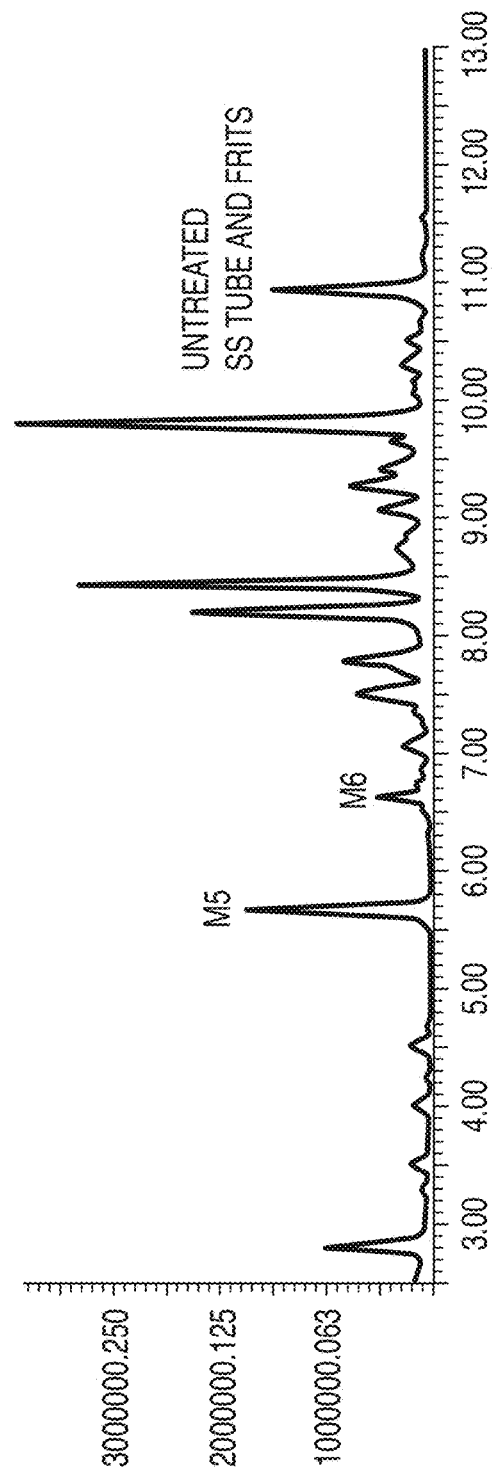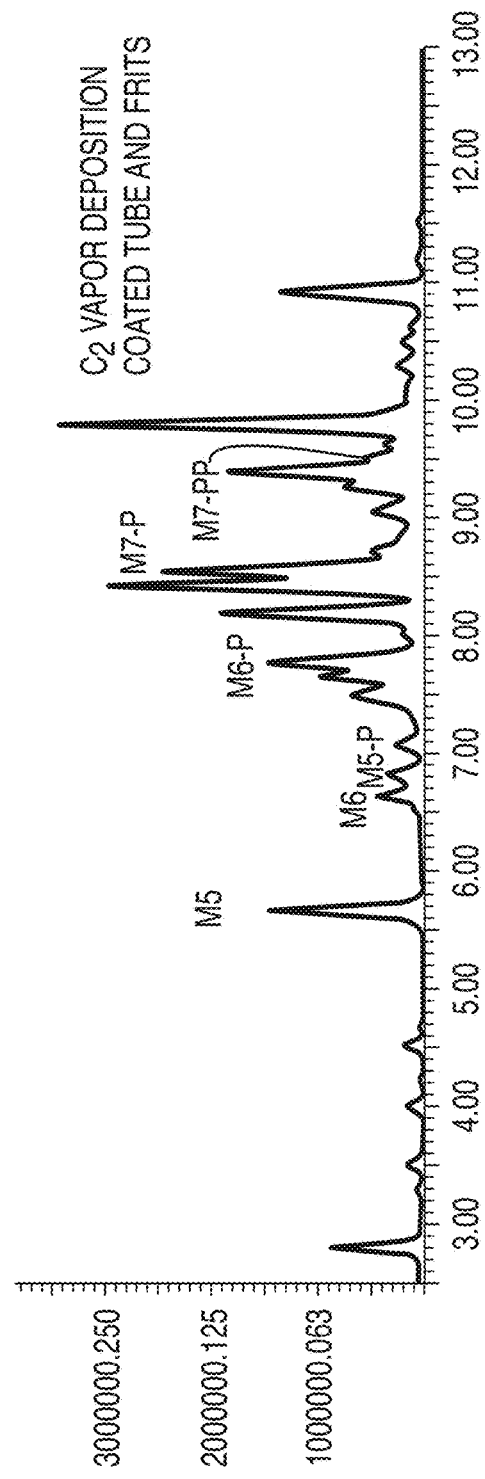
FIG. 4A
FIG. 4B

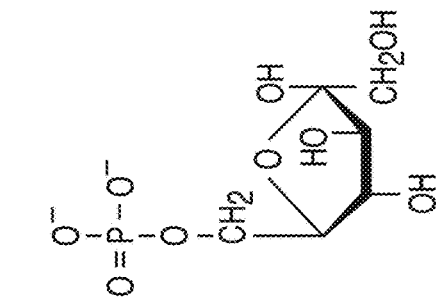
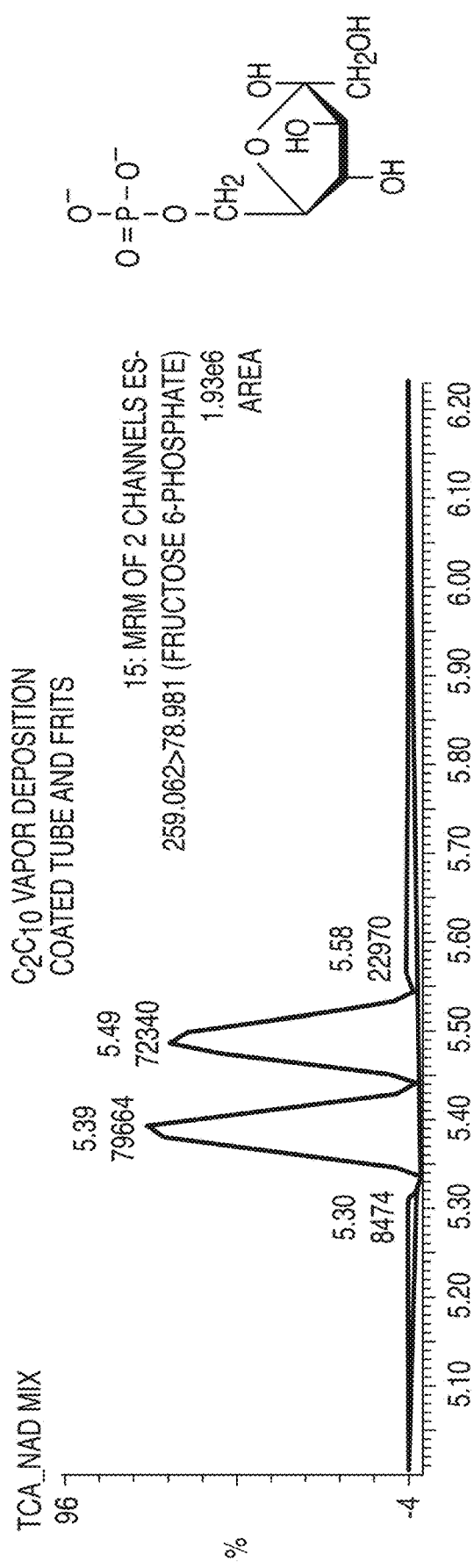
FIG. 9A
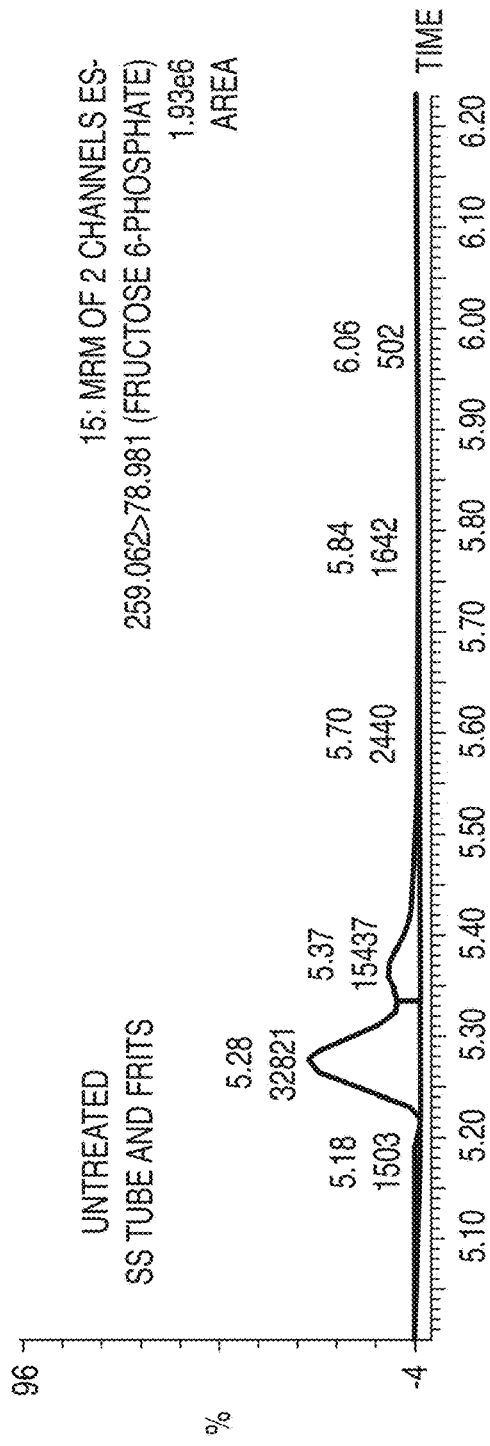
FIG. 9B

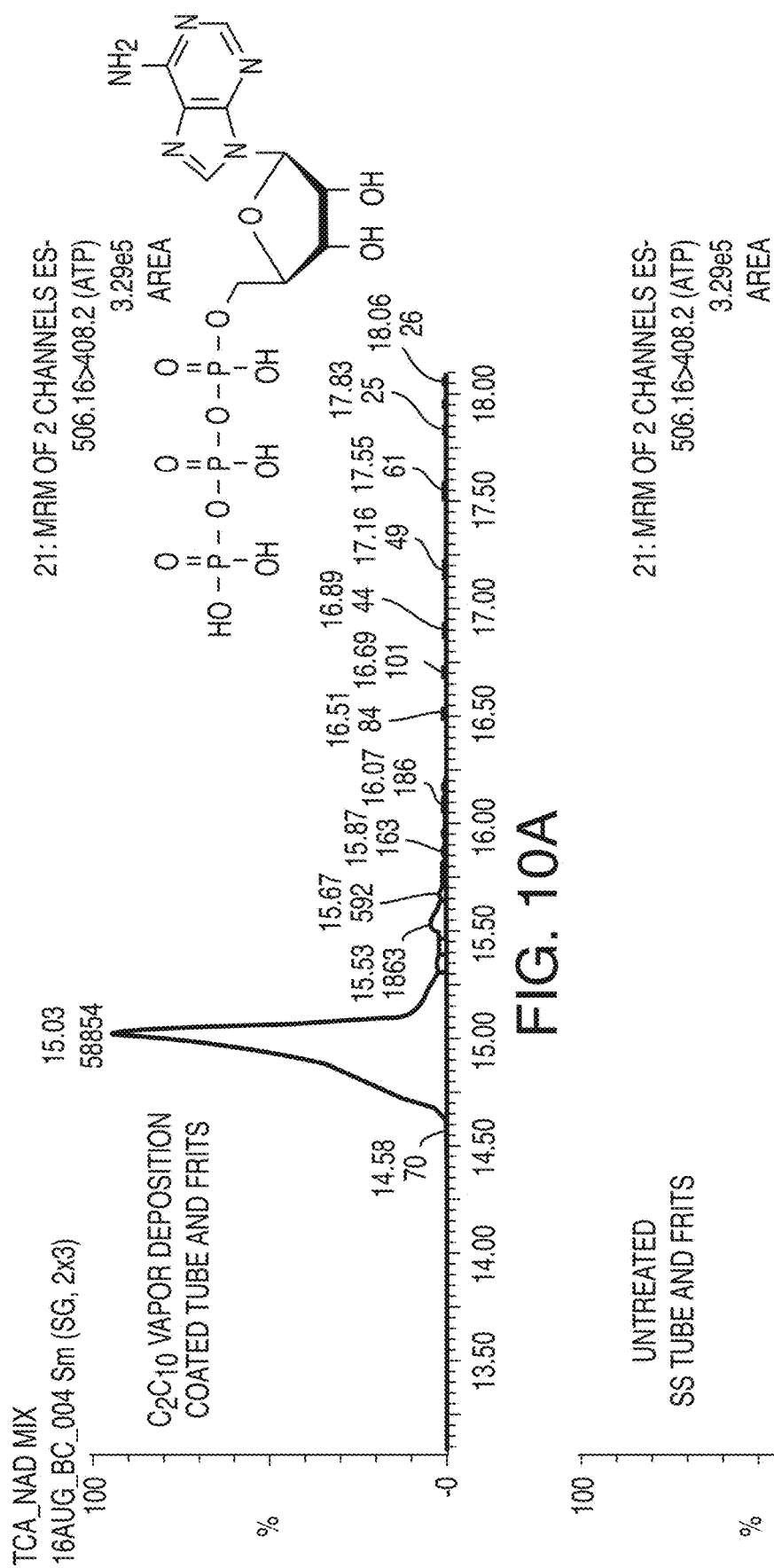

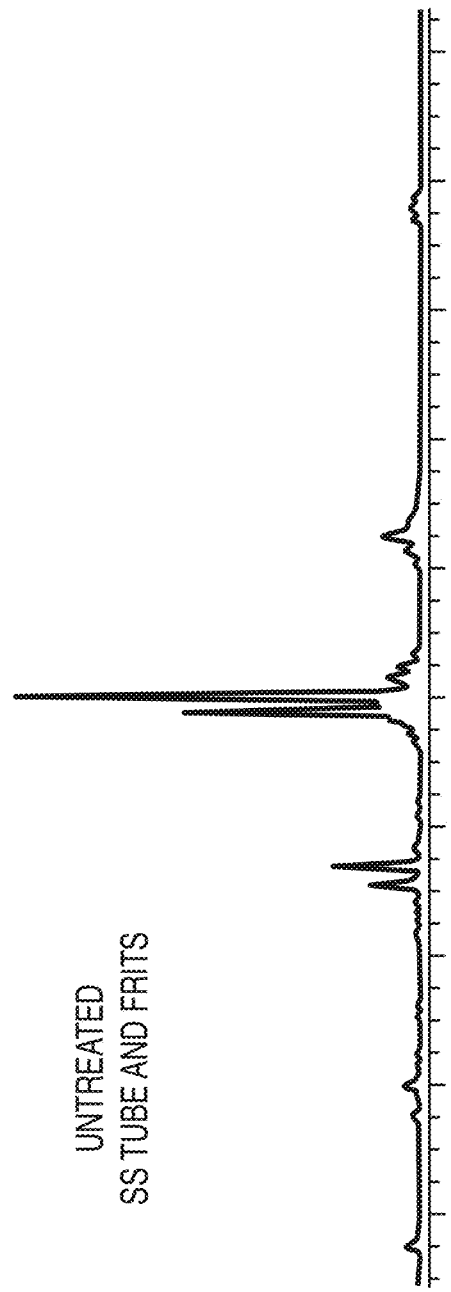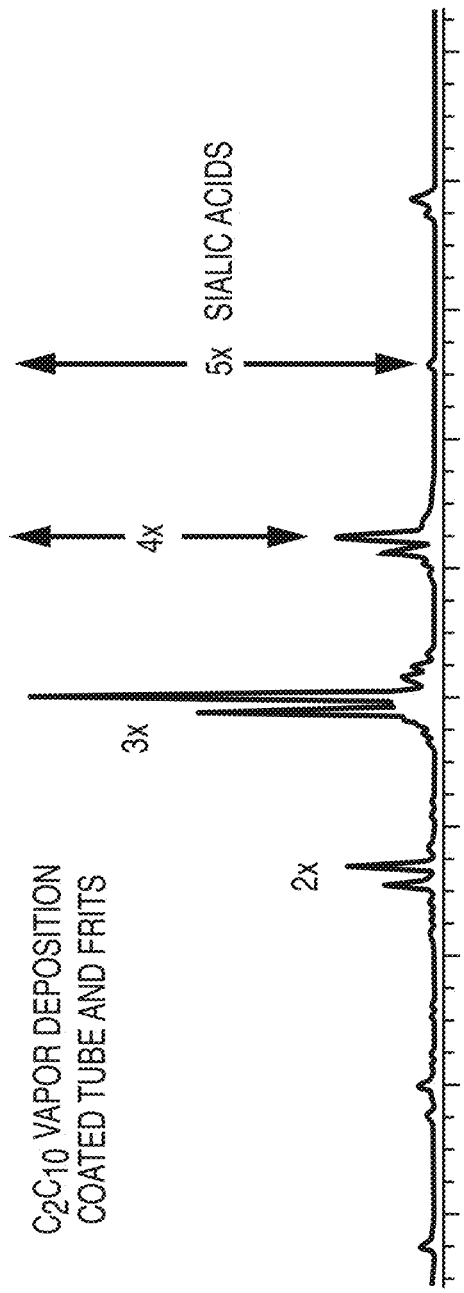

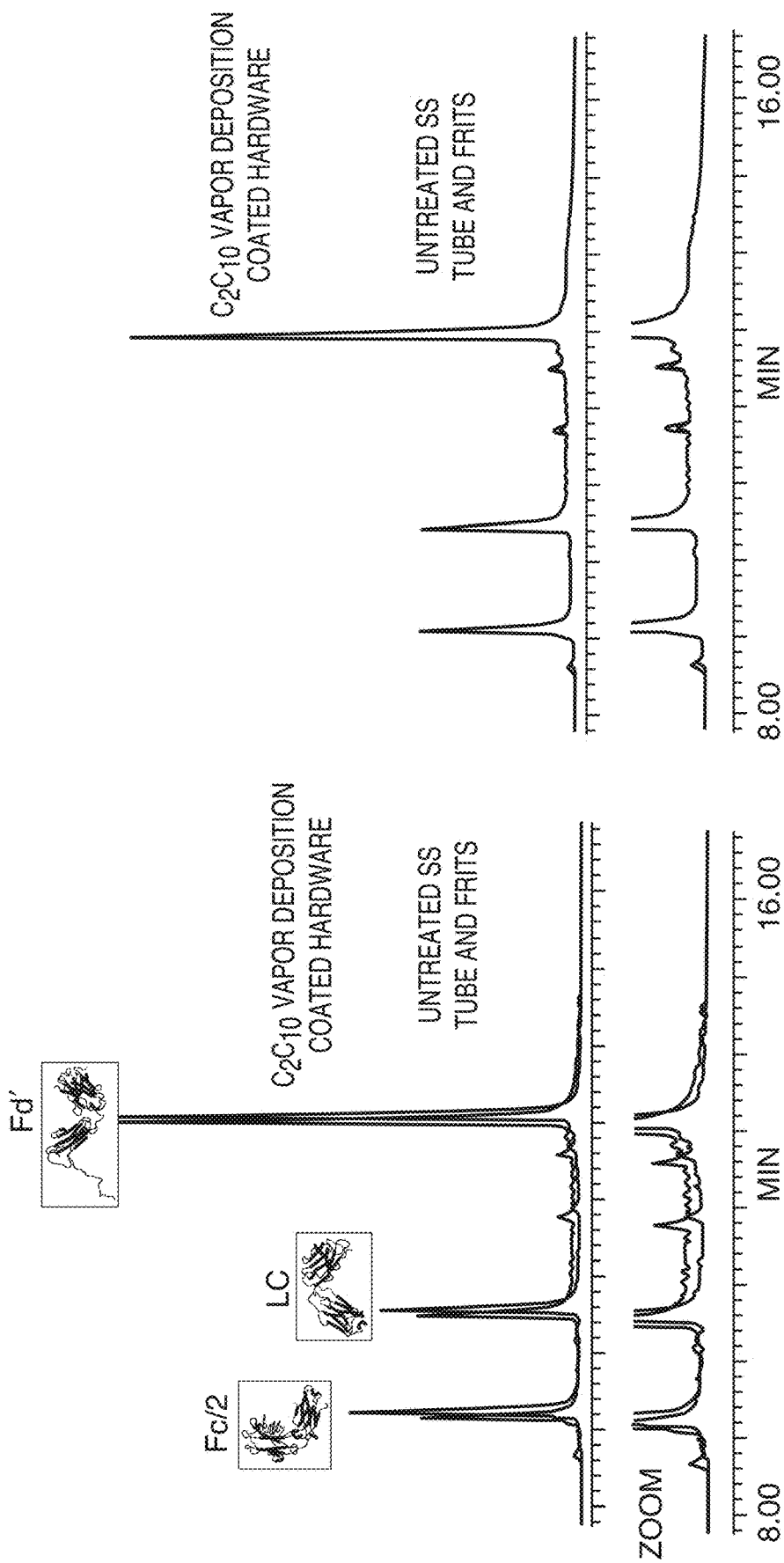

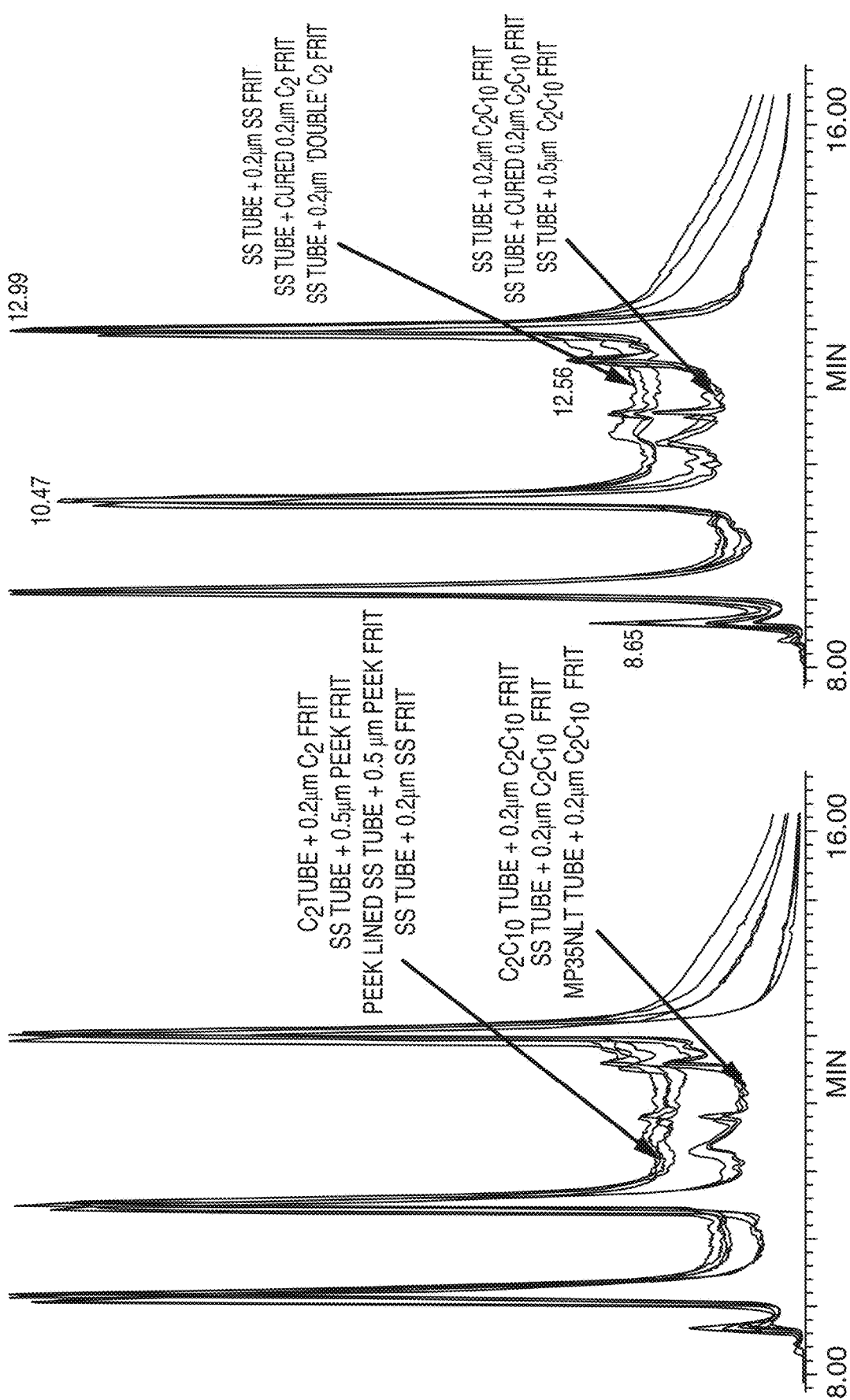

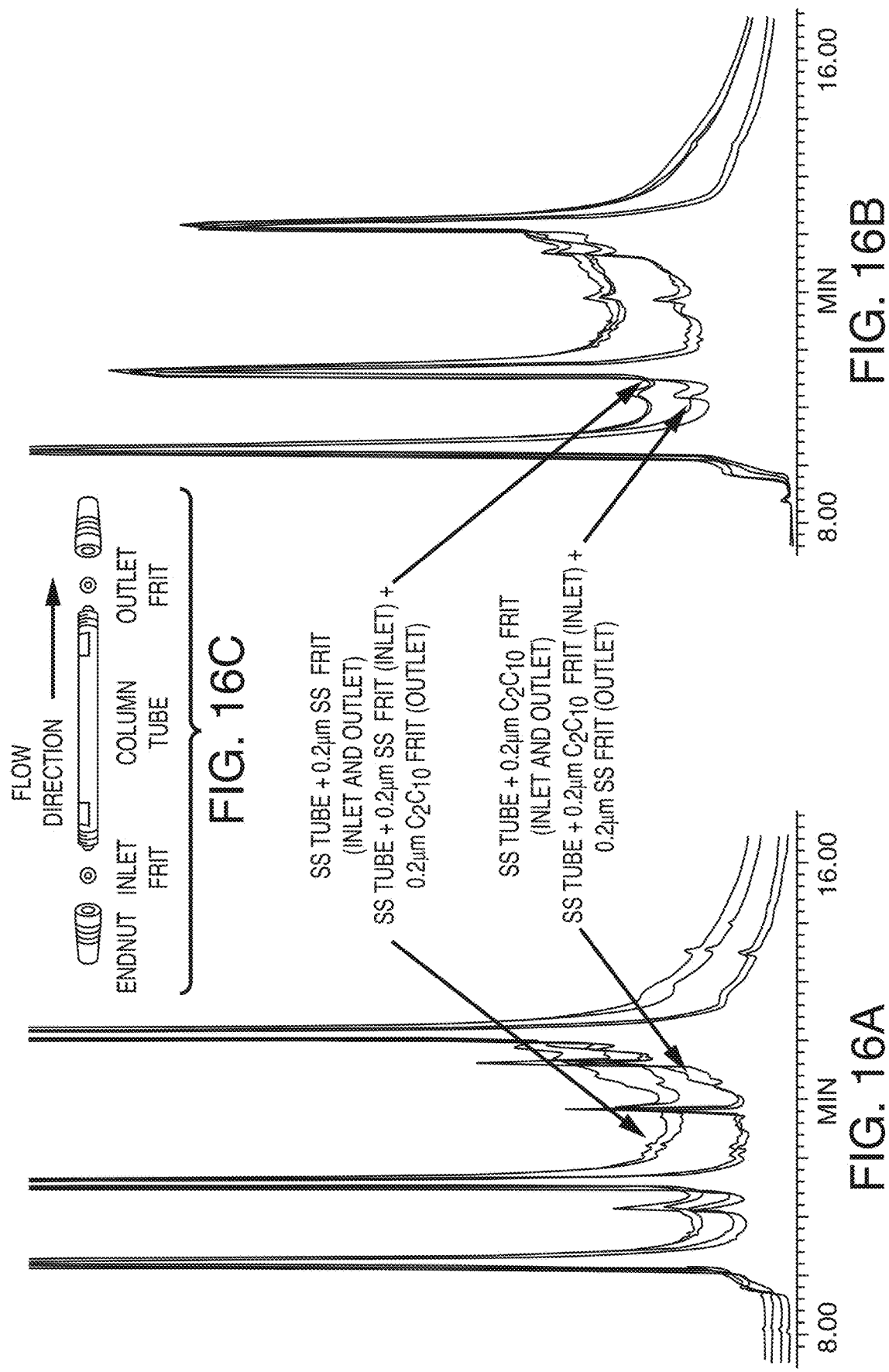

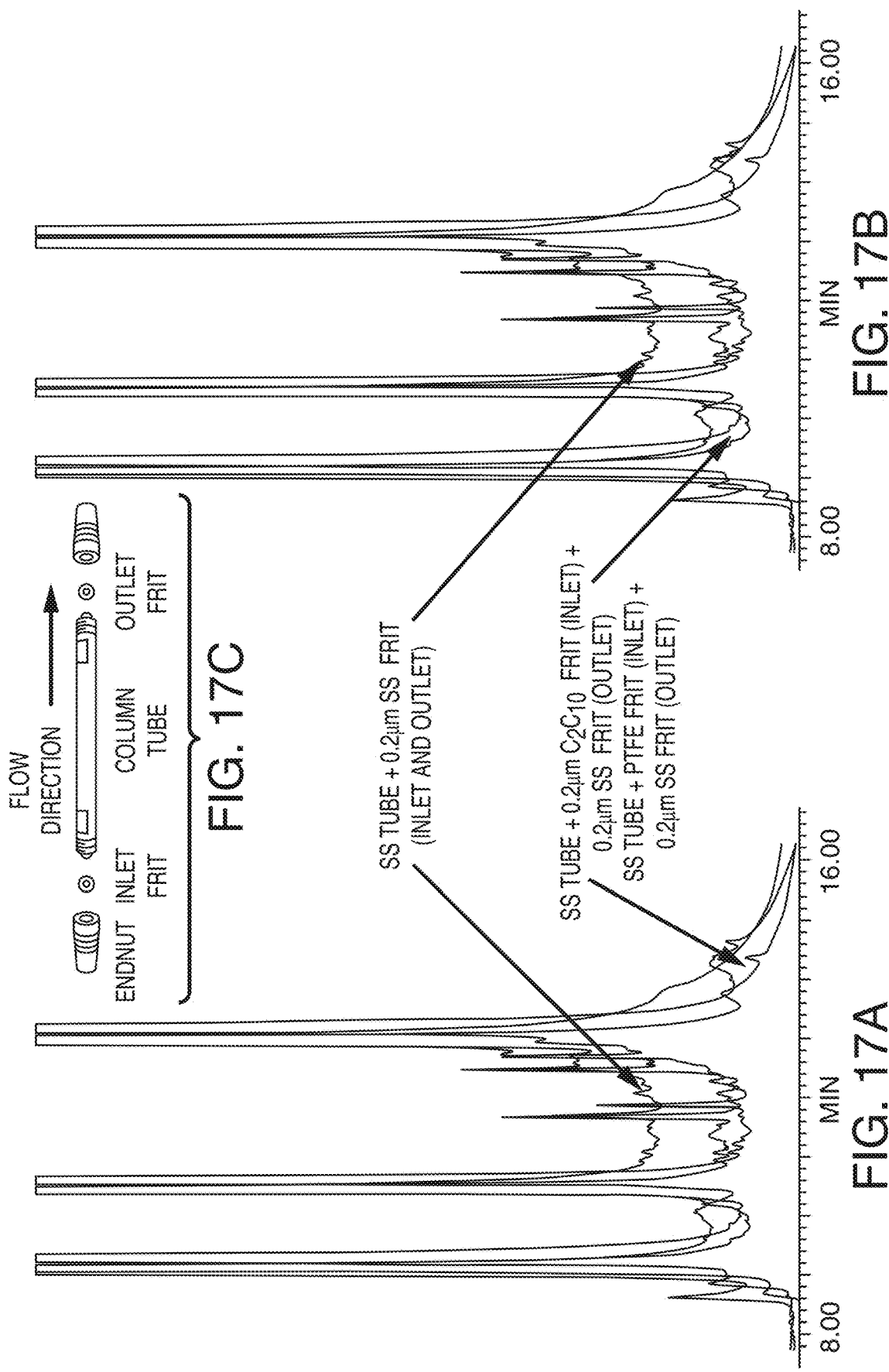

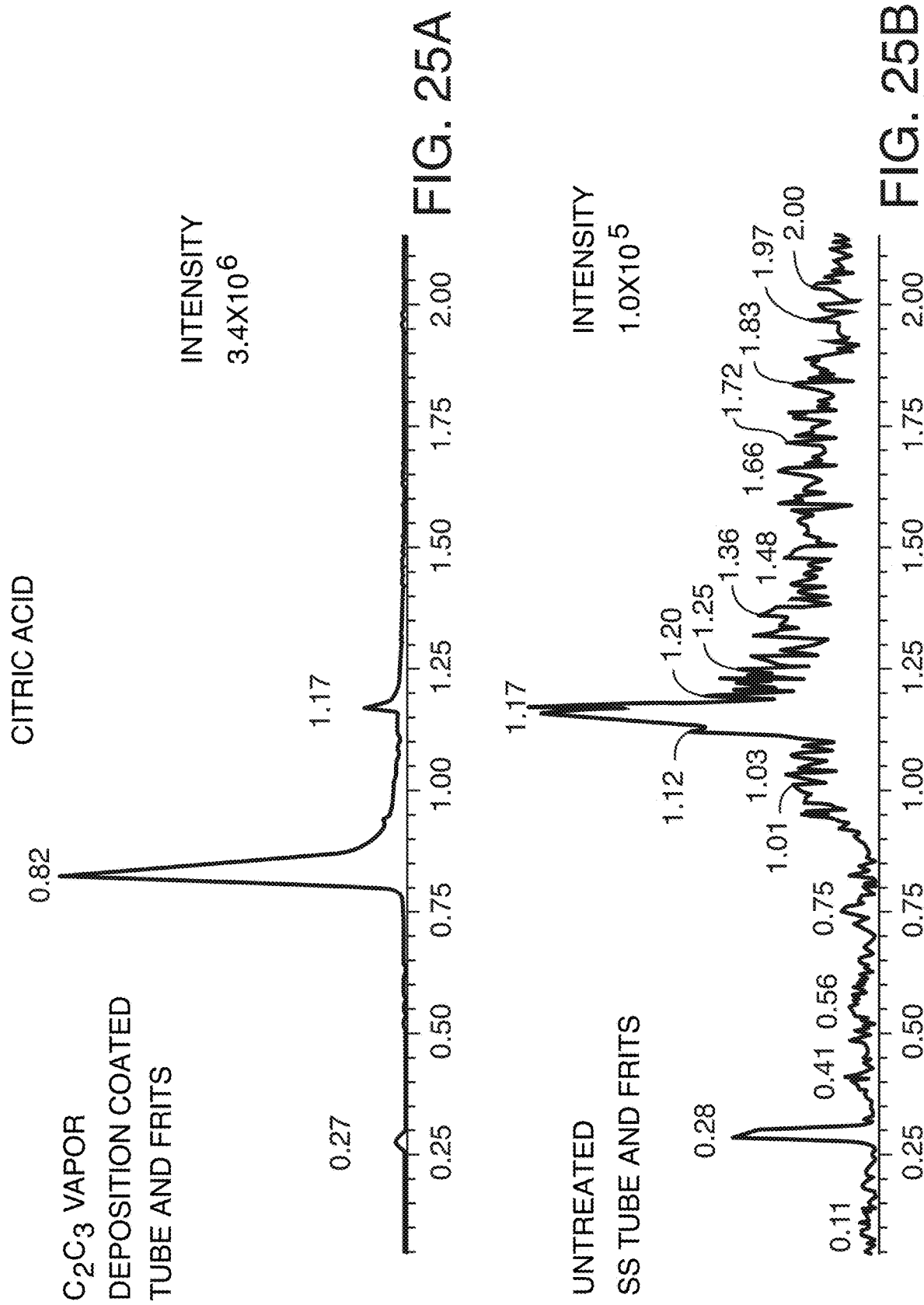

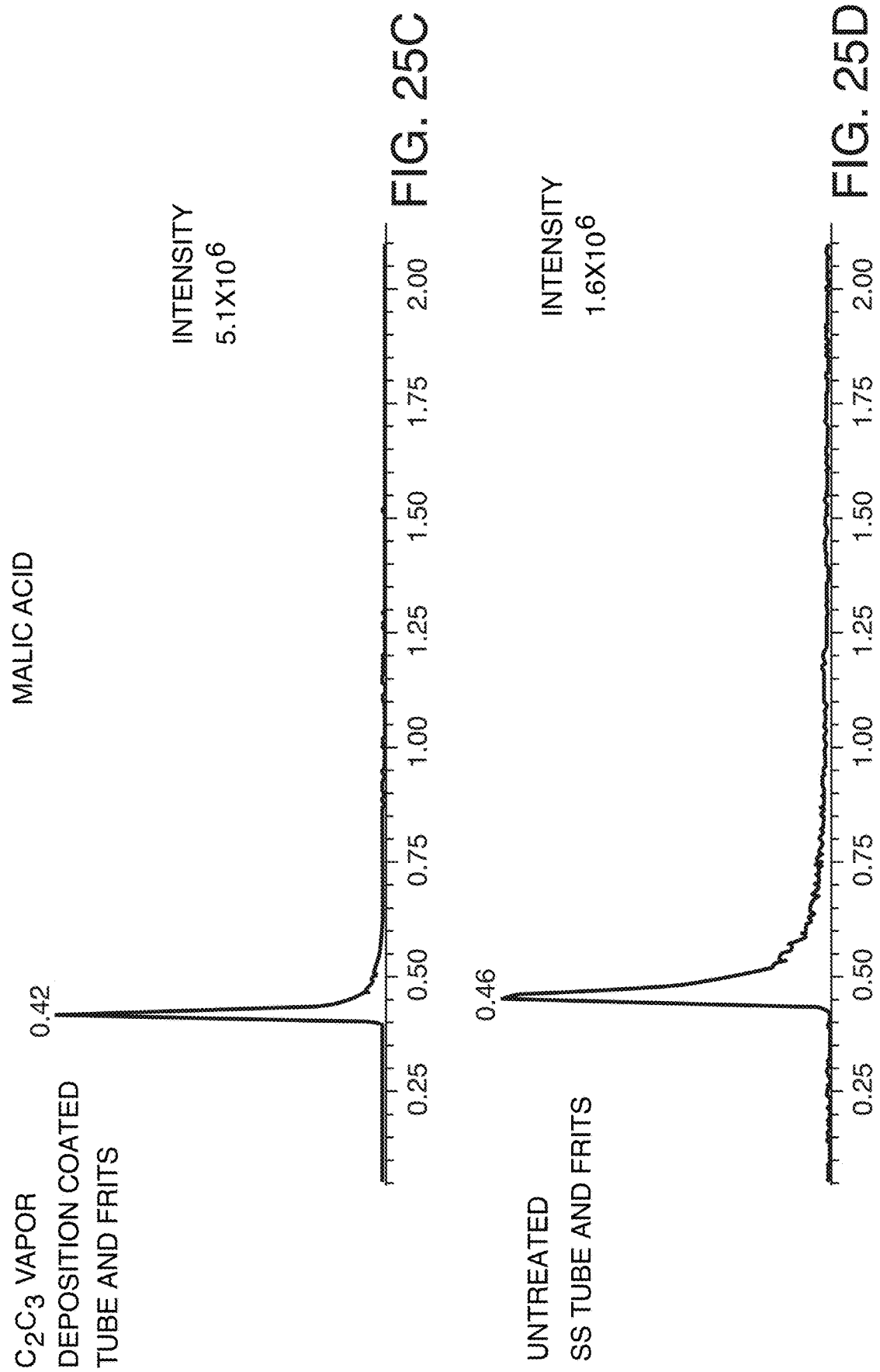

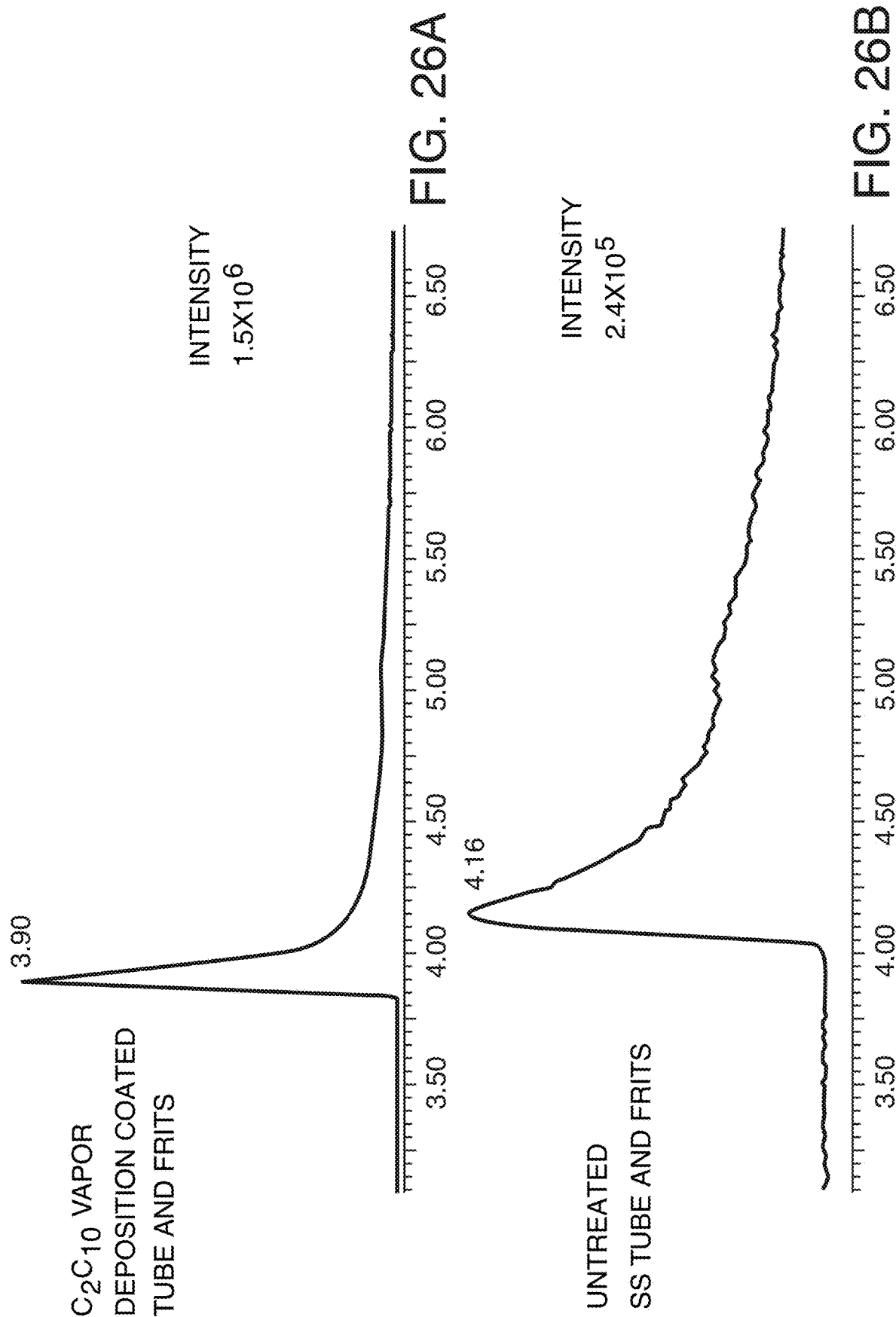

USE OF VAPOR DEPOSITION COATED FLOW PATHS FOR IMPROVED ANALYTICAL ANALYSIS

CROSS REFERENCE TO RELATED APPLICATIONS

This application is a continuation-in-part of U.S. application Ser. No. 16/133,089, filed on Sep. 17, 2018 and entitled "Use of Vapor Deposition Coated Flow Paths for Improved Chromatography of Metal Interacting Analytes", which claims priority to and benefit of U.S. provisional application No. 62/559,895 filed Sep. 18, 2017, also entitled "Use of Vapor Deposition Coated Flow Paths for Improved Chromatography of Biomolecules." The contents of each application are incorporated herein by reference in their entirety.

FIELD OF THE TECHNOLOGY

This technology relates to the use of vapor deposition coated flow paths for improved chemical separation (e.g., chromatography) and other analytical or preparative processes (e.g., extraction, filtration, sample transfer, fluid handlers and multi-channel processing). More specifically, this technology relates to devices used in the analysis or preparation of fluid samples having coated flow paths, methods of analyzing or preparing a sample (for example, glycans, peptides, pesticides, and citric acid cycle metabolites) using a fluidic system that includes coated flow paths, and methods of tailoring a fluidic flow path for an improved processing, analysis or preparation of a sample.

BACKGROUND OF THE TECHNOLOGY

Analytes that interact with metal have often proven to be very challenging to separate. The desire to have high pressure capable chromatographic systems with minimal dispersion has required that flow paths decrease in diameter and be able to withstand increasingly high pressures at increasingly fast flow rates. As a result, the material of choice for chromatographic flow paths is often metallic in nature. This is despite the fact that characteristics of certain analytes, for example, biomolecules, proteins, glycans, peptides, oligonucleotides, pesticides, bisphosphonic acids, anionic metabolites, and zwitterions like amino acids and neurotransmitters, are known to have unfavorable interactions, so called chromatographic secondary interactions, with metallic surfaces.

The proposed mechanism for metal specific binding interactions requires an understanding of the Lewis theory of acid-base chemistry. Pure metals and metal alloys (along with their corresponding oxide layers) have terminal metal atoms that have characteristics of a Lewis acid. More simply, these metal atoms show a propensity to accept donor electrons. This propensity is even more pronounced with any surface metal ions bearing a positive charge. Analytes with sufficient Lewis base characteristics (any substance that can donate non-bonding electrons) can potentially adsorb to these sites and thus form problematic non-covalent complexes. It is these substances that are defined as metal-interacting analytes.

For example, analytes having phosphate groups are excellent polydentate ligands capable of high affinity metal chelation. This interaction causes phosphorylated species to bind to the flow path metals thus reducing the detected amounts of such species, a particularly troublesome effect given that phosphorylated species are frequently the most important analytes of an assay.

Other characteristics of analytes can likewise pose problems. For example, carboxylate groups also have the ability to chelate to metals, albeit with lower affinities than phosphate groups. Yet, carboxylate functional groups are ubiquitous in, for example, biomolecules, giving the opportunity for cumulative polydentate-based adsorptive losses. These complications can exist not only on peptides and proteins, but also glycans. For example, N-glycan species can at times contain one or more phosphate groups as well as one or more carboxylate containing sialic acid residues. Additionally, smaller biomolecules such as nucleotides and saccharides, like sugar phosphates, can exhibit similar behavior to the previously mentioned N-glycan molecules. Moreover, chromatographic secondary interactions can be especially problematic with biomolecules, particularly larger structures, because they have a capacity (via their size and structural order) to form microenvironments that can adversely interact with separation components and flow path surfaces. In this case, a biomolecule or analyte having larger structures, can present structural regions with chemical properties that amplify a secondary interaction to the material of a flow path. This, combined with the cumulative metal chelation effects curtails the overall effective separation of biomolecules, pesticides, bisphosphonic acids, anionic metabolites, and zwitterions like amino acids and neurotransmitters.

An alternative to using metal flow paths is to use flow paths constructed from polymeric materials, such as polyether ether ketone (PEEK). PEEK tubing, like most polymeric materials, is formed by means of an extrusion process. With polymeric resin, this manufacturing process can lead to highly variable internal diameters. Accordingly, PEEK column hardware yields unfavorable differences in the retention times as can be observed from switching between one column and the next. Often, this variation can be a factor of three higher than a metal constructed column. In addition, the techniques for fabricating polymer based frits are not yet sufficiently optimized to afford suitably rugged components for commercial HPLC columns. For example, commercially available PEEK frits tend to exhibit unacceptably low permeability.

Other analytical or preparative devices that include fluidic flow paths experience similar challenges. These devices can be made from metals, polymeric materials (e.g., PEEK, polypropylene), plastics or glass. A common example includes any and all labware. It is a common occurrence for analytes to adsorb and be lost to labware during the manipulation of samples prior to and during analysis. Labware prone to these issues can include, but is not limited to, beakers, centrifuge tubes, pipette tips, solid phase extraction devices, molecular weight cutoff apparatus, dialysis chambers, and LC autosampler vials and well plates. Adsorptive losses to the labware decreases the strength of analytical results or amount of preparative sample.

For example, most pipette tips are made of polypropylene, as it is preferred for the sake of chemical resistance to common acids, bases and organic solvents. However, the hydrophobicity of polypropylene is known to cause high levels of adsorptive losses when used with biological analytes, like proteins and peptides. As a result, polypropylene can be identified as a major contributor to undesired sample loss. Likewise, the frits that are commonly used in extraction devices can also cause issues with adsorptive losses. In general, frits for extraction devices are commonly made from a breathable high density polyethylene or from polypropylene, such as for example Vyon® F material (available from PAR Group Limited, UK). These materials are also sufficiently hydrophobic to cause adsorptive analyte loss.

Ongoing efforts to reduce interaction between wetted surfaces and fluidic samples to provide improved outcomes are therefore needed.

SUMMARY OF THE TECHNOLOGY

One advantage of the alkylsilyl coatings of the present technology is that metal chromatographic flow paths can be used while minimizing the interactions between analytes and the metal flow paths. Coating the flow path of instrumentation and chromatographic devices with certain alklysilyl compositions improves multiple aspects of liquid chromatography separations where the analyte of interest is a metal-interacting analyte. The use of alkylsilyl coatings on metal flow paths allow the use of metal chromatographic flow paths, which are able to withstand high pressures at fast flow rates, while minimizing the secondary chromatographic interactions between the analyte and the metal. Therefore, high pressure components can be manufactured out of stainless steel or other metallic or high pressure material. These components made of high pressure material can then be tailored in that the internal flow paths can be modified with a coating to address the hydrophobicity of the flow path and reduce secondary chromatographic interactions.

Provided herein, therefore, are methods for isolating analytes comprising the use of vapor depositing one or more alklysilyl derivatives to at least one component of a fluidic system to form a bioinert or low-bind coating, and eluting the analyte through the system. Unlike ambient, liquid phase silanization, coatings which are vapor deposited tend to produce, more resilient modifications of substrates with precisely controlled thicknesses. Also, because vapor deposition is a non-line-of-sight process, this leads to a more uniform coating over substrate contours and complex surfaces. This advantage allows for coatings to be applied to flow paths with narrow internal diameters and curved surfaces, therefore addressing the need for increasingly high pressures at increasingly fast flow rates.

Also provided herein are methods of tailoring a fluidic flow path for separation of a sample comprising an analyte that includes infiltrating a vaporized source of one or more alkylsilyl derivatives through the fluidic flow path to form a bioinert (or low-bind) coating and controlling temperature and pressure to deposit a first coating on wetted surfaces of the flow path.

Also provided are methods of tailoring a fluidic flow path for separation of a sample including an analyte comprising assessing the polarity of the analyte, selecting an appropriate alkylsilyl derivative, and adjusting the hydrophobicity of wetted surfaces of the flow path by vapor depositing the appropriate alkylsilyl derivative to form a bioinert, low-bind coating.

Further provided herein are methods of improving baseline returns in a chromatographic system and other fluidic systems (e.g., sample preparation devices, sample reservoirs and containers, labware, such as pipettes and beakers, etc.) comprising introducing a sample including an analyte into a fluidic system comprising at least one vapor deposited alkylsilyl derivative to form a bioinert, low-bind coating, and eluting the sample through the system.

The disclosed methods can be applied to stainless steel or other metallic flow path components and provides a manufacturing advantage over alternative non-metallic or non-metallic lined components.

In one aspect, the technology includes a sample preparation device comprising wetted surfaces defining a fluidic path extending within an interior of the sample preparation device. At least a portion of the wetted surfaces of the fluidic path are coated with an alkylsilyl coating having Formula I:

(I)

wherein $R^1$, $R^2$, $R^3$, $R^4$, $R^5$, and $R^6$ are each independently selected from $(C_1-C_6)$alkoxy, $-NH(C_1-C_6)$alkyl, $-N((C_1-C_6)$alkyl$)_2$, OH, $OR^A$, and halo. $R^A$ represents a point of attachment to the fluidic path. At least one of $R^1$, $R^2$, $R^3$, $R^4$, $R^5$, and $R^6$ is $OR^A$. X is $(C_1-C_{20})$alkyl, $-O[(CH_2)_2O]_{1-20}-$, $-(C_1-C_{10})[NH(CO)NH(C_1-C_{10})]_{1-20}-$, or $-(C_1-C_{10})$[alkylphenyl$(C_1-C_{10})$alkyl$]_{1-20}-$.

The device of this aspect can include one or more of the following embodiments in any combination thereof. The wetted surfaces (prior to forming the alkylsilyl coating) of the sample preparation device can be made of a polymeric material. In certain embodiments, the polymeric material can include two or more different polymeric materials. In the embodiments including polymeric materials (e.g., polymers, plastics, etc.), a low or lower temperature chemical vapor deposition can be used to deposit the alkylsilyl coating especially when thermoplastic materials are utilized. In some embodiments, the wetted surfaces (prior to forming the alkylsilyl coating) are formed of glass. In other embodiments, the wetted surfaces (prior to forming the alkylsilyl coating) are formed of metal. The alkylsilyl coating can have a contact angle of at least 15°. In some embodiments, the alkylsilyl coating has a contact angle less than or equal to 30°, less than or equal to 60°, less than or equal to 90°, or less than or equal to 110°. In some embodiments, the fluidic flow path has a length to diameter ratio of at least 20. The alkylsilyl coating can have a thickness of at least 100 Å. In some embodiments, the alkylsilyl coating of Formula I can be bis(trichlorosilyl)ethane or bis(trimethoxysilyl)ethane.

In some embodiments, the device also includes a second alkylsilyl coating in direct contact with the alkylsilyl coating of Formula I. The second alkylsilyl coating has the Formula II:

(II)

$R^7$, $R^8$, and $R^9$ are each independently selected from $-NH(C_1-C_6)$alkyl, $-N[(C_1-C_6)$alkyl$]_2$, $(C_1-C_6)$alkoxy, $(C_1-C_6)$alkyl, $(C_1-C_6)$alkenyl, OH, and halo. $R^{10}$ is selected from $(C_1-C_6)$alkyl, $-OR^B$, $-[O(C_1-C_3)$alkyl$]_{1-10}O(C_1-C_6)$alkyl, $-[O(C_1-C_3)$alkyl$]_{1-10}OH$, and phenyl, wherein said $(C_1-C_6)$alkyl is optionally substituted with one or more halo and wherein said phenyl is optionally substituted with one or more groups selected from $(C_1-C_3)$alkyl, hydroxyl, fluorine, chlorine, bromine, cyano, $-C(O)NH_2$, and carboxyl. $R^B$ is $-(C_1-C_3)$alkyloxirane, $-(C_1-C_3)$alkyl-3,4-epoxycyclohexyl, or $-(C_1-C_4)$alkylOH. The hashed bond to $R^{10}$ represents an optional additional covalent bond between $R^{10}$ and the carbon bridging the silyl group to form an alkene, provided y is not 0. y is an integer from 0 to 20. In some embodiments, y is an integer from 2 to 9. In some embodiments, is 9, $R^{10}$ is methyl, and $R^7$, $R^8$, and $R^9$ are each ethoxy or chloro.

In some embodiments, the alkylsilyl coating of Formula II can be (3-glycidyloxypropyl)trimethoxysilane, n-decyltrichlorosilane, trimethylchlorosilane, trimethyldimethyaminosilane, methoxy-polyethyleneoxy(1-10) propyl trichlorosilane, or methoxy-polyethyleneoxy(1-10) propyl trimethoxysilane. In some embodiments, the alkylsilyl coating of Formula II is (3-glycidyloxypropyl)trimethoxysilane followed by hydrolysis.

In certain embodiments, the alkylsilyl coating of Formula I and II can provide a desired contact angle of about 0° to about 105°. In other embodiments, the alkylsilyl coating of Formula I and II can provide a desired contact angle of about 5° to about 60°

In some embodiments, the alkylsilyl coating of Formula I is bis(trichlorosilyl)ethane or bis(trimethoxysilyl)ethane and the alkylsilyl coating of Formula II is (3-glycidyloxypropyl)trimethoxysilane. The alkylsilyl coating of Formula I can be bis(trichlorosilyl)ethane or bis(trimethoxysilyl)ethane and the alkylsilyl coating of Formula II can be (3-glycidyloxypropyl)trimethoxysilane followed by hydrolysis. In some embodiments, the alkylsilyl coating of Formula I is bis(trichlorosilyl)ethane or bis(trimethoxysilyl)ethane and the alkylsilyl coating of Formula II is n-decyltrichlorosilane. The alkylsilyl coating of Formula I can be bis(trichlorosilyl)ethane or bis(trimethoxysilyl)ethane and the alkylsilyl coating of Formula II can be trimethylchlorosilane or trimethyldimethyaminosilane. In some embodiments, the alkylsilyl coating of Formula I is bis(trichlorosilyl)ethane or bis(trimethoxysilyl)ethane and the alkylsilyl coating of Formula II is methoxy-polyethyleneoxy(3)silane.

In some embodiments, the processing device can also include an alkylsilyl coating having the Formula III in direct contact with the alkylsilyl coating of Formula I,

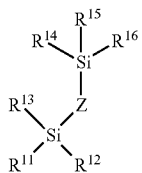

(III)

$R^{11}$, $R^{12}$, $R^{13}$, $R^{14}$, $R^{15}$, and $R^{16}$ are each independently selected from $(C_1-C_6)$alkoxy, $-NH(C_1-C_6)$alkyl, $-N((C_1-C_6)$alkyl$)_2$, OH, and halo. Z is $(C_1-C_{20})$alkyl, $-O[(CH_2)_2O]_{1-20}-$, $-(C_1-C_{10})[NH(CO)NH(C_1-C_{10})]_{1-20}-$, or $-(C_1-C_{10})[alkylphenyl(C_1-C_{10})alkyl]_{1-20}-$.

In some embodiments, the alkylsilyl coating of Formula III is bis(trichlorosilyl)ethane or bis(trimethoxysilyl)ethane. The alkylsilyl coating of Formula I can be bis(trichlorosilyl)ethane or bis(trimethoxysilyl)ethane and the alkylsilyl coating of Formula III can be bis(trichlorosilyl)ethane or bis(trimethoxysilyl)ethane. In some embodiments, the alkylsilyl coating of I and III has a total thickness of about 400 Å.

In another aspect, the technology relates to a method of processing a sample comprising a glycan, a peptide, or a pesticide. The method includes introducing the sample comprising the glycan, the peptide, or the pesticide to a processing device including a flow path disposed in an interior of the processing device. The flow path comprising a alkylsilyl coating having the Formula I:

(I)

$R^1$, $R^2$, $R^3$, $R^4$, $R^5$, and $R^6$ are each independently selected from $(C_1-C_6)$alkoxy, $-NH(C_1-C_6)$alkyl, $-N((C_1-C_6)$alkyl$)_2$, OH, $OR^A$, and halo. $R^A$ represents a point of attachment to the interior surfaces of the fluidic system. At least one of $R^1$, $R^2$, $R^3$, $R^4$, $R^5$, and $R^6$ is $OR^A$. X is $(C_1-C_{20})$alkyl, $-O[(CH_2)_2O]_{1-20}-$, $-(C_1-C_{10})[NH(CO)NH(C_1-C_{10})]_{1-20}-$, or $-(C_1-C_{10})[alkylphenyl(C_1-C_{10})alkyl]_{1-20}-$. A second alkylsilyl coating is in direct contact with the alkylsilyl coating of Formula I. the second alkylsilyl coating has the Formula II:

(II)

$R^7$, $R^8$, and $R^9$ are each independently selected from $-NH(C_1-C_6)$alkyl, $-N[(C_1-C_6)$alkyl$]_2$, $(C_1-C_6)$alkoxy, $(C_1-C_6)$alkyl, $(C_1-C_6)$alkenyl, OH, and halo. $R^{10}$ is selected from $(C_1-C_6)$alkyl, $-OR^B$, $-[O(C_1-C_3)$alkyl$]_{1-10}O(C_1-C_6)$alkyl, $-[O(C_1-C_3)$alkyl$]_{1-10}OH$, and phenyl. $(C_1-C_6)$alkyl is optionally substituted with one or more halo. The phenyl is optionally substituted with one or more groups selected from $(C_1-C_3)$alkyl, hydroxyl, fluorine, chlorine, bromine, cyano, $-C(O)NH_2$, and carboxyl.

$R^B$ is $-(C_1-C_3)$alkyloxirane, $-(C_1-C_3)$alkyl-3,4-epoxycyclohexyl, or $-(C_1-C_4)$alkylOH. The hashed bond to $R^{10}$ represents an optional additional covalent bond between $R^{10}$ and the carbon bridging the silyl group to form an alkene, provided y is not 0. y is an integer from 0 to 20. The method also includes eluting the sample through the fluidic system, thereby isolating the glycan, the peptide or the pesticide. The method can include one or more of the embodiments described herein in any combination thereof.

In some embodiments, the flow path is defined at least in part by the interior wall surfaces of a processing device (e.g., solid phase extraction device). The flow path can be further defined at least in part by passageways through a frit within the processing device. In some embodiments, the flow path is further defined at least in part by interior surfaces of tubing or connectors. The flow path can be formed of stainless steel. In other embodiments the flow path can be formed of glass or polymeric material.

In some embodiments, the glycan is a phosphoglycan. The peptide can be a phosphopeptide. The pesticide can be glyphosate.

In some embodiments, the alkylsilyl coating of Formula I is bis(trichlorosilyl)ethane or bis(trimethoxysilyl)ethane. The alkylsilyl coating of Formula II can be n-decyltrichlorosilane. In some embodiments, the alkylsilyl coating of Formula I is bis(trichlorosilyl)ethane or bis(trimethoxysilyl)ethane and the alkylsilyl coating of Formula II is n-decyltrichlorosilane.

In another aspect, the technology includes a method of processing a sample comprising a citric acid cycle metabolite. The method includes introducing the sample comprising the citric acid cycle metabolite to a processing device including a flow path disposed in an interior of the processing device. The flow path includes a alkylsilyl coating has the Formula I:

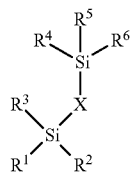

(I)

$R^1$, $R^2$, $R^3$, $R^4$, $R^5$, and $R^6$ are each independently selected from $(C_1-C_6)$alkoxy, —NH$(C_1-C_6)$alkyl, —N$((C_1-C_6)$alkyl$)_2$, OH, OR$^A$, and halo. R$^A$ represents a point of attachment to the interior surfaces of the processing device. At least one of $R^1$, $R^2$, $R^3$, $R^4$, $R^5$, and $R^6$ is OR$^A$. X is $(C_1-C_{20})$alkyl, —O[$(CH_2)_2$O]$_{1-20}$—, —$(C_1-C_{10})$[NH(CO)NH$(C_1-C_{10})$]$_{1-20}$—, or —$(C_1-C_{10})$[alkylphenyl$(C_1-C_{10})$alkyl]$_{1-20}$; A second alkylsilyl coating is in direct contact with the alkylsilyl coating of Formula I. The second alkylsilyl coating has the Formula II:

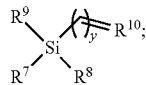

(II)

$R^7$, $R^8$, and $R^9$ are each independently selected from —NH$(C_1-C_6)$alkyl, —N[$(C_1-C_6)$alkyl]$_2$, $(C_1-C_6)$alkoxy, $(C_1-C_6)$alkyl, $(C_1-C_6)$alkenyl, OH, and halo. $R^{10}$ is selected from $(C_1-C_6)$alkyl, —OR$^B$, —[O$(C_1-C_3)$alkyl]$_{1-10}$O$(C_1-C_6)$alkyl, —[O$(C_1-C_3)$alkyl]$_{1-10}$OH, and phenyl. The $(C_1-C_6)$alkyl is optionally substituted with one or more halo. The phenyl is optionally substituted with one or more groups selected from $(C_1-C_3)$alkyl, hydroxyl, fluorine, chlorine, bromine, cyano, —C(O)NH$_2$, and carboxyl. $R^B$ is —$(C_1-C_3)$alkyloxirane, —$(C_1-C_3)$alkyl-3,4-epoxycyclohexyl, or —$(C_1-C_4)$alkylOH. The hashed bond to $R^{10}$ represents an optional additional covalent bond between $R^{10}$ and the carbon bridging the silyl group to form an alkene, provided y is not 0. y is an integer from 0 to 20. The method also includes eluting the sample through the processing device, thereby isolating the citric acid cycle metabolite.

The method can include one or more of the embodiments described herein in any combination thereof. In some embodiments, the flow path is defined at least in part by the interior wall surfaces of a processing device (e.g., solid phase extraction device). The flow path can be further defined at least in part by passageways through a frit. The flow path can be further defined at least in part by interior surfaces of tubing. The citric acid cycle metabolite can be citric acid or malic acid.

In some embodiments, the alkylsilyl coating of Formula I is bis(trichlorosilyl)ethane or bis(trimethoxysilyl)ethane. The alkylsilyl coating of Formula II can be trimethylchlorosilane or trimethyldimethylaminosilane. In some embodiments, the alkylsilyl coating of Formula I is bis(trichlorosilyl)ethane or bis(trimethoxysilyl)ethane and the alkylsilyl coating of Formula II is trimethylchlorosilane or trimethyldimethyaminosilane.

In another aspect, the technology includes a method of tailoring a fluidic flow path of a sample processing device (e.g., sample preparation device, solid phase extraction device, labware). The method includes assessing a polarity of an analyte in a sample to be processed and of wetted surfaces of the sample preparation device, and selecting a alkylsilyl coating based to minimize adsorptive losses to the wetted surfaces based on a difference in hydrophobicity of the analyte and the wetted surfaces of the processing device, wherein the alkylsilyl coating has the Formula I:

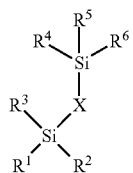

(I)

wherein $R^1$, $R^2$, $R^3$, $R^4$, $R^5$, and $R^6$ are each independently selected from $(C_1-C_6)$alkoxy, —NH$(C_1-C_6)$alkyl, —N$((C_1-C_6)$alkyl$)_2$, OH, OR$^A$, and halo. R$^A$ represents a point of attachment to wetted surfaces of the processing device. At least one of $R^1$, $R^2$, $R^3$, $R^4$, $R^5$, and $R^6$ is OR$^A$. X is $(C_1-C_{20})$alkyl, —O[$(CH_2)_2$O]$_{1-20}$—, —$(C_1-C_{10})$[NH(CO)NH$(C_1-C_{10})$]$_{1-20}$—, or —$(C_1-C_{10})$[alkylphenyl$(C_1-C_{10})$alkyl]$_{1-20}$-. The method also includes adjusting a hydrophobicity of the wetted surfaces of the by vapor depositing the alkylsilyl coating onto the wetted surfaces.

The method can include one or more of the embodiments described herein in any combination thereof. The alkylsilyl coating can provide a desired contact angle of about 0° to about 95°. In certain embodiments, the alkylsilyl coating can provide a desired contact angle of about 5° to about 60°. In some embodiments, the wetted surface of the processing device are defined at least in part by an interior wall surfaces within a solid phase extraction device. In certain embodiments, the wetted surfaces include the flow through surfaces of a frit within the solid phase extraction device. In some embodiments, the wetted surfaces of the processing device are defined at least in part by interior surfaces of a pipette tip.

In some embodiments, the alkylsilyl coating of Formula I is bis(trichlorosilyl)ethane or bis(trimethoxysilyl)ethane. The method can also include annealing the alkylsilyl coating after vapor depositing the alkylsilyl coating onto the wetted surfaces. In some embodiments, the method also includes modifying the alkylsilyl coating of Formula I with a silanizing reagent to obtain a desired thickness of the alkylsilyl coating. The silanizing reagent can be a non-volatile zwitterion. The non-volatile zwitterion can be sulfobetaine or carboxybetaine. The silanizing reagent can be an acidic or basic silane. In some embodiments, the silanizing agent is methoxy-polyethyleneoxy(6-9)silane.

In some embodiments, the method also includes adjusting the hydrophobicity of the wetted surfaces by vapor depositing a second alkylsilyl coating in direct contact with the vapor deposited alkylsilyl coating of Formula I. The second alkylsilyl coating has the Formula II:

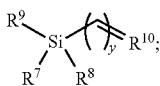

(II)

$R^7$, $R^8$, and $R^9$ are each independently selected from —NH($C_1$-$C_6$)alkyl, —N[($C_1$-$C_6$)alkyl]$_2$, ($C_1$-$C_6$)alkoxy, ($C_1$-$C_6$)alkyl, ($C_1$-$C_6$)alkenyl, OH, and halo. $R^{10}$ is selected from ($C_1$-$C_6$)alkyl, —OR$^B$, —[O($C_1$-$C_3$)alkyl]$_{1-10}$O($C_1$-$C_6$)alkyl, —[O($C_1$-$C_3$)alkyl]$_{1-10}$OH, and phenyl, wherein said ($C_1$-$C_6$) alkyl is optionally substituted with one or more halo and wherein said phenyl is optionally substituted with one or more groups selected from ($C_1$-$C_3$)alkyl, hydroxyl, fluorine, chlorine, bromine, cyano, —C(O)NH$_2$, and carboxyl/R$^B$ is —($C_1$-$C_3$)alkyloxirane, —($C_1$-$C_3$)alkyl-3,4-epoxycyclohexyl, or —($C_1$-$C_4$)alkylOH. The hashed bond to $R^{10}$ represents an optional additional covalent bond between $R^{10}$ and the carbon bridging the silyl group to form an alkene, provided y is not 0. y is an integer from 0 to 20.

In some embodiments, the alkylsilyl coating of Formula II is (3-glycidyloxypropyl)trimethoxysilane, n-decyltrichlorosilane, trimethylchlorosilane, trimethyldimethyaminosilane, or methoxy-polyethyleneoxy(3)silane. The alkylsilyl coating of Formula II can be (3-glycidyloxypropyl) trimethoxysilane followed by hydrolysis.

In some embodiments, the alkylsilyl coating of Formula I and II provides a desired contact angle of about 0° to about 105°. In some embodiments, the alkylsilyl coating of Formula I and II provides a desired contact angle of about 5° to about 35°.

The method can also include modifying the alkylsilyl coating of Formula II with a silanizing reagent to obtain a desired thickness of the alkylsilyl coating. The silanizing reagent can be a non-volatile zwitterion. The non-volatile zwitterion can be sulfobetaine or carboxybetaine. The silianizing reagent can be an acidic or basic silane. In some embodiments, the silanizing agent is methoxy-polyethyleneoxy(6-9)silane.

In some embodiments, the analyte is a biomolecule. The biomolecule is a peptide or peptide fragment, an oligopeptide, a protein, a glycan, a nucleic acid or nucleic acid fragment, a growth factor, a carbohydrate, a fatty acid or a lipid. The analyte can be a citric acid cycle metabolite. In some embodiments, the analyte is a pesticide.

In another aspect, the technology includes a method of tailoring a fluidic flow path for separation of a sample. The method includes infiltrating a vaporized source of an alkylsilyl of Formula III on wetted surfaces

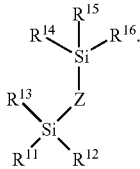

(III)

Wherein $R^{11}$, $R^{12}$, $R^{13}$, $R^{14}$, $R^{15}$, and $R^{16}$ are each independently selected from ($C_1$-$C_6$)alkoxy, —NH($C_1$-$C_6$)alkyl, —N(($C_1$-$C_6$)alkyl)$_2$, OH, and halo. Z is ($C_1$-$C_{20}$)alkyl, —O[(CH$_2$)$_2$O]$_{1-20}$—, —($C_1$-$C_{10}$)[NH(CO)NH($C_1$-$C_{10}$)]$_{1-20}$—, or —($C_1$-$C_{10}$)[alkylphenyl($C_1$-$C_{10}$)alkyl]$_{1-20}$-. The method also includes controlling temperature and pressure to deposit a first coating of Formula III on the wetted surfaces of the processing device, the first coating having a thickness of at least 100 Å and a contact angle of at least 15°. The method can include one or more of the embodiments described herein in any combination thereof.

In some embodiments, the method also includes pretreating the wetted surfaces with a plasma prior to depositing the first coating of Formula III.

The method can also include modifying the alkylsilyl coating of Formula III with a silanizing reagent to obtain a desired thickness of the alkylsilyl coating. The silanizing reagent can be a non-volatile zwitterion. The non-volatile zwitterion can be sulfobetaine or carboxybetaine. The silianizing reagent can be an acidic or basic silane. In some embodiments, the silanizing agent is methoxy-polyethyleneoxy(6-9)silane.

BRIEF DESCRIPTION OF THE DRAWINGS

FIG. 4A shows a fluorescence chromatogram obtained using uncoated stainless steel hardware, in accordance with an illustrative embodiment of the technology FIG. 4B shows a fluorescence chromatogram obtained using hardware coated with exemplary vapor deposited alkylsilyl, in accordance with an illustrative embodiment of the technology.

FIG. 9A is a chromatogram showing the effects of employing vapor deposition coated column hardware for the reversed phase LC analyses of fructose-6-phosphate, in accordance with an illustrative embodiment of the technology.

FIG. 9B is a chromatogram showing the effects of employing untreated column hardware for the reversed phase LC analyses of fructose-6-phosphate, in accordance with an illustrative embodiment of the technology.

FIG. 10A is a chromatogram showing the effects of employing vapor deposition coated column hardware for the reversed phase LC analyses of adenosine triphosphate, in accordance with an illustrative embodiment of the technology.

FIG. 10B is a chromatogram showing the effects of employing untreated column hardware for the reversed phase LC analyses of adenosine triphosphate, in accordance with an illustrative embodiment of the technology.

FIG. 12A is a fluorescence chromatogram for fetuin N-glycans obtained with untreated stainless steel, in accordance with an illustrative embodiment of the technology.

FIG. 12B is a fluorescence chromatogram for fetuin N-glycans obtained with vapor deposition coated hardware, in accordance with an illustrative embodiment of the technology.

FIG. 14A is a reversed phase fluorescence chromatogram of reduced, IdeS-digested NIST Reference Material 8671 obtained with column hardware components treated with coatings in accordance with illustrative embodiments of the technology.

FIG. 14B is a reversed phase fluorescence chromatogram of reduced, IdeS-digested NIST Reference Material 8671 obtained with column hardware components treated with coatings in accordance with illustrative embodiments of the technology.

FIG. 15A is a reversed phase total ion chromatogram for columns constructed with stainless steel alternatives, namely polyether ether ketone (PEEK) and a low titanium, nickel cobalt alloy (MP35NLT) with various components coated, in accordance with an illustrative embodiment of the technology.

FIG. 15B is a reversed phase total ion chromatogram for column components constructed with stainless steel, $C_2$ coatings and $C_2C_{10}$ coatings, in accordance with an illustrative embodiment of the technology.

FIG. 16A shows fluorescence chromatograms of reduced, IdeS-digested NIST Reference Material 8671 and the effect on baseline return when various components of the system are coated, in accordance with an illustrative embodiment of the technology.

FIG. 16B shows reversed phase total ion chromatograms (TICs) reduced, IdeS-digested NIST Reference Material 8671 and the effect on baseline return when various components of the system are coated, in accordance with an illustrative embodiment of the technology.

FIG. 16C is a schematic of the column tube and frits that were coated and used to obtain the chromatograms of FIGS. 16A and 16B, in accordance with an illustrative embodiment of the technology.

FIG. 17A shows fluorescence chromatograms of reduced, IdeS-digested NIST Reference Material 8671 and the effect on baseline return when various components of the system are coated, in accordance with an illustrative embodiment of the technology.

FIG. 17B shows reversed phase total ion chromatograms (TICs) of reduced, IdeS-digested NIST Reference Material 8671 and the effect on baseline return when various components of the system are coated, in accordance with an illustrative embodiment of the technology.

FIG. 17C is a schematic of the column tube and frits that were coated and used to obtain the chromatograms of FIGS. 17A and 17B, in accordance with an illustrative embodiment of the technology

FIG. 25A is a reversed phase MRM (multiple reaction monitoring) chromatogram obtained for citric acid with the use of a 2.1×50 mm 1.8 μm silica 100 Å $C_{18}$ 1.8 μm column constructed with $C_2C_3$ vapor deposition coated components, in accordance with an illustrative embodiment of the technology.

FIG. 25B is a reversed phase MRM (multiple reaction monitoring) chromatogram obtained for citric acid with the use of a 2.1×50 mm 1.8 μm silica 100 Å $C_{18}$ 1.8 μm column constructed with untreated components, in accordance with an illustrative embodiment of the technology.

FIG. 25C is a reversed phase MRM (multiple reaction monitoring) chromatogram obtained for malic acid with the use of a 2.1×50 mm 1.8 μm silica 100 Å $C_{18}$ 1.8 μm column constructed with $C_2C_3$ vapor deposition coated components, in accordance with an illustrative embodiment of the technology.

FIG. 25D is a reversed phase MRM (multiple reaction monitoring) chromatogram obtained for malic acid with the use of a 2.1×50 mm 1.8 μm silica 100 Å $C_{18}$ 1.8 μm column constructed with untreated components, in accordance with an illustrative embodiment of the technology.

FIG. 26A is a mixed mode hydrophilic interaction chromatography (HILIC) MRM (multiple reaction monitoring) chromatogram of glyphosate showing MRM peak intensities obtained for glyphosate with the use of a 2.1×100 mm 1.7 μm diethylamine bonded organosilica 130 Å column constructed with $C_2C_{10}$ vapor deposition coated components, in accordance with an illustrative embodiment of the technology.

FIG. 26B is a mixed mode hydrophilic interaction chromatography (HILIC) MRM (multiple reaction monitoring) chromatogram of glyphosate showing MRM peak intensities obtained for glyphosate with the use of a 2.1×100 mm 1.7

μm diethylamine bonded organosilica 130 Å column with uncoated components, in accordance with an illustrative embodiment of the technology.

Figure 27B:
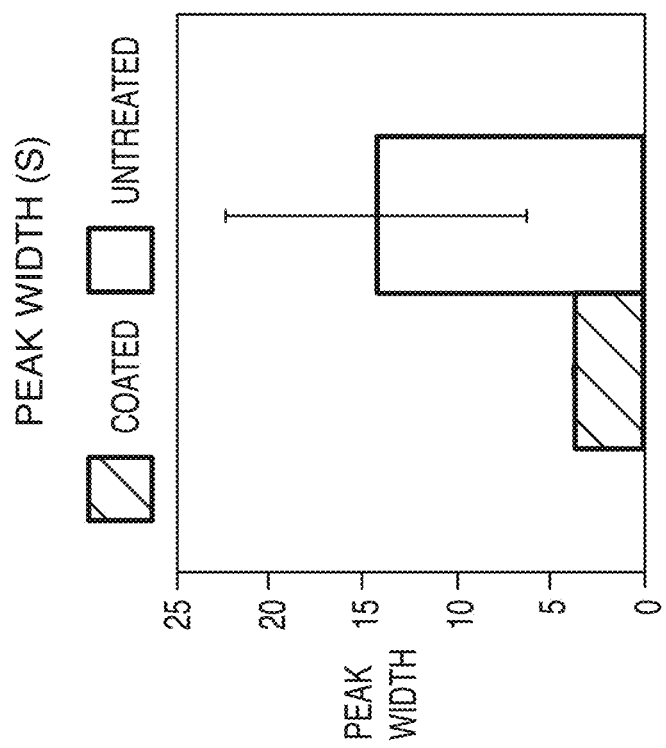
Figure 27A:
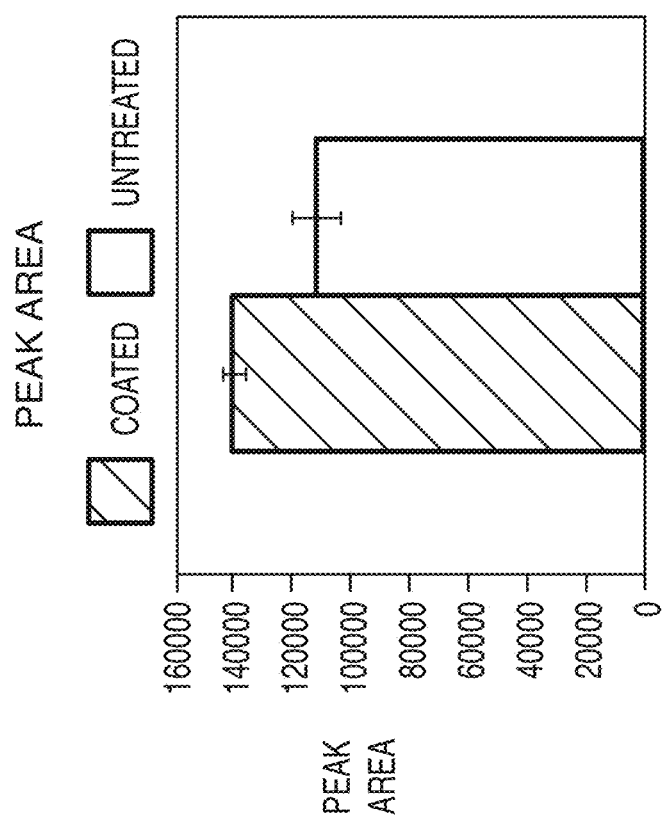

FIG. 27A is a graph showing the average peak areas of glyphosate as observed during mixed mode HILIC using either a 2.1×100 mm 1.7 μm diethylamine bonded organosilica 130 Å column constructed with either untreated or $C_2C_{10}$ vapor deposition coated components in accordance with an illustrative embodiment of the technology. The analyses were performed with six replicate injections.

FIG. 27B is a graph showing the average peak widths of glyphosate as observed during mixed mode HILIC using either a 2.1×100 mm 1.7 μm diethylamine bonded organosilica 130 Å column constructed with either untreated or $C_2C_{10}$ vapor deposition coated components, in accordance with an illustrative embodiment of the technology. The analyses were performed with six replicate injections.

FIG. 28A is a graph showing the amount of rabbit IgG recovered in flow-through for various fritted pipette tips (200 μL of a alkylsilyl coated tip, a plasma treated tip, and an untreated tip; 1000 μL of a alkylsilyl coated tip, a plasma treated tip, and an untreated tip).

Figure 28:
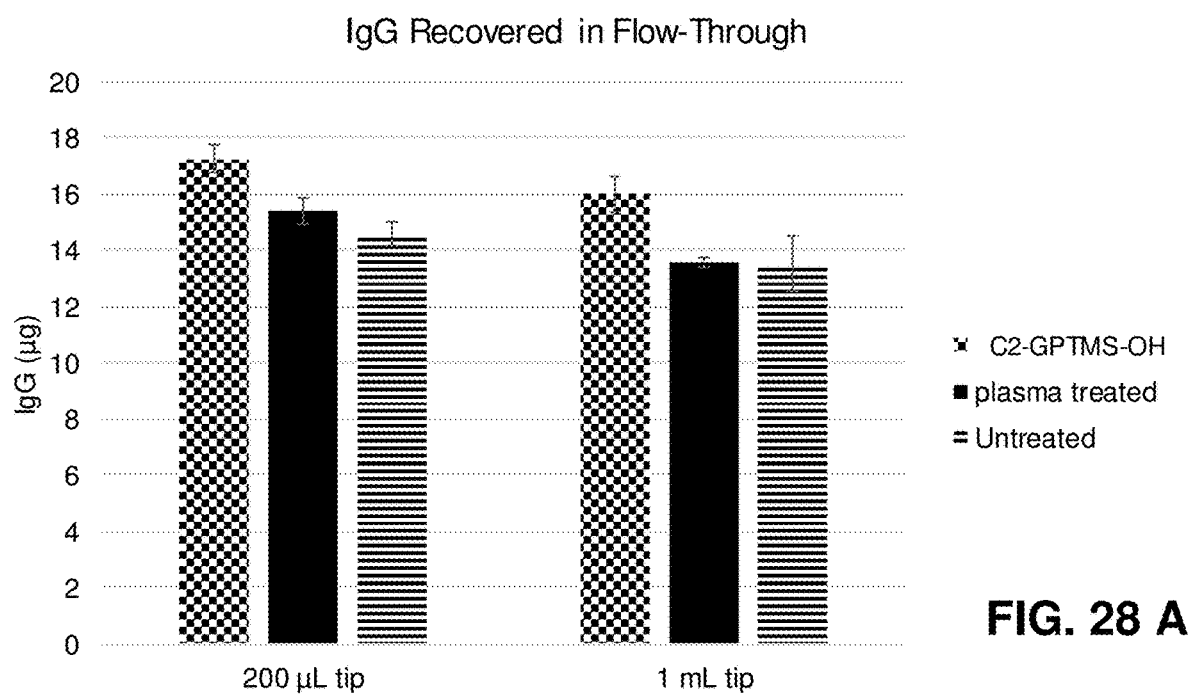
Figure 28:
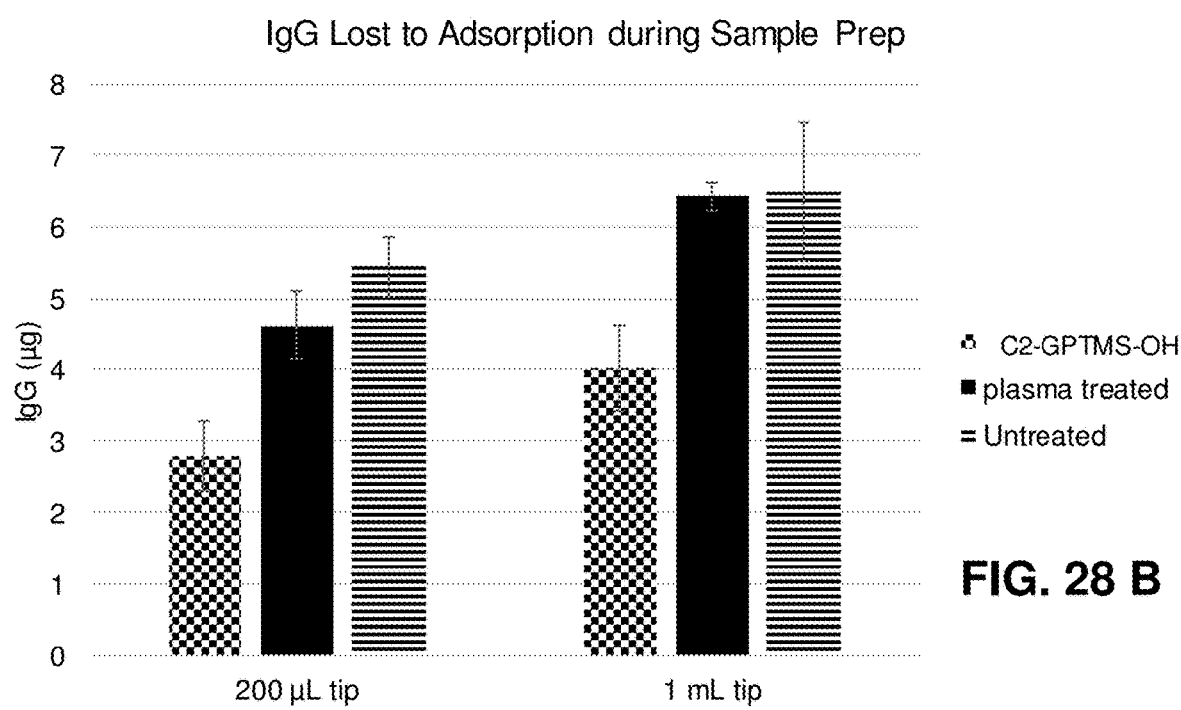

FIG. 28 B is a graph showing the amount of IgG lost to adsorption during sample preparation for various fritted pipette tips (200 μL of a alkylsilyl coated tip, a plasma treated tip, and an untreated tip; 1000 μL of a alkylsilyl coated tip, a plasma treated tip, and an untreated tip).

DETAILED DESCRIPTION

In general, a number of aspects of the technology are directed to (1) devices having an alkylsilyl coating; (2) methods of tailoring or tuning a flow path for isolation of an analyte or processing a sample; (3) method of isolating an analyte in a sample, in particular a metal-interacting analyte; and (4) kits comprising various labware or chromatographic components coated with an alkylsilyl coating and instructions for use. In some aspects, a bioinert, low-bind coating is used to modify a flow path to address flow path interactions with an analyte or sample to be processed. That is, the bioinert, low-bind coating minimizes surface reactions with the interacting analyte and allows the analyte to pass along a flow path without clogging, attaching to surfaces, or change in analyte properties. The reduction/elimination of these interactions is advantageous because it allows for accurate quantification and analysis of a sample containing an interacting analyte, for example biomolecules, proteins, glycans, peptides, oligonucleotides, pesticides, bisphosphonic acids, anionic metabolites, and zwitterions like amino acids and neurotransmitters. The biomolecule can be selected from a peptide or peptide fragment, an oligopeptide, a protein, a glycan, a nucleic acid or nucleic acid fragment, a growth factor, a carbohydrate, a fatty acid, and a lipid. In one aspect, the biomolecule is a protein, a peptide, or a glycan. The biomolecule can be a phosphoglycan or a phosphopeptide.

In the present technology, vapor deposited alkylsilyl coatings on wetted surfaces of fluidic systems (e.g., liquid chromatography systems, extraction devices, pipettes, etc) to modify the fluidic path and decrease secondary interactions. As such, they are bioinert or low-bind (meaning that analytes of a sample do not interact, or have minimal interaction, with the alkylsilyl coating). In addition, the deposited coatings are highly tunable to provide a range of desirable contact angles (e.g., make the wetted surfaces hydrophilic or hydrophobic), chemistries, and properties to achieve a desired effect on the flow path and ultimately the sample passing through the flow path.

Devices

Figure 1:
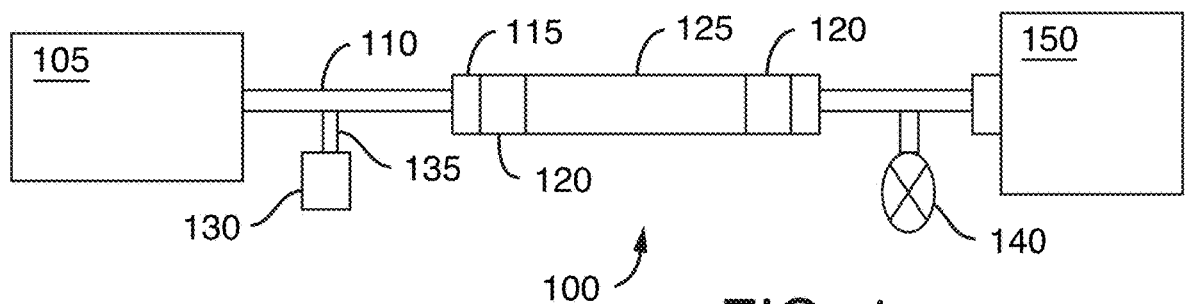
FIG. 1 is a schematic of a chromatographic flow system including a chromatography column and various other components, in accordance with an illustrative embodiment of the technology. A fluid is carried through the chromatographic flow system with a fluidic flow path extending from a fluid manager to a detector.

FIG. 1 is a representative schematic of a chromatographic flow system/device 100 that can be used to separate analytes in a sample. Chromatographic flow system 100 includes several components including a fluid manager system 105 (e.g., controls mobile phase flow through the system), tubing 110 (which could also be replaced or used together with microfabricated fluid conduits), fluid connectors 115 (e.g., fluidic caps), frits 120, a chromatography column 125, a sample injector 135 including a needle (not shown) to insert or inject the sample into the mobile phase, a vial, sinker, or sample reservoir 130 for holding the sample prior to injection, a detector 150 and a pressure regulator 140 for controlling pressure of the flow. Interior surfaces of the components of the chromatographic system/device form a fluidic flow path that has wetted surfaces. The fluidic flow path can have a length to diameter ratio of at least 20, at least 25, at least 30, at least 35 or at least 40.

The detector 150, can be a mass spectrometer. The fluidic flow path can include wetted surfaces of an electrospray needle (not shown).

At least a portion of the wetted surfaces can be coated with an alkyl silyl coating, described in detail herein, to tailor its hydrophobicity. The coating can be applied by vapor deposition. As such, methods and devices of the present technology provide the advantage of being able to use high pressure resistant materials (e.g., stainless steel) for the creation of the flow system, but also being able to tailor the wetted surfaces of the fluidic flow path to provide the appropriate hydrophobicity so deleterious interactions or undesirable chemical effects on the sample can be minimized.

The alkylsilyl coating can be provided throughout the system from the tubing or fluid conduits 110 extending from the fluid manager system 105 all the way through to the detector 150. The coatings can also be applied to portions of the fluidic fluid path. That is, one may choose to coat one or more components or portions of a component and not the entire fluidic path. For example, the internal portions of the column 125 and its frits 120 and end caps 115 can be coated whereas the remainder of the flow path can be left unmodified. Further, removable/replaceable components can be coated. For example, the vial or sinker 130 containing the sample reservoir can be coated as well as frits 120.

In one aspect, the flow path of the fluidic systems described herein is defined at least in part by an interior surface of tubing. In another aspect, the flow path of the fluidic systems described herein is defined at least in part by an interior surface of microfabricated fluid conduits. In another aspect, the flow path of the fluidic systems described herein is defined at least in part by an interior surface of a column. In another aspect, the flow path of the fluidic systems described herein is defined at least in part by passageways through a frit. In another aspect, the flow path of the fluidic systems described herein is defined at least in part by an interior surface of a sample injection needle. In another aspect, the flow path of the fluidic systems described herein extends from the interior surface of a sample injection needle throughout the interior surface of a column. In another aspect, the flow path extends from a sample reservoir container (e.g. sinker) disposed upstream of and in fluidic communication with the interior surface of a sample injection needle throughout the fluidic system to a connector/port to a detector.

In some embodiments, only the wetted surfaces of the chromatographic column and the components located upstream of the chromatographic column are coated with the alkylsilyl coatings described herein while wetted surfaces located downstream of the column are not coated. The coating can be applied to the wetted surfaces via vapor deposition. Similarly, the "wetted surfaces" of labware or other fluid processing devices may benefit from alkylsiyl coatings described herein. The "wetted surfaces" of these devices not only include the fluidic flow path, but also elements that reside within the fluidic flow path. For example, frits and/or membranes within a solid phase extraction device come in contact with fluidic samples. As a result, not only the internal walls within a solid phase extraction device, but also any frits/membranes are included within the scope of "wetted surfaces." All "wetted surfaces" or at least some portion of the "wetted surfaces" can be improved or tailored for a particular analysis or procedure by including one or more of the coatings described herein. The term "wetted surfaces" refers to all surfaces within a device (e.g., chromatography column, chromatography injection system, chromatography fluid handling system, labware, solid phase extraction device, pipette tips, centrifuge tubes, beakers, dialysis chambers, etc.) that come into contact with a fluid, especially a fluid containing an analyte of interest.

At least a portion of the wetted surfaces are coated with an alkylsilyl coating. The alkylsilyl coating is inert to at least one of the analytes in the sample. The alkylsilyl coating can have the Formula I:

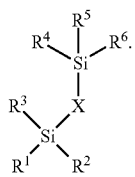

(I)

$R^1$, $R^2$, $R^3$, $R^4$, $R^5$, and $R^6$ are each independently selected from $(C_1-C_6)$alkoxy, —NH$(C_1-C_6)$alkyl, —N$((C_1-C_6)$alkyl$)_2$, OH, OR$^A$, and halo (i.e., a halogen, for example chloro). $R^A$ represents a point of attachment to the interior surfaces of the fluidic system. At least one of $R^1$, $R^2$, $R^3$, $R^4$, $R^5$, and $R^6$ is OR$^A$. X is $(C_1-C_{20})$alkyl, —O[(CH$_2$)$_2$O]$_{1-20}$—, —$(C_1-C_{10})$[NH(CO)NH$(C_1-C_{10})$]$_{1-20}$—, or —$(C_1-C_{10})$[alkylphenyl$(C_1-C_{10})$alkyl]$_{1-20}$—.

When used in the context of a chemical formula, a hyphen ("-") indicates the point of attachment. For example, when X is —[$(C_1-C_{10})$alkylphenyl$(C_1-C_{10})$alkyl]$_{1-20}$—, that means that X is connected to SiR$^1$R$^2$R$^3$ via the $(C_1-C_{10})$alkyl and connected to SiR$^4$R$^5$R$^6$ via the other $(C_1-C_{10})$alkyl. This applies to the remaining variables.

In one aspect, X in Formula I is $(C_1-C_{15})$alkyl, $(C_1-C_{12})$alkyl, or $(C_1-C_{10})$alkyl. In some aspects, X in Formula I is methyl, ethyl, propyl, isopropyl, butyl, sec-butyl, iso-butyl, t-butyl, pentyl, hexyl, heptyl, nonyl, or decanyl. In other aspect, X in Formula I is ethyl or decanyl.

In one aspect, at least one of $R^1$, $R^2$, $R^3$, $R^4$, $R^5$, and $R^6$ is $(C_1-C_6)$alkoxy, e.g., ethoxy, wherein the values for X are described in Formula I or the preceding paragraph. In another aspect, at least two of $R^1$, $R^2$, $R^3$, $R^4$, $R^5$, and $R^6$ is $(C_1-C_6)$alkoxy, e.g., ethoxy, wherein the values for X are described in Formula I or the preceding paragraph. In another aspect, at least three of $R^1$, $R^2$, $R^3$, $R^4$, $R^5$, and $R^6$ is $(C_1-C_6)$alkoxy, e.g., ethoxy, wherein the values for X are described in Formula I or the preceding paragraph. In another aspect, at least four of $R^1$, $R^2$, $R^3$, $R^4$, $R^5$, and $R^6$ is $(C_1-C_6)$alkoxy, e.g., ethoxy, wherein the values for X are described in Formula I or the preceding paragraph. In another aspect, at least five of $R^1$, $R^2$, $R^3$, $R^4$, $R^5$, and $R^6$ is $(C_1-C_6)$alkoxy, e.g., ethoxy, wherein the values for X are described in Formula I or the preceding paragraph.

In one aspect, at least one of $R^1$, $R^2$, $R^3$, $R^4$, $R^5$, and $R^6$ is halo, e.g., chloro, wherein the values for X are described in Formula I or the preceding paragraphs above. In another aspect, at least two of $R^1$, $R^2$, $R^3$, $R^4$, $R^5$, and $R^6$ is halo, e.g., chloro, wherein the values for X are described in Formula I or the preceding paragraphs above. In another aspect, at least three of $R^1$, $R^2$, $R^3$, $R^4$, $R^5$, and $R^6$ is halo, e.g., chloro, wherein the values for X are described in Formula I or the preceding paragraphs above. In another aspect, at least four of $R^1$, $R^2$, $R^3$, $R^4$, $R^5$, and $R^6$ is halo, e.g., chloro, wherein the values for X are described in Formula I or the preceding paragraphs above. In another aspect, at least five of $R^1$, $R^2$, $R^3$, $R^4$, $R^5$, and $R^6$ is halo, e.g., chloro, wherein the values for X are described in Formula I or the preceding paragraphs above.

In another aspect, $R^1$, $R^2$, $R^3$, $R^4$, $R^5$, and $R^6$ are each methoxy or chloro.

In some embodiments, the alkylsilyl coating of Formula I is a organosilica coating. In certain embodiments, the alkylsilyl coating of Formula I is a hybrid inorganic/organic material that forms the wetted surface or that coats the wetted surfaces.

The alkylsilyl coating of Formula I can have a contact angle of at least about 15°. In some embodiments, the alkylsilyl coating of Formula I can have a contact angle of less than or equal to 30°. The contact angle can be less than or equal to about 90°. In some embodiments, the contact angle of the alkylsilyl coating of Formula I is between about 15° to about 115°. For example, the contact angle of the alkylsilyl coating of Formula I can be about 0°, 5°, 10°, 15°, 20°, 25°, 30°, 35°, 40°, 45°, 50°, 55°, 60°, 65°, 70°, 75°, 80°, 85°, 90°, 95°, 100°, 105°, 110° or 115°.

The thickness of the alkylsilyl coating can be at least about 100 Å. For example, the thickness can be between about 100 Å to about 1600 Å. The thickness of the alkylsilyl coating for Formula I can be about 100 Å, 200 Å, 300 Å, 400 Å, 500 Å, 600 Å, 700 Å, 800 Å, 900 Å, 1000 Å, 1100 Å, 1200 Å, 1300 Å, 1400 Å, 1500 Å or 1600 Å. The thickness of the alkylsilyl coating (e.g., a vapor deposited alkylsilyl coating) can be detected optically by the naked eye. For example, more opaqueness and coloration is indicative of a thicker coating. Thus, coatings with pronounced visual distinction are an embodiment of this technology. From thin to thick, the color changes from yellow, to violet, to blue, to slightly greenish and then back to yellow when coated parts are observed under full-spectrum light, such as sunlight. For example, when the alkylsilyl coating is 300 Å thick, the coating can appear yellow and reflect light with a peak wavelength between 560 and 590 nm. When the alkylsilyl coating is 600 Å thick, the coating can appear violet and reflect light with a peak wavelength between 400 and 450 nm. When the alkylsilyl coating is 1000 Å thick, the coating can appear blue and reflect light with a peak wavelength between 450 and 490 nm. See, e.g., Faucheu et al., *Relating Gloss Loss to Topographical Features of a PVDF Coating*, Published Oct. 6, 2004; Bohlin, Erik, *Surface and Porous*

Structure of Pigment Coatings, Interactions with flexographic ink and effects of print quality, Dissertation, Karlstad University Studies, 2013:49.

In one aspect, the vapor deposited coating of Formula I is the product of vapor deposited bis(trichlorosilyl)ethane, bis(trimethoxysilyl)ethane, bis(trichlorosilyl)octane, bis(trimethoxysilyl)octane, bis(trimethoxysilyl)hexane, and bis(trichlorosilyl)hexane.

In some aspects, at least a portion of the wetted surfaces are coated with multiple layers of the same or different alkylsilyls, where the thickness of the alkylsilyl coatings correlate with the number of layering steps performed (e.g., the number of deposited layers of alkylsilyl coating on wetted surfaces (e.g., internal surfaces of the fluidic flow path of the chromatographic system/device or internal surfaces or fluid interfacing/contacting surfaces of labware or other analytical devices, such as frits within a solid phase extraction device together with interior walls of the solid phase extraction device). In this manner, increasingly thick bioinert coatings can be produced and tailored to achieve desirable separations.

The chromatographic device can have a second alkylsilyl coating in direct contact with the alkylsilyl coating of Formula I. The second alkylsilyl coating has the Formula II

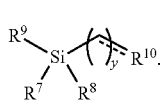

(II)

wherein $R^7$, $R^8$, and $R^9$ are each independently selected from —NH($C_1$-$C_6$)alkyl, —N[($C_1$-$C_6$)alkyl]$_2$, ($C_1$-$C_6$)alkoxy, ($C_1$-$C_6$)alkyl, ($C_1$-$C_6$)alkenyl, OH, and halo; $R^{10}$ is selected from ($C_1$-$C_6$)alkyl, —OR$^B$, —[O($C_1$-$C_3$)alkyl]$_{1-10}$O($C_1$-$C_6$)alkyl, —[O($C_1$-$C_3$)alkyl]$_{1-10}$OH and phenyl. ($C_1$-$C_6$)alkyl is optionally substituted with one or more halo. The phenyl is optionally substituted with one or more groups selected from ($C_1$-$C_3$)alkyl, hydroxyl, fluorine, chlorine, bromine, cyano, —C(O)NH$_2$, and carboxyl. $R^B$ is —($C_1$-$C_3$)alkyloxirane, —($C_1$-$C_3$)alkyl-3,4-epoxycyclohexyl, or —($C_1$-$C_4$)alkylOH. The hashed bond to $R^{10}$ represents an optional additional covalent bond between $R^{10}$ and the carbon bridging the silyl group to form an alkene, provided y is not 0. y is an integer from 0 to 20.

In one aspect, y in Formula II is an integer from 1 to 15. In another aspect, y in Formula II is an integer from 1 to 12. In another aspect, y in Formula II is an integer from 1 to 10. In another aspect, y in Formula II is an integer from 2 to 9.

In one aspect $R^{10}$ in Formula II is methyl and y is as described above for Formula II or the preceding paragraph.

In one aspect, $R^7$, $R^8$, and $R^9$ in Formula II are each the same, wherein $R^{10}$ and y are as described above. In one aspect, $R^7$, $R^8$, and $R^9$ are each halo (e.g., chloro) or ($C_1$-$C_6$)alkoxy such as methoxy, wherein $R^{10}$ and y are as described above.

In one aspect, y in Formula II is 9, $R^{10}$ is methyl, and $R^7$, $R^8$, and $R^9$ are each ethoxy or chloro.

In one aspect, the coating of the formula II is n-decyltrichlorosilane, (3-glycidyloxypropyl)trimethoxysilane (GPTMS), (3-glycidyloxypropyl)trimethoxysilane (GPTMS) followed by hydrolysis, 2-(3,4-epoxycyclohexyl) ethyltrimethoxysilane, trimethylchlorosilane, trimethyldimethyaminosilane, methoxy-polyethyleneoxy(3)silane propyltrichlorosilane, propyltrimethoxysilane, (heptadecafluoro-1,1,2,2-tetrahydrodecyl)tris(dimethylamino)silane, (heptadecafluoro-1,1,2,2-tetrahydrodecyl)trischlorosilane, (heptadecafluoro-1,1,2,2-tetrahydrodecyl)trimethoxysilane vinyltrichlorosilane, vinyltrimethoxysilane, allyltrichlorosilane, 2-[methoxy(polyethyleneoxy)3propyl]trichlorosilane, 2-[methoxy(polyethyleneoxy)3propyl]trimethoxysilane, or 2-[methoxy(polyethyleneoxy)3propyl]tris(dimethylamino) silane.

The alkylsilyl coating of Formula I and II can have a contact angle of at least about 15°. In some embodiments, the alkylsilyl coating of Formula I and II can have a contact angle of less than or equal to 105°. The contact angle can be less than or equal to about 90°. In some embodiments, the contact angle of the alkylsilyl coating of Formula I and II is between about 15° to about 105°. For example, the contact angle of the alkylsilyl coating of Formula I and II can be about 0°, 5°, 10°, 15°, 20°, 25°, 30°, 35°, 40°, 45°, 50°, 55°, 60°, 65°, 70°, 75°, 80°, 85°, 90°, 95°, 100°, 105°, 110° or 115°.

The thickness of the multi-layered alkylsilyl coating can be at least about 100 Å. For example, the thickness can be between about 100 Å to about 1600 Å. The thickness of the multi-layered alkylsilyl coating for Formal I can be about 100 Å, 200 Å, 300 Å, 400 Å, 500 Å, 600 Å, 700 Å, 800 Å, 900 Å, 1000 Å, 1100 Å, 1200 Å, 1300 Å, 1400 Å, 1500 Å or 1600 Å.

In one aspect, the alkylsilyl coating of Formula I is bis(trichlorosilyl)ethane or bis(trimethoxysilyl)ethane and the alkylsilyl coating of Formula II is (3-glycidyloxypropyl)trimethoxysilane. In another aspect, the alkylsilyl coating of Formula I is bis(trichlorosilyl)ethane or bis(trimethoxysilyl)ethane and the alkylsilyl coating of Formula II is (3-glycidyloxypropyl)trimethoxysilane followed by hydrolysis. In one aspect, the alkylsilyl coating of Formula I is bis(trichlorosilyl)ethane or bis(trimethoxysilyl)ethane and the alkylsilyl coating of Formula II is n-decyltrichlorosilane. The alkylsilyl coating of Formula I can be bis(trichlorosilyl)ethane or bis(trimethoxysilyl)ethane and the alkylsilyl coating of Formula II can be trimethylchlorosilane or trimethyldimethyaminosilane. In one aspect, the alkylsilyl coating of Formula I is bis(trichlorosilyl)ethane or bis(trimethoxysilyl)ethane and the alkylsilyl coating of Formula II is methoxy-polyethyleneoxy(3) propyl tricholorosilane or methoxy-polyethyleneoxy(3) propyl trimethoxysilane.

The chromatographic device can have an alkylsilyl coating in direct contact with the alkylsilyl coating of Formula III in direct contact with the alkylsilyl coating of Formula I.

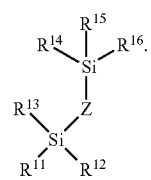

(III)

$R^{11}$, $R^{12}$, $R^{13}$, $R^{14}$, $R^{15}$, and $R^{16}$ are each independently selected from ($C_1$-$C_6$)alkoxy, —NH($C_1$-$C_6$)alkyl, —N(($C_1$-$C_6$)alkyl)$_2$, OH, and halo (i.e., a halogen, for example, chloro). Z is ($C_1$-$C_{20}$)alkyl, —O[($CH_2$)$_2$O]$_{1-20}$—, —($C_1$-$C_{10}$)[NH(CO)NH($C_1$-$C_{10}$)]$_{1-20}$—, or —($C_1$-$C_{10}$)[alkylphenyl($C_1$-$C_{10}$)alkyl]$_{1-20}$-.

In some aspects, Z in Formula III is ($C_1$-$C_{10}$)alkyl; and $R^1$, $R^2$, $R^3$, $R^4$, $R^5$, and $R^6$ are each methoxy or chloro. In other aspects, Z in Formula III is ($C_2$-$C_{10}$)alkyl. In other aspects, Z in Formula III is ethyl.

In the layered alkylsilyl coating of Formula I and Formula III, Formula I and Formula III can be the same (for example, $C_2C_2$) or Formula I and Formula III can be different. Formula III is attached directly to the coating of Formula I, i.e., in Formula III, there is no point of attachment to the interior of the fluidic system; instead Formula III is deposited directly on Formula I.

The alkylsilyl coating of Formula III can be bis(trichlorosilyl)ethane or bis(trimethoxysilyl)ethane. The alkylsilyl coating of Formula I can be bis(trichlorosilyl)ethane or bis(trimethoxysilyl)ethane and the alkylsilyl coating of Formula III can be bis(trichlorosilyl)ethane or bis(trimethoxysilyl)ethane.

The alkylsilyl coating of Formula I and III can have a contact angle of at least about 15°. In some embodiments, the alkylsilyl coating of Formula I and III can have a contact angle of less than or equal to 105°. The contact angle can be less than or equal to about 90°. In some embodiments, the contact angle of the alkylsilyl coating of Formula I and III is between about 15° to about 115°. For example, the contact angle of the alkylsilyl coating of Formula I and III can be about 0°, 5°, 10°, 15°, 20°, 25°, 30°, 35°, 40°, 45°, 50°, 55°, 60°, 65°, 70°, 75°, 80°, 85°, 90°, 95°, 100°, 105° or 115°.

The thickness of the multi-layered alkylsilyl coating can be at least about 100 Å. For example, the thickness can be between about 100 Å to about 1600 Å. The thickness of the multi-layered alkylsilyl coating for Formal I can be about 100 Å, 200 Å, 300 Å, 400 Å, 500 Å, 600 Å, 700 Å, 800 Å, 900 Å, 1000 Å, 1100 Å, 1200 Å, 1300 Å, 1400 Å, 1500 Å or 1600 Å.

In one aspect, the alkylsilyl coating of Formula II is applied directly to wetted surfaces of the fluidic flow path. Therefore, in some embodiments, one of $R^7$, $R^8$, and $R^9$ of Formula II can also include $OR^A$, where $R^A$ represents a point of attachment to the interior surfaces (e.g., wetted surfaces) of the fluidic system. In other embodiments, $R^7$, $R^8$, and $R^9$ of the alkylsilyl coating of Formula II does not include $OR^A$, by the alkylsilyl coating of Formula II is deposited directly onto wetted surfaces of the fluidic flow path that have been pre-treated with, for example, a plasma.

In one aspect, stainless steel flow path components, including but not limited to tubing, microfabricated fluid conduits, column frits, column inlet tubing, and sample injection needles, are coated via vapor deposition with one or more of the disclosed alkylsilyls. In one aspect, these coated components are annealed to alter their chemical or physical properties.

In another aspect, flow path components that are made of other materials than stainless steel or other metallics, (e.g., polymers, glass, etc.) are coated via vapor deposition with one or more of the disclosed alkylsilyls. In particular, frits for use within the chromatography or fluid injection system or sample vials connectable to the injection needle are coated.

In another aspect, wetted surfaces of labware or at least some portion of wetted surfaces of labware are coated via vapor deposition with one or more of the disclosed alkylsilyls. In certain embodiments, the vapor deposited coatings are used to minimize adsorptive losses of the sample. In some embodiments, the vapor deposited coating is both neutral (low in ionic properties) and hydrophilic (exhibiting a contact angle less than 60°). The coating can be used to mitigate issues with many different types of materials, including glass and polymeric compositions, such as polypropylene or polyethylene.

Exemplary coatings with their respective approximate thickness and contact angle are provided in Table 1.

TABLE 1

| VPD# | Vapor Deposited Material | Alternative Coating Abbreviation | Approximate Thickness of Product | Approximate Contact Angle |
|---|---|---|---|---|
| 1 | bis(trichlorosilyl)ethane or bis(trismethoxysilyl)ethane as a first layer followed by GPTMS followed by hydrolysis to form GPTMS-OH | $C_2$-GPTMS-OH | 500 Å | 15° |
| 2 | bis(trichlorosilyl)ethane or bis(trimethoxysilyl)ethane | $C_2$ | 500 Å | 35° |
| 3 | bis(trichlorosilyl)ethane or bis(trimethoxysilyl)ethane as a first layer followed by bis(trichlorosilyl)ethane or bis(trimethoxysilyl)ethane as a second layer. | $C_2$-$C_2$ | 1600 Å | 35° |
| 4 | bis(trichlorosilyl)ethane or bis(trimethoxysilyl)ethane as a first layer followed by GPTMS as a second layer | $C_2$-GPTMS | 500 Å | 50° |
| 5 | Annealed bis(trichlorosilyl)ethane or bis(trimethoxysilyl)ethane | Annealed $C_2$ | 500 Å | 95° |
| 6 | Annealed bis(trichlorosilyl)ethane or bis(trimethoxysilyl)ethane as a first layer followed by annealed bis(trichlorosilyl)ethane or bis(trimethoxysilyl)ethane as a second layer | Annealed $C_2$-$C_2$ | 1600 Å | 95° |
| 7 | bis(trichlorosilyl)ethane or bis(trimethoxysilyl)ethane as a first layer followed by n-decyltrichlorosilane as a second layer | $C_2C_{10}$ | 500 Å | 105° |

TABLE 1-continued

| VPD# | Vapor Deposited Material | Alternative Coating Abbreviation | Approximate Thickness of Product | Approximate Contact Angle |
|---|---|---|---|---|
| 8 | Annealed bis(trichlorosilyl)ethane or bis(trimethoxysilyl)ethane as a first layer followed by annealed n-decyltrichlorosilane as a second layer | Annealed $C_2C_{10}$ | 500 Å | 105° |
| 9 | GPTMS | GPTMS | 100 to 200 Å | ~50° |
| 10 | GPTMS followed by hydrolysis to form GPTMS-OH | GPTMS-OH | 100 to 200 Å | ~20° |
| 11 | bis(trichlorosilyl)ethane or bis(trimethoxysilyl)ethane as a first layer followed by trimethylchlorosilane or trimethyldimethylaminosilane | $C_2C_3$ | 500 Å | 40-90° |
| 12 | annealed bis(trichlorosilyl)ethane or bis(trimethoxysilyl)ethane as a first layer followed by trimethylchlorosilane or trimethyldimethylaminosilane | Annealed $C_2C_3$ | 500 Å | 95° |
| 13 | bis(trichlorosilyl)ethane or bis(trimethoxysilyl)ethane as a first layer followed by a methoxy-polyethyleneoxy(3) propyl trichlorosilane or methoxy-polyethyleneoxy(3) propyl trimethoxysilane | $C_2PEO$ | 500 Å | 15° |

Referring to VPD #1 ($C_2$-GPTMS-OH), the first coating layer, $C_2$ shown below, is a layer according to Formula I, described above.

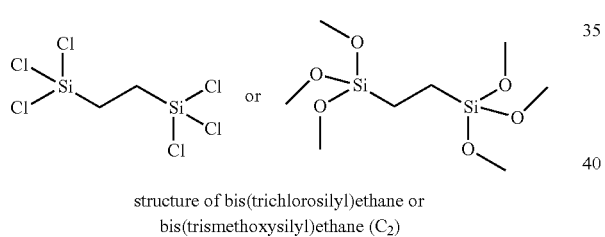

structure of bis(trichlorosilyl)ethane or bis(trismethoxysilyl)ethane ($C_2$)

The second layer of VPD #1, GPTMS-OH, shown below, is a layer according to Formula II.

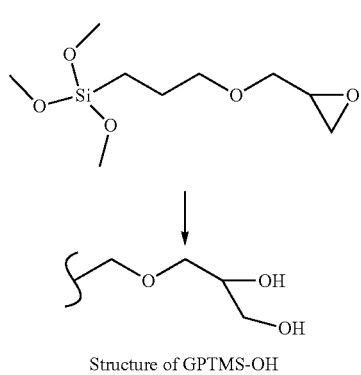

Structure of GPTMS-OH

VPD #3 ($C_2$-$C_2$) is an example of a coating of Formula I and then a coating for Formula III.

VPD #7 ($C_2C_{10}$) is another example of a coating of Formula I and a second layer of Formula II. The structure of bis(trichlorosilyl)ethane or bis(trismethoxysilyl)ethane ($C_2$) is shown above. The structure of $C_{10}$ is shown below.

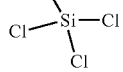

Structure of n-decyltrichlorosilane ($C_{10}$)

VPD #11 ($C_2C_3$) is another example of a coating of Formula I and a second layer of Formula II. The structure of bis(trichlorosilyl)ethane or bis(trismethoxysilyl)ethane ($C_2$) is shown above. The structure of $C_3$ is shown below.

Structure of trimethylchlorosilane or trimethyldimethylaminosilane ($C_3$)

VPD #13 is another example of a coating of Formula I and a second layer of Formula II. The structure of bis(trichlorosilyl)ethane or bis(trismethoxysilyl)ethane ($C_2$) is shown above. The structure of methoxy-polyethyleneoxy(3)propyl trichlorosilane (PEO) is shown below.

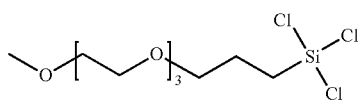

Structure of methoxy-polyethyleneoxy(3)propyl trichlorosilane (PEO)

Alternatively, commercially available vapor deposition coatings can be used in the disclosed systems, devices, and methods, including but not limited to Dursan® and Dursox® (commercially available from SilcoTek Corporation, Bellefonte, Pa.).

In one aspect, the alkylsilyl coatings described herein enhance the corrosion performance of metals, e.g., as in metallic chromatography columns. Depending on the denseness and thickness, the coatings act as a barrier, thereby preventing water and corrosive molecules from reacting with the base metal. While increasing the hydrophobicity and density improves the corrosion performance, even coatings derived from $C_2$ and GPTMS ($C_2$-GPTMS) followed by hydrolysis to form $C_2$-GPTMS-OH shows a 10x improvement in the ASTM G48 Method A pitting corrosion, see e.g., Example 4 below. In terms of most corrosion resistant to least, the ranking is the material formed from VPD #7>2>1 (bis(trichlorosilyl)ethane or bis(trimethoxysilyl)ethane as a first layer followed by GPTMS then hydrolysis to form GPTMS-OH as a second layer). This also correlates to hydrophobicity rankings.

Methods of Tailoring a Fluidic Flow Path

The coatings described above can be used to tailor a fluidic flow path of a chromatography system for the separation of a sample. The coatings can be vapor deposited. In general, the deposited coatings can be used to adjust the hydrophobicity of internal surfaces of the fluidic flow path that come into contact with a fluid (i.e. wetted surfaces or surfaces coming into contact with the mobile phase and/or sample/analyte). By coating wetted surfaces of one or more components of a flow path within a chromatography system, a user can tailor the wetted surfaces to provide a desired interaction (or lack of interaction) between the flow path and fluids therein (including any sample, such as biomolecules, proteins, glycans, peptides, oligonucleotides, pesticides, bisphosphonic acids, anionic metabolites, and zwitterions like amino acids and neurotransmitters, within the fluid). The wetted surfaces need not be within a chromatography system. Other devices or labware can also be tailored. That is, any fluid contacting surface, such as frits within an extraction device, or the interior of a pipette tip, can be tailored to provide the desired interaction or lack of interaction between the wetted surfaces and fluids therein.

In one aspect, an effective coating is produced from a low temperature, vacuum-assisted vapor deposition process. In one aspect, an oxygen plasma pretreatment step precedes the coating deposition. The oxygen plasma removes organic compounds and improves surface wettability for the coatings. Time, temperature, and pressure are controlled for each processing step. Each coating run can use a silicon wafer to monitor the thickness and contact angle of the resultant coating. Ellipsometry can be used to measure the coating thickness, and an optical goniometer can be used to measure the contact angle of the coating. A post coating annealing step can be utilized to increase coating cross-linking and increase coating hydrophobicity.

Figure 2:
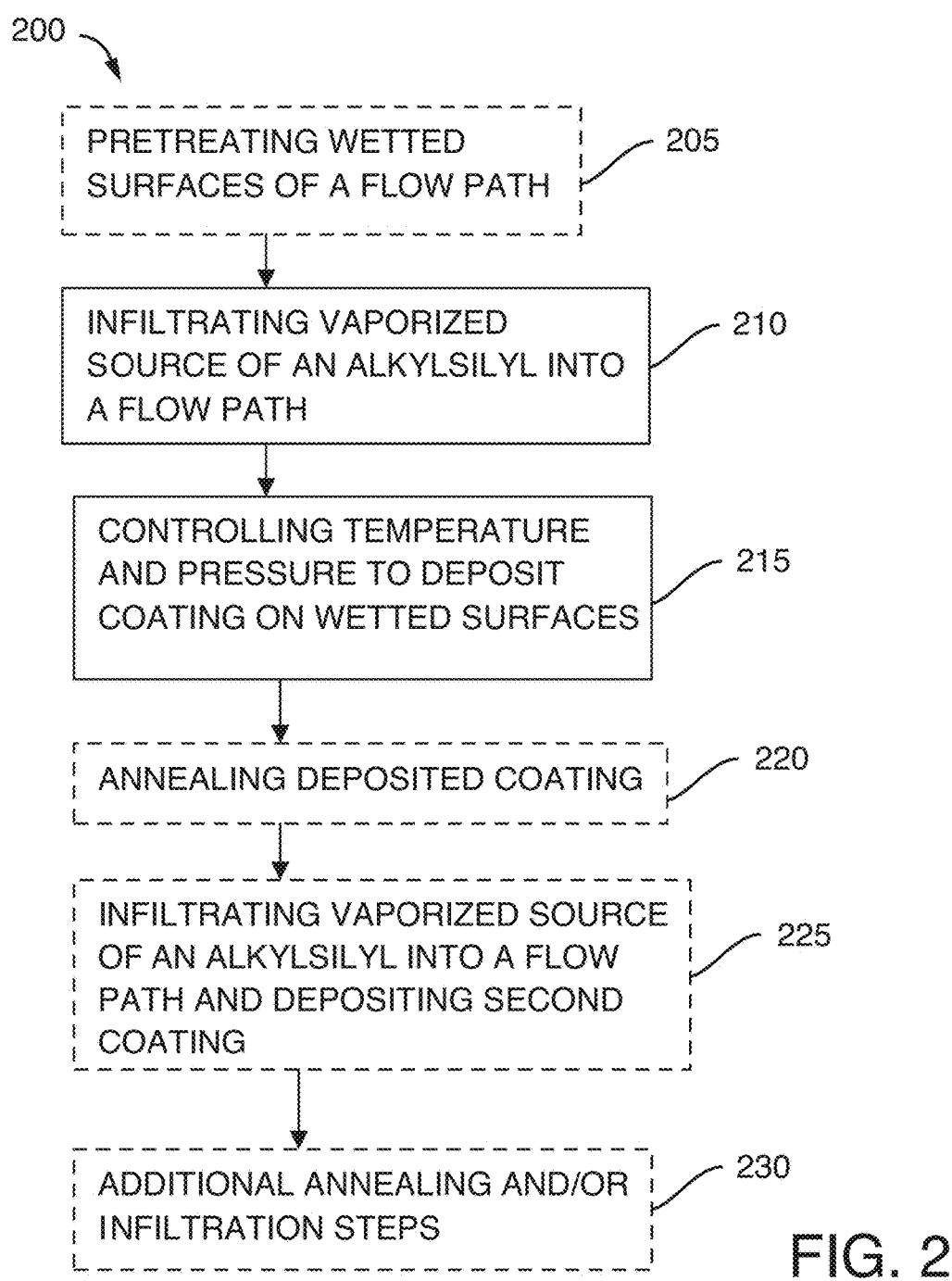
FIG. 2 is a flow chart showing a method of tailoring wetted surfaces of a flow path, in accordance with an illustrative embodiment of the technology.

FIG. 2 is a flow chart illustrating method 200 for tailoring a fluidic flow path for separation of a sample including biomolecules, proteins, glycans, peptides, oligonucleotides, pesticides, bisphosphonic acids, anionic metabolites, and zwitterions like amino acids and neurotransmitters. The method has certain steps which are optional as indicated by the dashed outline surrounding a particular step. Method 200 can start with a pretreatment step (205) for cleaning and/or preparing a flow path within a component for tailoring. Pretreatment step 205 can include cleaning the flow path with plasma, such as oxygen plasma. This pretreatment step is optional.

Next, an infiltration step (210) is initiated. A vaporized source of an alkylsilyl compound (e.g., the alkylsilyl compounds of Formulas I, II and/or III) is infiltrated into the flow path to coat the wetted surfaces. The vaporized source is free to travel throughout and along the internal surfaces of the flow path. Temperature and/or pressure is controlled during infiltration such that the vaporized source is allowed to permeate throughout the internal flow path and to deposit a coating from the vaporized source on the exposed surface (e.g., wetted surfaces) of the flow path as shown in step 215. Additional steps can be taken to further tailor the flow path. For example, after the coating is deposited, it can be heat treated or annealed (step 220) to create cross linking within the deposited coating and/or to adjust the contact angle or hydrophobicity of the coating. Additionally or alternatively, a second coating of alkylsilyl compound (having the same or different form) can be deposited by infiltrating a vaporized source into the flow path and depositing a second or additional layers in contact with the first deposited layer as shown in step 225. After the deposition of each coating layer, an annealing step can occur. Numerous infiltration and annealing steps can be provided to tailor the flow path accordingly (step 230).

In some embodiments, coating the flow path includes uniformly distributing the coating about the flow path, such that the walls defining the flow path are entirely coated. In some embodiments, uniformly distributing the coating can provide a uniform thickness of the coating about the flow path. In general, the coating uniformly covers the wetted surfaces such that there are no "bare" or uncoated spots.

Figure 3:
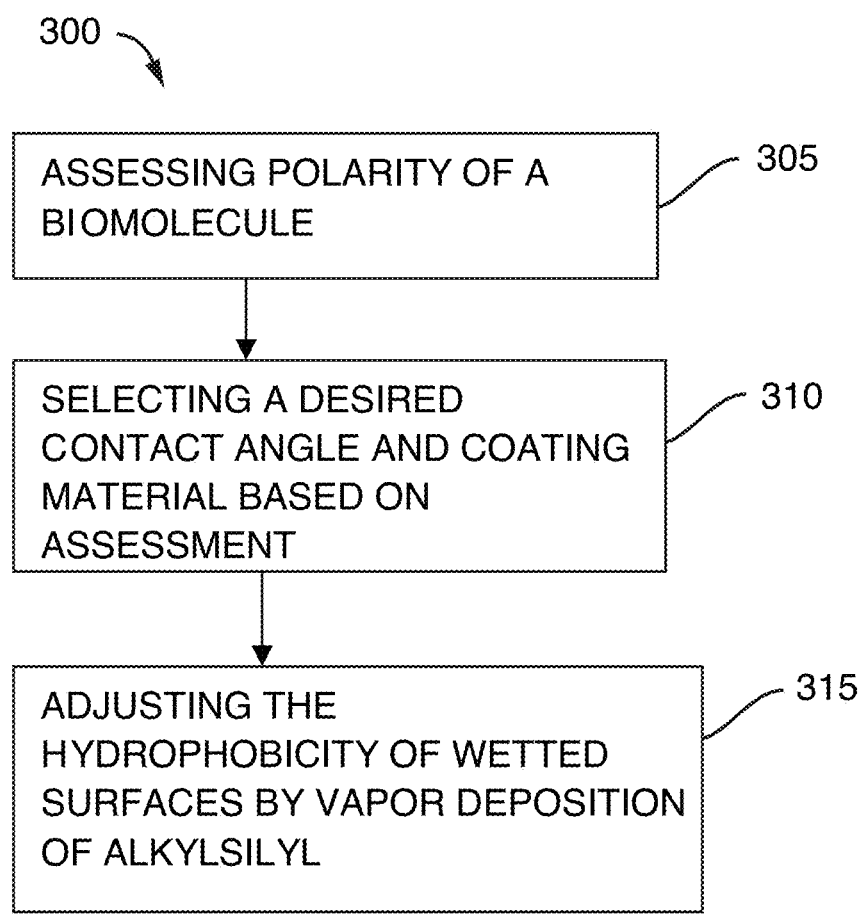
FIG. 3 is a flow chart showing a method of tailoring a fluidic flow path for separation of a sample including a biomolecule, in accordance with an illustrative embodiment of the technology.

FIG. 3 provides a flow chart illustrating a method (300) of tailoring a fluidic flow path for separation of a sample including a biomolecule or a metal interacting analyte. The method can be used to tailor a flow system for use in isolating, separating, and/or analyzing the biomolecule or metal interacting analyte. In step 305, the analyte is assessed to determine its polarity. Understanding the polarity will allow an operator to select (by either look up table or make a determination) a desired coating chemistry and, optionally, contact angle as shown in step 310. In some embodiments, in addition to assessing the polarity of the biomolecule or metal interacting analyte, the polarity of a stationary phase to be used to separate the biomolecule or metal interacting analyte (e.g., stationary phase to be included in at least a portion of the fluidic flow path) is also assessed. A chromatographic media can be selected based on the analyte in the sample. Understanding the polarity of both the analyte and the stationary phase is used in certain embodiments, by the operator to select the desired coating chemistry and contact angle in step 310. The components to be tailored can then be positioned within a chemical infiltration system with environmental control (e.g., pressure, atmosphere, temperature, etc.) and precursor materials are infiltrated into the flow path of the component to deposit one or more coatings along the wetted surfaces to adjust the hydrophobicity as shown in step 315. During any one of infiltration, deposition, and condition steps (e.g. annealing), coatings deposited from the infiltration system can be monitored and if necessary precursors and or depositing conditions can be adjusted if required allowing for fine tuning of coating properties. The alkylsilyl coating material selected in step 310 can be the alkylsilyl compounds of Formulas I, II and/or III.

A method of tailoring a fluidic flow path for separation of a sample is provided that includes assessing a polarity of an analyte in the sample and selecting a chromatographic media based on the analyte in the sample. An alkylsilyl coating is selected based on the polarity of the analyte in the sample. The alkylsilyl coating is selected so that the coating is inert to the analyte(s) being separated. In other words, the alkylsilyl coating does not produce any secondary chromatographic effects that are attributable to the alkylsilyl coating. In some embodiments, the analyte is a biomolecule. The biomolecule can be a peptide or peptide fragment, an oligopeptide, a protein, a glycan, a nucleic acid or nucleic acid fragment, a growth factor, a carbohydrate, a fatty acid or a lipid. The analyte can be a citric acid cycle metabolite. The analyte can be a pesticide.

A method of tailoring a fluidic flow path within a processing device includes assessing the hydrophobicity of an analyte within a fluid to be processed and of wetted surfaces of the processing device. An alkylsily coating is selected to minimize adsorptive losses to the wetted surfaces based on a difference in hydrophobicity of the analyte and the wetted surfaces of the processing device.

The alkylsilyl coating can have the Formula I, II, or III as described above. In one embodiment, the alkylsilyl coating has the Formula I as a first layer and Formula II as a second layer. In some embodiments, there is only a single layer coating having Formula I (e.g., bis(trichlorosilyl)ethane or bis(trimethoxysilyl)ethane). In some embodiments, there is only a single layer coating having Formula II (e.g., (3-glycidyloxypropyl)trimethoxysilane, n-decyltrichlorosilane, trimethylchlorosilane, trimethyldimethyaminosilane, or methoxy-polyethyleneoxy(3)silane). In some embodiments, there is only a single layer coating having Formula III (e.g., bis(trichlorosilyl)ethane or bis(trimethoxysilyl)eithane).

The method also includes adjusting a hydrophobicity of the wetted surfaces of the fluidic flow path by vapor depositing the alkylsilyl coating onto the wetted surfaces of the fluidic flow path. In some embodiments, the hydrophobicity of the wetted surfaces is adjusted by adjusting the contact angle of the alkylsilyl coating. For example, the contact angle of the alkylsilyl coating can be between about 0° to about 115°. In cases where the underlying material of the wetted surfaces is hydrophobic, alkylsilyl coatings that are hydrophilic (exhibiting a contact angle of less than about 60°) are preferred. In embodiments where the underlying material of the wetted surfaces is hydrophilic, and there is a preference to increase hydrophobicity, then a alkylsilyl coating exhibiting a contact angle of greater than 60° is vapor deposited.

The analyte in the sample can be retained with a retentivity within 10% of the retentivity attributable to the chromatography media. In some embodiments, the sample can be retained with a retentivity within 5% or within 1% of the retentivity attributable to the chromatography media. Therefore, the alkylsilyl coating solves the problem of metal interaction between the analyte and the metal chromatographic materials without introducing any secondary reactions that would have a negative effect on the quality of the separation. The alkylsilyl coating does not impart any retention mechanism on the analyte of interest, making the coating inert to the analyte of interest and low-bind.

In addition, the alkylsilyl coating does not produce any changes to peak width. The analyte in the sample has a peak width that is within 10%, 5%, or 1% of the peak width attributable to the chromatographic media.

The wetted surfaces of the fluidic flow path can be any of those described above with respect to aspects and embodiments of the chromatographic device.

The method can also include annealing the alkylsilyl coating after vapor depositing the alkylsilyl coating on the wetted surfaces of the fluidic flow path. Typically, the annealing cycle involves subjecting the coating to 200° C. for 3 hours under vacuum.

The method can also include assessing the polarity of the chromatographic media and selecting the alkylsilyl coating based on the polarity of the analyte and the chromatographic media. The method can also include eluting the sample through the fluidic flow path, thereby isolating the analyte.

In some embodiments, the alkylsilyl coating is modified with a silanizing reagent to obtain a desired thickness of the alkylsilyl coating. The silanizing reagent can be a non-volatile zwitterion. The non-volatile zwitterion can be sulfobetaine or carboxybetaine. In some embodiments, the silanizing reagent is an acidic or basic silane. The silanizing reagent can introduce polyethylene oxide moieties, such as methoxy-polyethyleneoxy(6-9)silane, the structure of which is shown below.

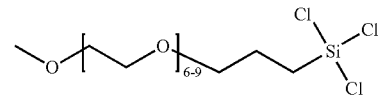

Structure of methoxy-polyethyleneoxy(6-9)silane

In some aspects, the method of tailoring a fluidic flow path for processing a sample including a biomolecule further comprises: pretreating the wetted surfaces of the flow path with a plasma prior to depositing the first coating. In other aspects, the method of tailoring a fluidic flow path for processing a sample including a metal interacting analyte further comprises annealing the first coating at a temperature to increase cross-linking in the first coating. In yet another aspect, the method of tailoring a fluidic flow path for separation of a sample including a metal interacting analyte further comprises annealing the first coating at a temperature to alter hydrophobicity.

In one aspect, the method of tailoring a fluidic flow path for separation of a sample including a metal interacting analyte further comprises performing a second infiltration with a vaporized source having the Formula II, wherein the features for Formula II are as described above; along and throughout the interior flow path of the fluidic system to form a second coating deposited in direct contact with the first coating. In one aspect, the step of performing a second infiltration in the preceding method further comprises performing an annealing step after depositing the second coating. In another aspect, the preceding method further comprises connecting in fluid communication with the flow path at least one coated component selected from the group consisting of a sample reservoir container and a frit.

Also provided herein is a method of tailoring a fluidic flow path for separation of a sample including a metal interacting analyte, the method comprising: assessing polarity of the analyte in the sample; selecting an alkylsilyl coating having the Formula I, wherein the features for Formula I are as described above, and desired contact angle based on polarity assessment; and adjusting the hydrophobicity of wetted surfaces of the flow path by vapor depositing an alkylsilyl having the Formula III, wherein the features for Formula III are as described above, and providing the desired contact angle. In some embodiments of the above method, in addition to assessing polarity of the analyte in the sample, the polarity of a stationary phase disposed within at least a portion of the flow path is also assessed and the polarity assessment is obtained from both the polarity of the biomolecule in the sample and the stationary phase.

Methods of Isolating an Analyte

In one aspect, provided herein are methods of isolating an analyte. The method includes introducing a sample including a glycan, a peptide, a pesticide, or a citric acid cycle metabolite into a fluidic system including a flow path disposed in an interior of the fluidic system. The flow path includes a first vapor deposited alkylsilyl inert coating having the Formula I described above and a second vapor deposited coating of the Formula II described above. The sample is eluted through the fluidic system, thereby isolating the glycan, peptide, pesticide, or citric acid cycle metabolite.

The glycan can be a phosphoglycan. The peptide can be a phosphopeptide and the pesticide can be glyphosate. The citric acid cycle metabolite can be citric acid or malic acid.

When the analyte is a glycan, peptide or pesticide, the alkylsilyl coating of Formula I can be bis(trichlorosilyl)ethane or bis(trimethoxysilyl)ethane and the alkylsilyl coating of Formula II can be n-decyltrichlorosilane. When the analyte is a citric acid cycle metabolite, the alkylsilyl coating of Formula I can be bis(trichlorosilyl)ethane or bis(trimethoxysilyl)ethane and the alkylsilyl coating of Formula II can be trimethylchlorosilane or trimethyldimethylaminosilane.

The flow path can be defined at least in part by the interior surface of a chromatographic system. The flow path can be further defined at least in part by passageways through a frit of the chromatographic column. The flow path can be defined at least in part by interior surfaces of tubing. The flow path can be any flow path described herein, for example, the flow paths described with respect to the chromatographic device.

Methods of Improving Baseline Returns

Also provided herein is a method of improving baseline returns in a chromatographic system, the method comprising: introducing a sample including an analyte into a fluidic system including a flow path disposed in an interior of the fluidic system, the flow path having a length to diameter ratio of at least 20 and comprising a vapor deposited alkylsilyl coating having the Formula I, wherein the features for Formula I are as described above, a thickness of at least 100 angstroms and a contact angle of about 30 degrees to 110 degrees; and eluting the sample through the fluidic system, thereby isolating the biomolecule. In some embodiments, the method includes a second layer of Formula II or Formula III, wherein the features of Formula II and II are described above.

Methods of Minimizing Adsorptive Losses

Also provided herein is a method of minimizing adsorptive losses, the method comprising: introducing a sample including an analyte into a processing device including a flow path disposed in an interior of the processing device, the flow path comprising a vapor deposited alkylsilyl coating having the Formula I, wherein the features for Formula I are as described above, a thickness of at least 100 angstroms and a contact angle of about 5 to 60°; and flowing the sample through the processing device. In some embodiments, the method includes a second layer of Formula II or Formula III, wherein the features of Formula II and II are described above.

Kits

Also provided here are kits. The kits include chromatographic components, for example, a chromatographic column, that has been coated with an alkylsilyl coating of Formulas I, II, and/or III, as described above. Other components can be provided in the kit that can also include the coatings described herein, for example, the tubing, frits, and/or connectors. The kit can also include instructions for separating analytes, for example, biomolecules, proteins, glycans, peptides, oligonucleotides, pesticides, bisphosphonic acids, anionic metabolites, and zwitterions like amino acids and neurotransmitters.

Embodiments may be directed to labware instead of chromatographic components. For example, the kit could include one or more of a beaker, extraction device, pipette tip, dialysis chamber, autosampler vial or plates that have been coated with an alkylsilyl coating of Formulas I, II, and/or III, as described above.

Exemplary Separations

Separation of Phosphoglygans

Figure 4C:
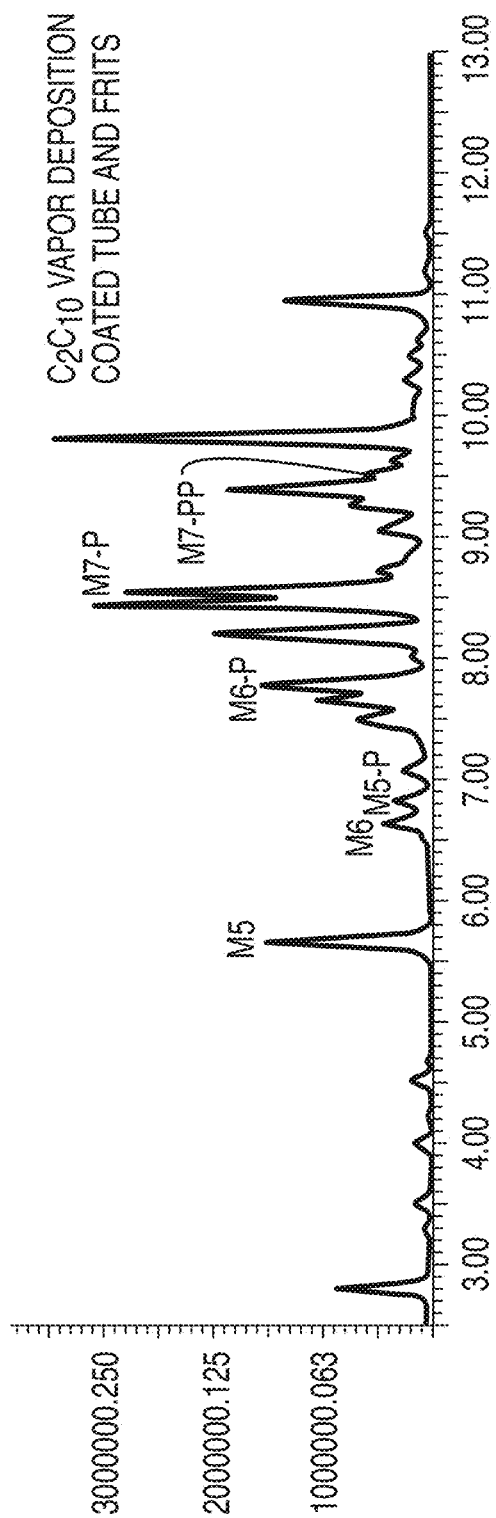
FIG. 4C shows a fluorescence chromatogram obtained using hardware coated with exemplary vapor deposited alkylsilyl, in accordance with an illustrative embodiment of the technology.

The disclosed coatings, which can be vapor deposited, have been found to dramatically improve separations of phosphoglycans by hydrophilic interaction chromatography (HILIC). To demonstrate the significance of this, the released N-glycans from a recombinant alpha-galactosidase which can be used as an enzyme replacement therapy for Fabry's disease were evaluated. This particular type of enzyme is taken up from circulation and delivered intercellularly to lysosomes through the mannose-6-phosphate pathway, making it important to identify and monitor the levels of phosphorylated glycans that are present on its surface. Vapor deposition coated stainless steel column tubes along with matching coated stainless steel frits were first tested against corresponding untreated stainless steel hardware. In this instance, two different types of coating chemistries were used. The coating chemistries used to coat the frits and tubing were VPD #2 and VPD #7. FIG. 4A-4C show fluorescence chromatograms obtained with these types of column hardware. From these data, it was found that use of coated column hardware significantly improved the recovery of each phosphorylated N-glycan species. For example, there was a marked increase in the peak area of Man7-PP, a high mannose glycan with two mannose-6-phosphate residues, mannose-7-bisphosphate. Where Man7-PP could not be detected with stainless steel column hardware, it was easily detected with vapor deposition coated column hardware. This indicated that this species of N-glycan was interacting with the metallic surfaces of the column hardware in such a way that prevented it from reaching the detector. When using vapor deposition coated hardware, the peak area ratio of Man-7-PP to Man5 (a high mannose glycan without phosphorylation) was 0.24:1 (FIG. 4A-4C).

Figure 5A:
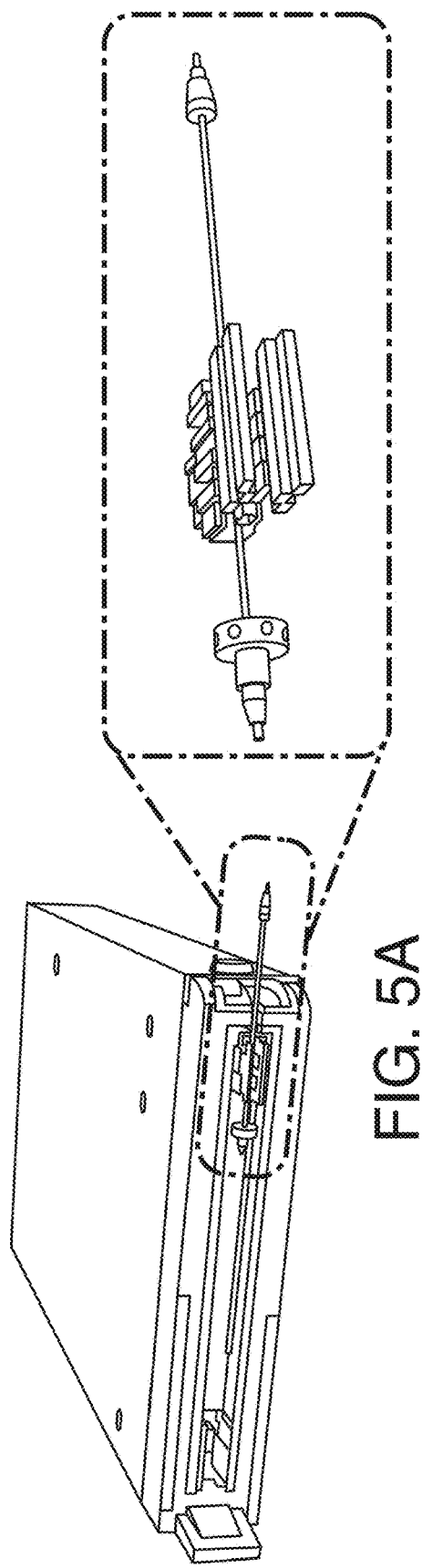
FIG. 5A is a schematic of exemplified bioinert alkylsilyl coated stainless steel sample flow path components, including column inlet tubing, in accordance with an illustrative embodiment of the technology.
Figure 5B:
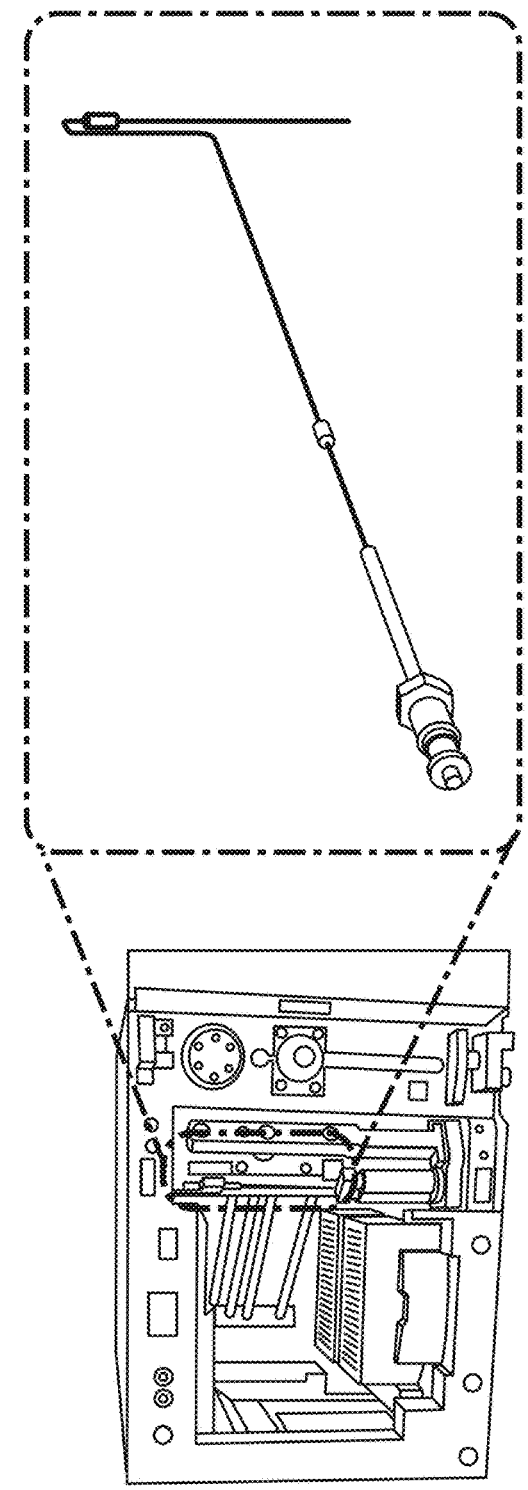
FIG. 5B is a schematic of exemplified bioinert alkylsilyl coated stainless steel sample flow path components, including a sample needle, in accordance with an illustrative embodiment of the technology.
Figure 6A:
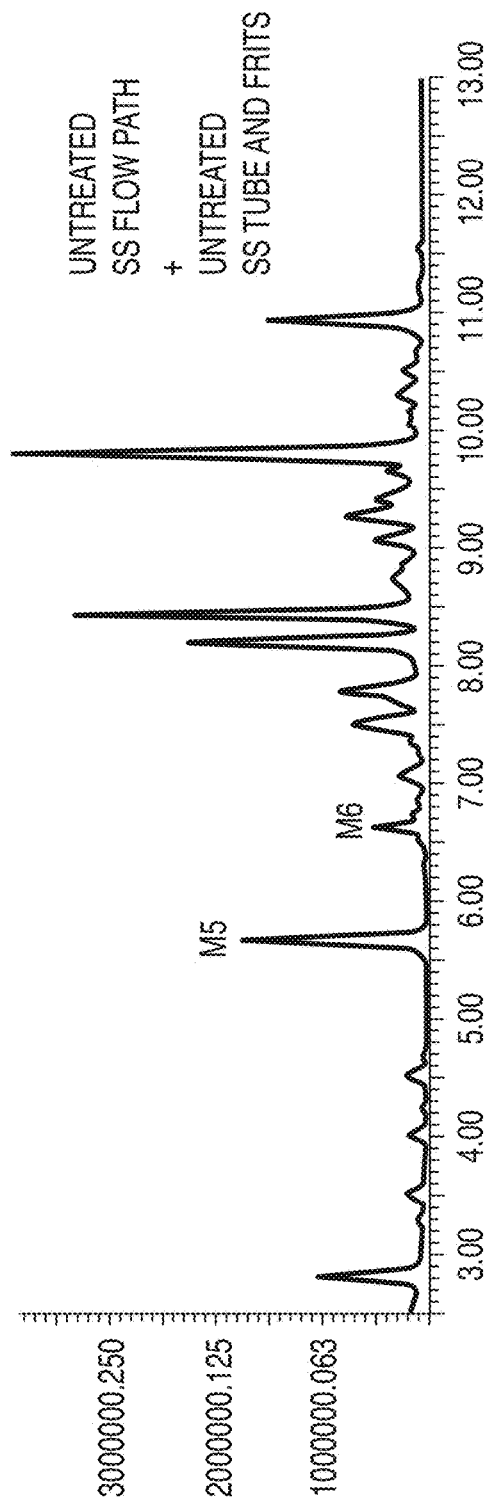
FIG. 6A shows a fluorescence chromatogram obtained using an untreated flow path and untreated tube and frit combination in accordance with an embodiment of the technology.
Figure 6B:
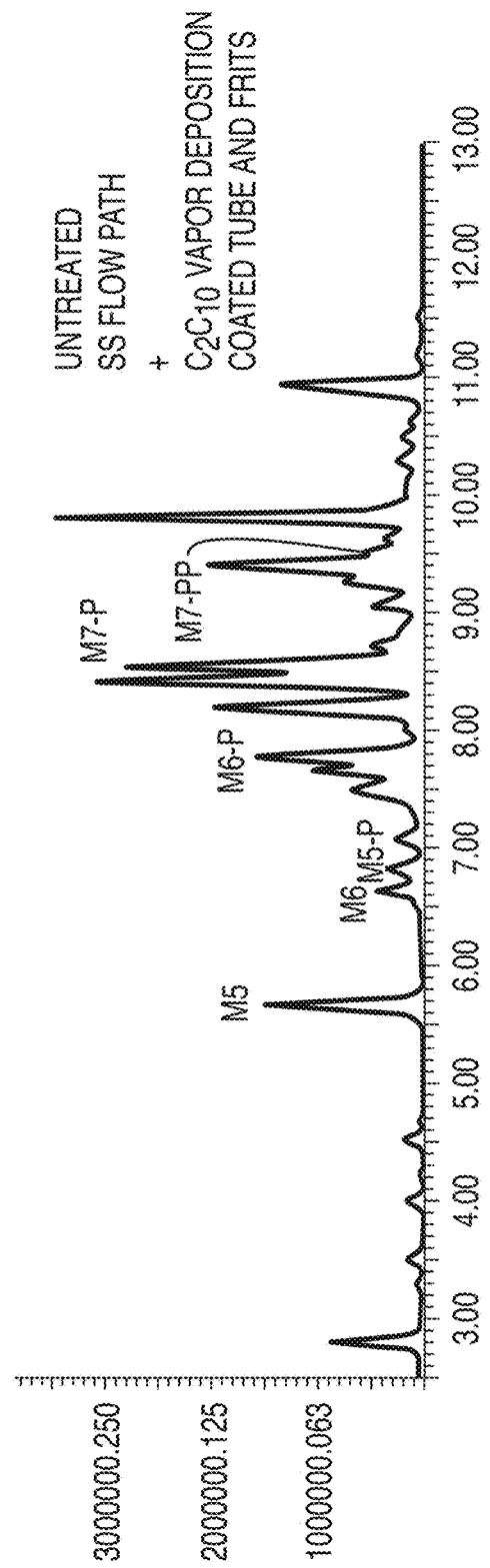
FIG. 6B shows a fluorescence chromatogram obtained using an untreated flow path and coated tube and frit combination, in accordance with an embodiment of the technology.
Figure 6C:
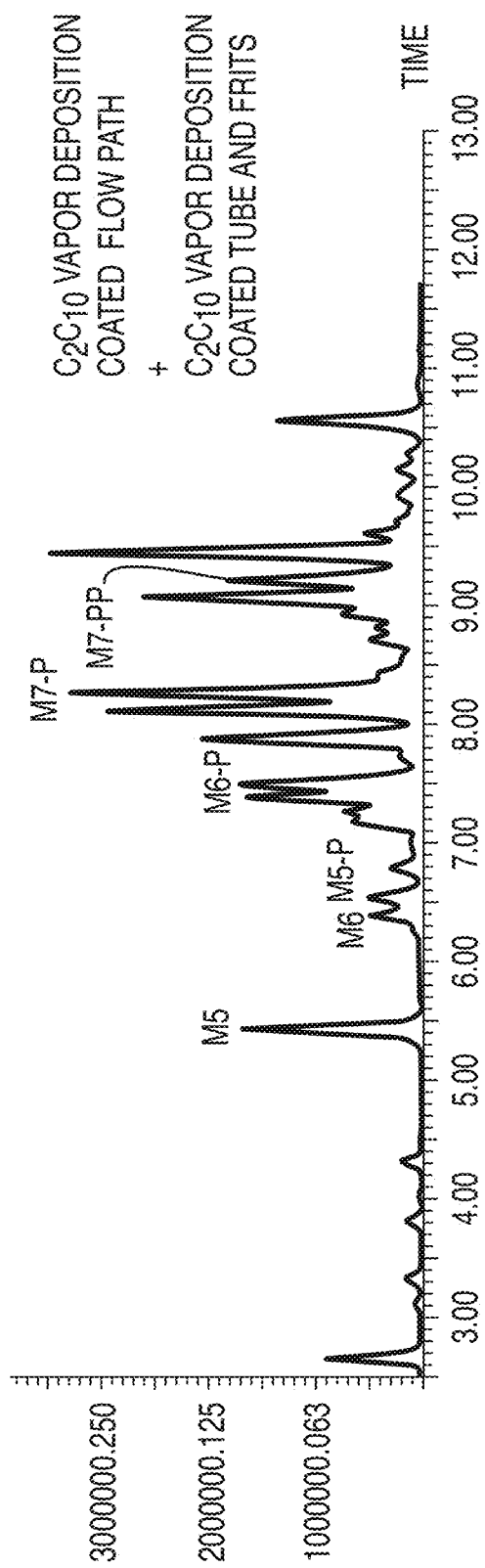
FIG. 6C shows a fluorescence chromatogram obtained using a coated flow path and coated tube and frit combination, in accordance with an embodiment of the technology.

The increased recovery of phosphorylated glycans using coated column hardware and fits shows that adsorption to metallic column hardware surfaces is detrimental to recovery. With this in mind, separations were also performed with vapor deposition coated stainless steel sample flow path components (FIGS. 5A and 5B). FIG. 6A-6C show fluorescence chromatograms obtained using coated LC system components in conjunction with coated stainless steel column hardware. Phosphoglycan recovery improved even more with the use of coated column hardware and $C_2C_{10}$ vapor deposition coated flow path components. Most notably, the peak area ratio of Man7-PP to ManS increased to 0.8:1 from the ratio of 0.24:1 that was obtained by using coated column hardware alone. The observed relative abundance for Man7-PP with the coated system and coated column hardware is indicative of full recovery for the phosphorylated glycans, as can be determined by orthogonal assays to HILIC of RapiFluor-MS labeled released glycans. In sum, these results confirm that the loss of phosphorylated N-glycan species to sample flow path surfaces can be alleviated with the use of vapor deposition coatings.

Separation of Other Phosphorylated Molecules

Figure 7A:
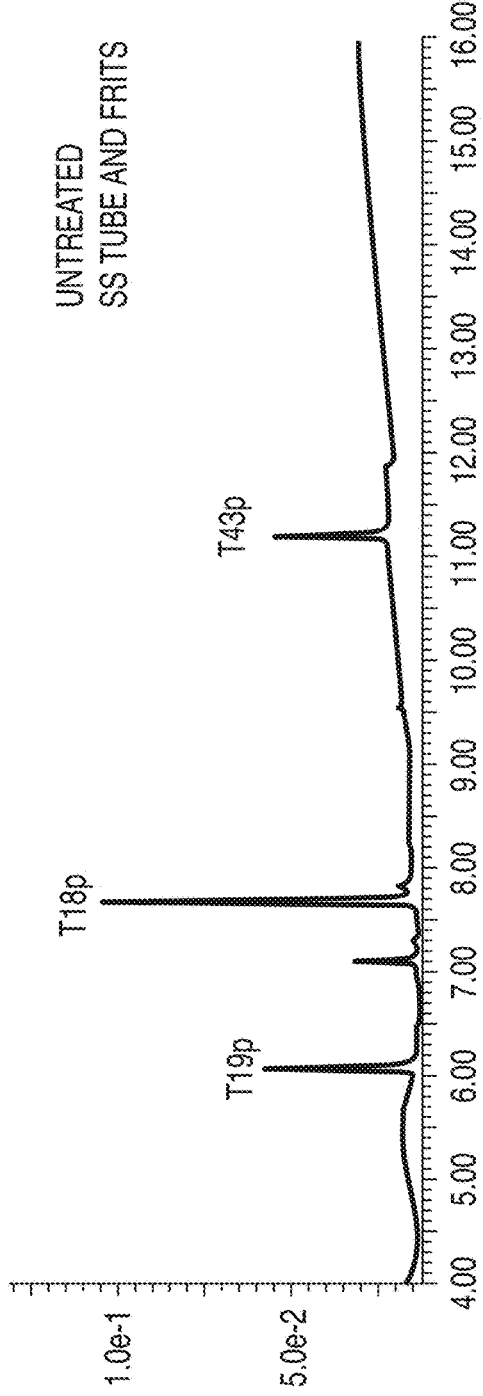
FIG. 7A shows a UV chromatogram obtained using an untreated stainless steel tube/frit combination in accordance with an embodiment of the technology.
Figure 7B:
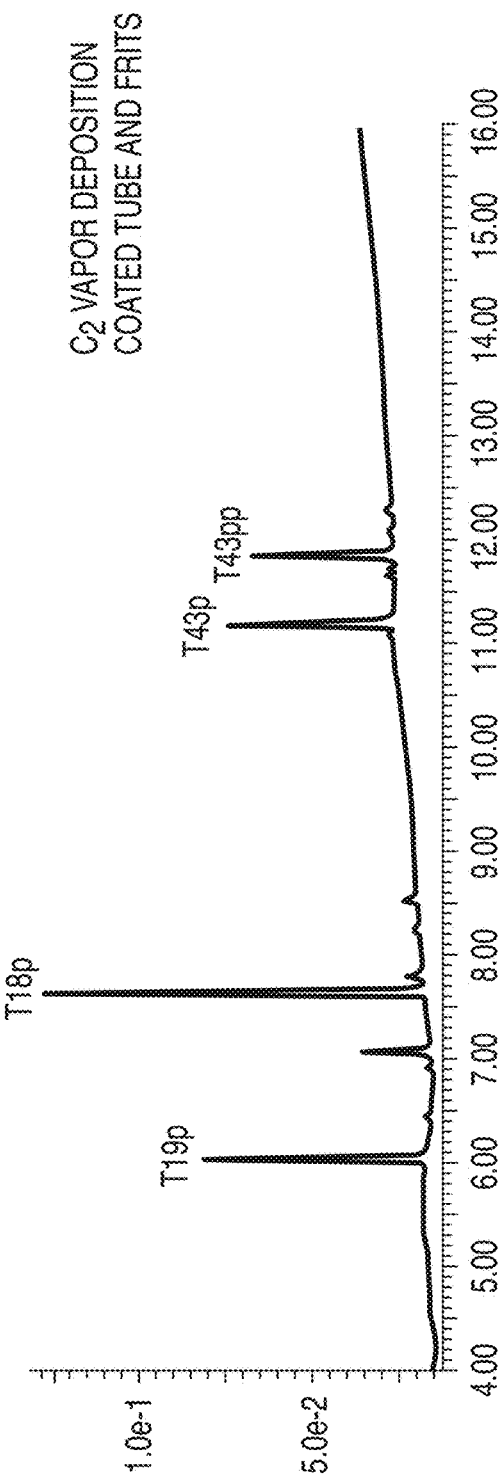
FIG. 7B shows a UV chromatogram obtained using a $C_2$ vapor deposition coated tube/frit combination, in accordance with an embodiment of the technology.
Figure 7C:
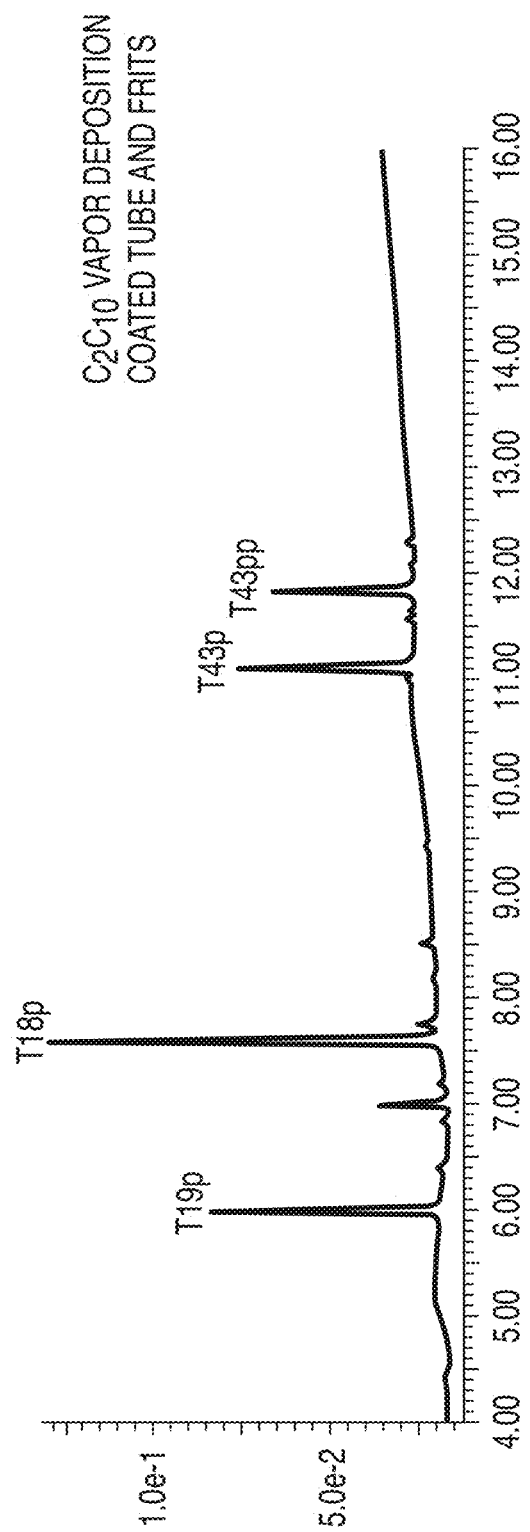
FIG. 7C shows a UV chromatogram obtained using a $C_2C_{10}$ vapor deposition coated tube/frit combination, in accordance with an embodiment of the technology.
Figure 8A:
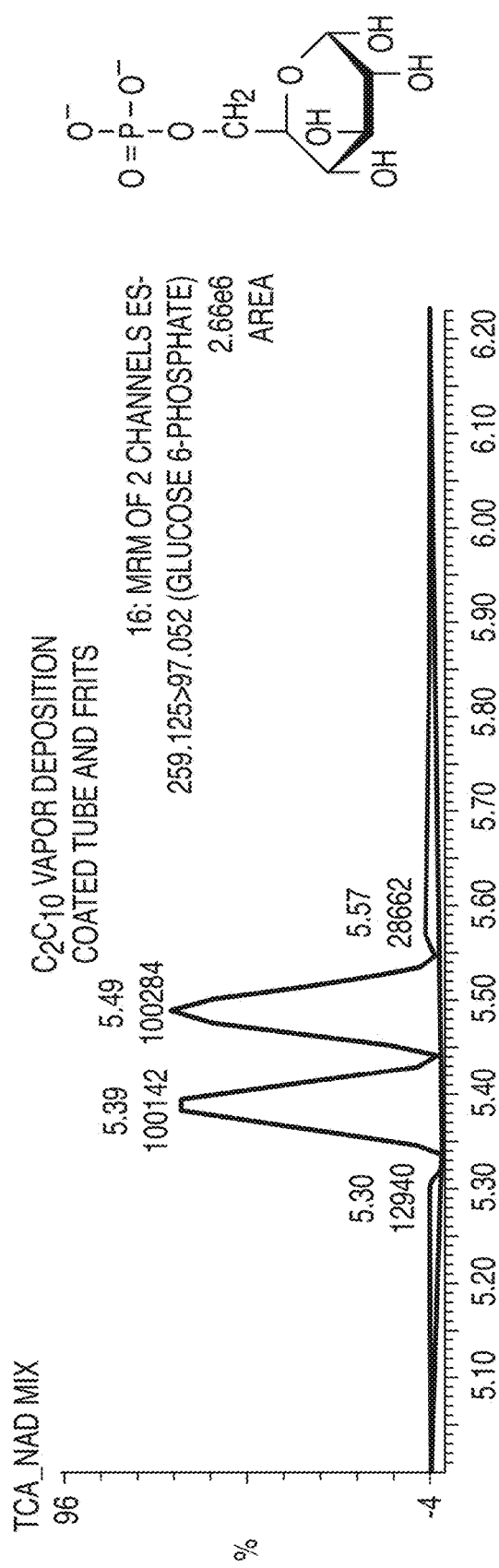
FIG. 8A is a chromatogram showing the effects of employing vapor deposition coated column hardware for the reversed phase LC analyses of glucose-6-phosphate, in accordance with an illustrative embodiment of the technology.
Figure 8B:
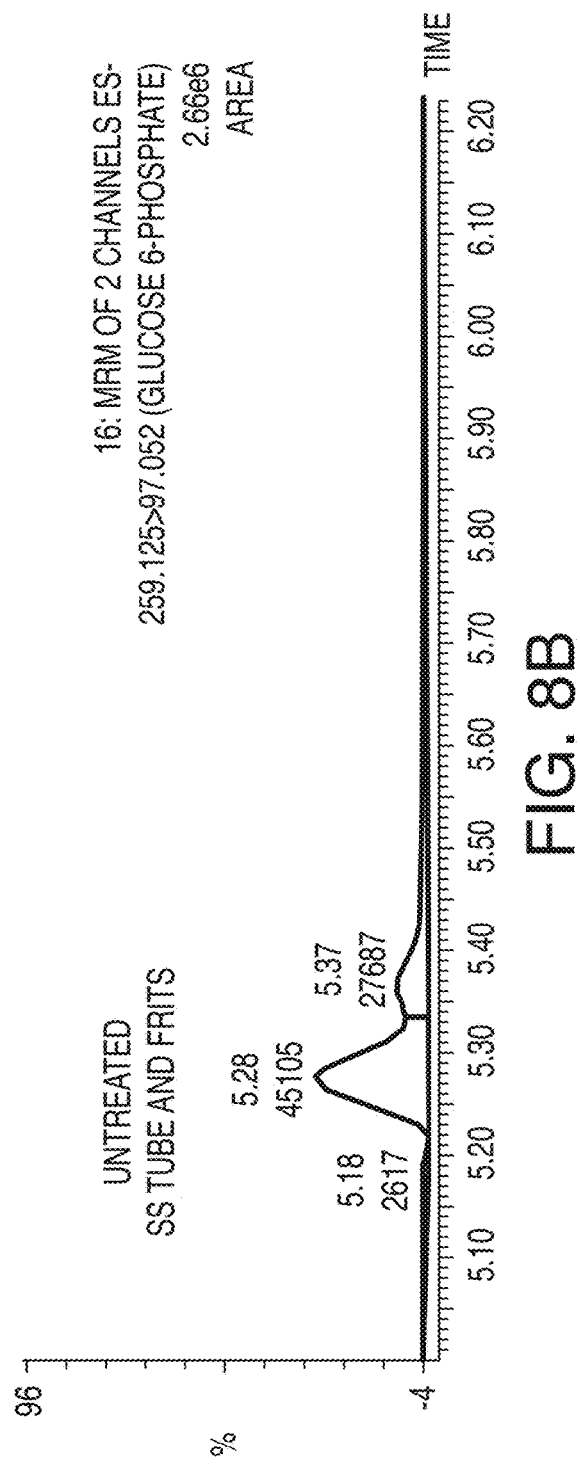
FIG. 8B is a chromatogram showing the effects of employing untreated column hardware for the reversed phase LC analyses of glucose-6-phosphate, in accordance with an illustrative embodiment of the technology.
Figure 11A:
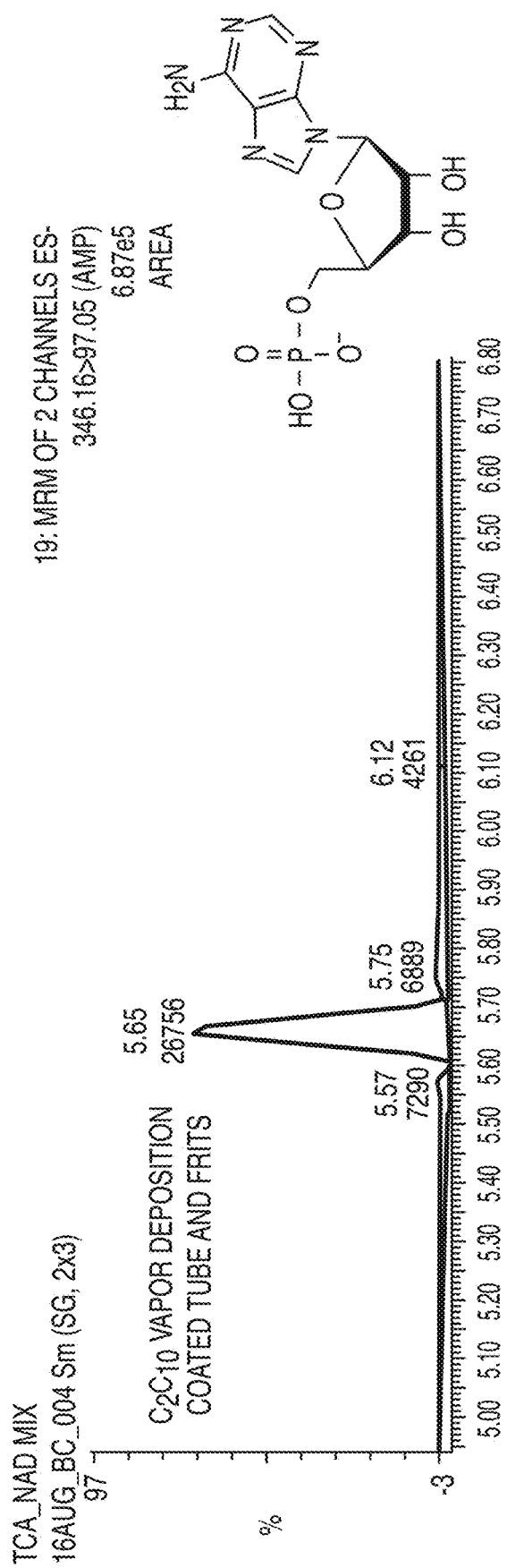
FIG. 11A is a chromatogram showing the effects of employing vapor deposition coated column hardware for the reversed phase LC analyses of adenosine monophosphate, in accordance with an illustrative embodiment of the technology.
Figure 11B:
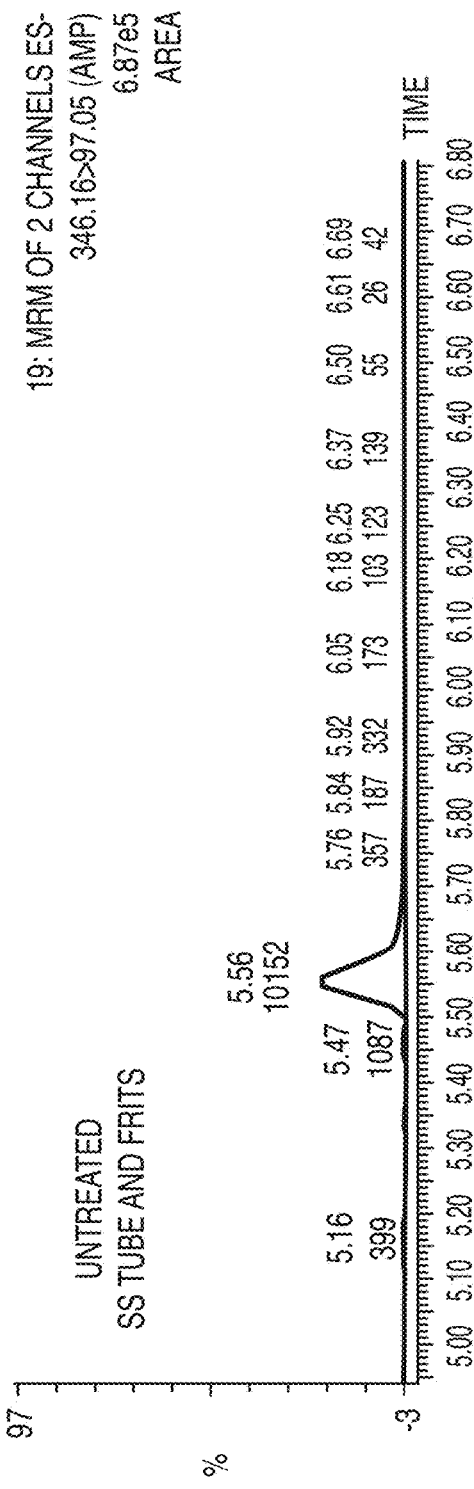
FIG. 11B is a chromatogram showing the effects of employing untreated column hardware for the reversed phase LC analyses of adenosine monophosphate, in accordance with an illustrative embodiment of the technology.

The principles learned from using vapor deposition coatings for phosphoglycan analysis were extended to facilitate the analysis of other types of phosphorylated biomolecules. In which case, the coatings have been found to be beneficial to improving the recovery of phosphorylated peptides under reversed phase chromatography conditions. To demonstrate these recovery advantages, we evaluated a mixture containing phosphopeptides. This particular sample contains three peptides that are singly phosphorylated and one that is doubly phosphorylated. Vapor deposition coated stainless steel column tubes along with matching coated stainless steel frits were first tested against corresponding untreated stainless steel hardware. FIG. 7A-7C show UV chromatograms obtained with these types of column hardware. In each case, the addition of the VPD #2, and the VPD #7 coatings increased the recovery of the singly phosphorylated peptides by at least 13% over the stainless steel alone (FIG. 4A-4C). The impact of coating the chromatographic flow path was much more pronounced with the doubly phosphorylated peptide. When using the stainless steel column hardware, there was no detectable recovery of the doubly phosphorylated peptide. However, when using either type of coated column hardware (VPD #2, and the VPD #7), this peptide became clearly visible in the obtained chromatograms. This result indicates, once again, that vapor deposition coatings can be used to minimize undesirable interactions with the metallic surfaces of chromatographic flow paths and in doing so allow for improved analyses of phosphorylated biomolecules.

As such, in one aspect, the vapor deposition coated column hardware is used to improve the recovery of phosphorylated biomolecules during analyses by liquid chromatography. In yet another embodiment of this invention, vapor deposition coated flow path components are used in conjunction with vapor deposition coated column hardware to improve the recovery of phosphorylated biomolecules during analyses by liquid chromatography.

The effects of this finding have been demonstrated for two examples of phosphorylated biomolecules, phosphorylated glycans and phosphorylated peptides. Phosphorylated biomolecules refer to any molecule naturally produced by an organism that contains a phospho group, including but not limited to phosphorylated proteins and polynucleotides. Furthermore, it is reasonable to envision this disclosure being used to improve liquid chromatographic analyses of smaller biomolecules, including but not limited to phospholipids, nucleotides and sugar phosphates. Indeed, vapor deposition coated column hardware has been found to be useful in improving the recovery and peak shape of sugar phosphates and nucleotides. The effects of employing vapor deposition coated versus untreated column hardware for the reversed phase LC analyses of glucose-6-phosphate, fructose-6-phosphate, adenosine triphosphate, and adenosine monophosphate are captured in FIGS. 8-11. Interestingly, these data indicate that the use of the vapor deposition coated column hardware can yield a significant improvement in both the overall recovery and peak shape of these phosphate containing small biomolecules. Thus, it is foreseeable that this disclosure could also be used to improve the chromatography of non-biomolecules, such as small-molecule pharmaceuticals containing either phospho or phosphonate functional groups.

Separation of Sialylated Glycans and Molecules Having Carboxylic Acid Moieties

It has additionally been discovered that vapor deposition coated hardware can be of benefit to mixed mode separations of sialylated glycans. In such a technique, sialylated glycans can be resolved using a stationary phase that exhibits anion exchange and reversed phase retention mechanisms. It was just recently discovered that a unique class of stationary phase, referred to as charged surface reversed phase chromatographic materials and described in International Application No. PCT/US2017/028856, entitled "CHARGED SURFACE REVERSED PHASE CHROMATOGRAPHIC MATERIALS METHOD FOR ANALYSIS OF GLYCANS MODIFIED WITH AMPHIPATHIC, STRONGLY BASED MOIETIES" and published as WO2017/189357 (and incorporated herein by reference in its entirety), is ideally suited to producing these types of separations. The use of a high purity chromatographic material (HPCM) with a chromatographic surface comprised of a diethylaminopropyl (DEAP) ionizable modifier, a C18 hydrophobic group and endcapping on a bridged ethylene hybrid particle has proven to be an exemplary embodiment for the separation of glycans labeled with amphipathic, strongly basic moieties, like that imparted by the novel labeling reagent described in International Application No. PCT/US2017/028856 (WO2017/189357). This so-called diethylaminopropyl high purity chromatographic material (DEAP HPCM) stationary phase is effective in separating acidic glycans as a result of it being modified with a relatively high pKa (~10) ionizable modifier that yields uniquely pronounced anionic retention.

Figures 13A, 13B, 13C, 13D:
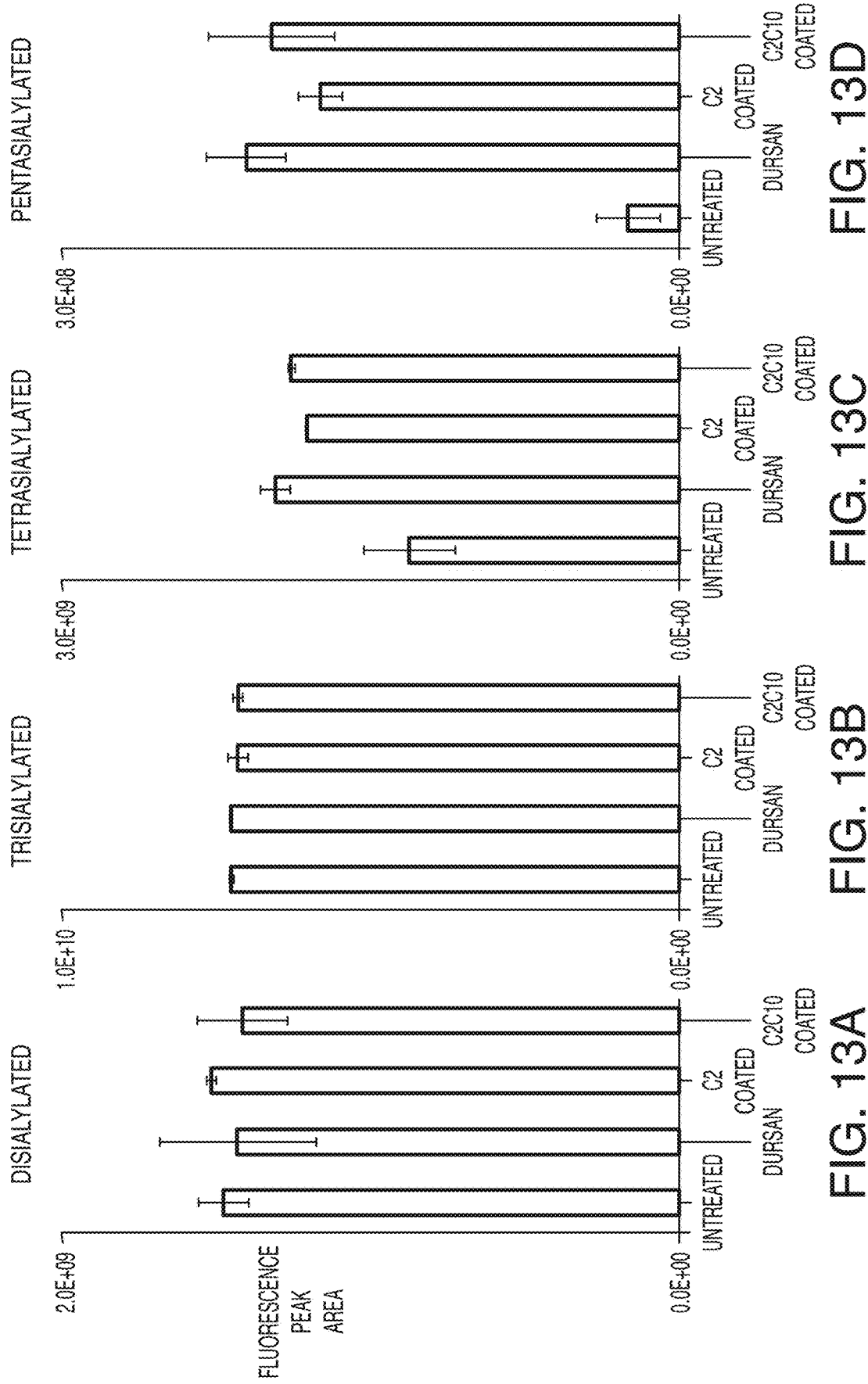
FIG. 13A is a graph showing fluorescence peak areas for disialyated glycans obtained with untreated stainless steel hardware compared to stainless steel hardware coated different types of vapor deposited coatings, in accordance with an illustrative embodiment of the technology.
FIG. 13B is a graph showing fluorescence peak areas for trisialyated glycans obtained with untreated stainless steel hardware compared to stainless steel hardware coated different types of vapor deposited coatings, in accordance with an illustrative embodiment of the technology.
FIG. 13C is a graph showing fluorescence peak areas for tetrasialyated glycans obtained with untreated stainless steel hardware compared to stainless steel hardware coated different types of vapor deposited coatings, in accordance with an illustrative embodiment of the technology.
FIG. 13D is a graph showing fluorescence peak areas for pentasialyated glycans obtained with untreated stainless steel hardware compared to stainless steel hardware coated different types of vapor deposited coatings, in accordance with an illustrative embodiment of the technology.

In an application to DEAP HPCM mixed mode separations of sialylated glycans, vapor deposition coated hardware has been shown to yield improved chromatographic recoveries and peak shapes of glycans containing greater than three sialic acid residues. A comparison of fluorescence chromatograms for fetuin N-glycans obtained with untreated stainless steel versus VPD #7 coated hardware is provided in FIG. 12, wherein the effect on peak shape and recovery of tetra- and pentasialylated glycans is easily visualized. The observed chromatographic differences are likewise easily quantified. In particular, fluorescence peak areas for the most abundant di-, tri-, tetra- and penta-sialylated glycans showed there were indeed very distinct differences in recoveries (FIG. 13). This testing was also used to demonstrate that other, chemically unique vapor deposition coating could be used with equally good effect. Much like the VPD #7 coated hardware, VPD #2 and SilcoTek Dursan® coated hardware showed equivalent capabilities in improving peak shape and recovery of the tetra- and penta-sialylated N-glycans. Interestingly though, it was not found to be necessary to use a coated flow through needle or column inlet in order to optimize peak shape and recovery.

As with phosphorylated species, this effect on the chromatography of sialylated glycans is believed to result from masking the metallic surface of the hardware and minimizing adsorptive sample losses that can occur with analytes that exhibit a propensity for metal chelation. However, the origin of the metal chelation is different in that the effect is a consequence of a glycan carrying multiple carboxylate residues versus one or two phosphorylated residues. Carboxylate containing compounds generally have a weak affinity for metals. Yet, when there are multiple carboxylate moieties present in one molecule, an opportunity for polydentate chelation is created, as is the case with tetra- and penta-sialylated glycans.

Accordingly, in an embodiment of this invention, vapor deposition coated column hardware is used during liquid chromatography of biomolecules containing greater than three carboxylic acid residues as a means to improve their peak shape and recovery. In yet another embodiment of this invention, vapor deposition coated flow path components are used in conjunction with vapor deposition coated column hardware to improve the peak shape and recovery of biomolecules containing greater than three carboxylic acid residues.

Separation of Proteins

Certain vapor deposition coatings have also been found to beneficially impact protein reversed phase chromatography. To demonstrate such, we evaluated a paradigmatic protein separation that is very important to the analysis of biopharmaceuticals, a monoclonal (mAb) subunit separation with MS-friendly, formic acid modified mobile phase. Using such a test, numerous combinations of column hardware materials have been examined. Vapor deposition coated stainless steel column tubes along with matching coated stainless steel frits were first tested against corresponding untreated stainless steel hardware. FIGS. 14A and 14B show fluorescence chromatograms obtained with these column hardware materials. From these data, it was found that hardware coated with VPD #7, but not hardware coated with VPD #2, was uniquely able to improve the baseline quality of the model separation, particularly in providing quicker returns to baseline. This improvement to the chromatographic performance of the separation is underscored by the fact that the chromatogram produced with the VPD #7 coated column also shows higher peak intensities for some of the subunits. The nature of this baseline issue, as it exists with stainless steel hardware, can be reasoned to be a result of the protein analytes undergoing problematic secondary interactions and not homogenously eluting at one particular eluotropic strength. Interestingly, in this example, the VPD #7 MVD hardware did not appear to significantly improve half height peak capacity nor the carryover of the columns, which was universally found to be ~0.9%. That is to say, for protein reversed phase chromatography, it would seem that vapor deposition coatings improve the quality of separation predominately through affecting baseline properties.

An effect such as this can be very significant to protein reversed phase separations, particularly those intended to facilitate detection by online electrospray ionization (ESI)-mass spectrometry (MS). Often, it is critical to have quick returns to baseline in ESI-MS data given that it will make the assignment of chromatographic peaks less ambiguous. Signal from previously eluted species will be less abundant and therefore less confounding in data accumulated for later eluting peaks. With this in mind, 11 additional combinations of column hardware materials were screened, using ESI-MS detection as the means to assessing the quality of the data. FIG. 15A presents total ion chromatograms (TICs) for some of these materials, including columns constructed with stainless steel alternatives, namely polyether ether ketone (PEEK) and a low titanium, nickel cobalt alloy (MP35NLT). Surprisingly, columns constructed of VPD #7 coated hardware were the only found to give uniquely quick returns to baseline. Stainless steel, PEEK, and VPD #2 coated hardware showed comparatively slower returns to baseline. In addition, control experiments showed that the improvement to baseline quality can be achieved through the use of a VPD #7 coated frit alone and that coated tubing is not required to achieve an effect. Further experimentation culminating in the chromatograms of FIG. 15B has made it possible to glean additional insights. One of which is that it does not matter if the frit has a 0.2 or 0.5 µm porosity or if the VPD #7 coating has been thermally cured in the form of an annealing process (resulting in a VPD #8 coating). In contrast, neither a thicker VPD #3 coating (~1800 Å thickness) nor a cured coating (VPD #5) with an increased contact angle of 90° (up from ~35°) were able to produce the effect. Accordingly, VPD #7 coated frits are very unique in their ability being to affect the baseline of the example protein separation. While not limited to theory, it would seem reasonable to suggest that this effect derives from the hydrophobicity/contact angle of this coating. It could be that these coated frits closely mimic the surface chemistry of the reversed phase stationary phase. Consequently, a column with VPD #7 coated frits might exhibit adsorption sites (particularly those near the frit surface) that are more uniform in their chemical properties. Testing has shown that this effect on the protein reversed phase separation can be localized to the inlet frit of the column, lending credence to this hypothesis (FIG. 16). Indeed, one hydrophobic VPD #7 vapor deposition coated frit at the column inlet is sufficient to produce uniquely quick returns to baseline for the example mAb subunit separations. Proteins undergo reversed phase chromatography via fairly discrete adsorption/desorption events. Consequently, upon loading, protein analytes will be most concentrated at and likewise spend a significant amount of time at the head of the column, where an interface exists between the inlet frit and the packed bed of the stationary phase. At this interface, a protein analyte would have an opportunity to establish undesired secondary interactions that would be cumulative to and energetically different than the desired hydrophobic interaction with the stationary phase. It is plausible that using a frit with surface properties similar to the stationary phase mitigates any chromatographic problems related to there being energetically and chemically diverse adsorption sites present at this packed bed interface. While not limited to theory, it may also be possible that a frit, such as the $C_2C_{10}$ vapor deposition coated inlet frit (e.g., frit coated with VPD #7), imparts an entirely novel focusing effect to protein reversed phase separations that cannot be explained by the understanding and descriptions noted above. In addition, it is possible that a frit, such as the VPD #7 vapor deposition coated inlet frit, makes a unique contribution to how a stationary phase packs into a column. Use of a vapor deposition coated frit as the substrate for building a packed column bed may advantageously impact the properties of a stationary phase and resultant chromatography.

As such, in an embodiment of this invention, vapor deposition coated column hardware is used to improve the chromatographic performance of protein reversed phase separations. In yet another embodiment of this invention, a vapor deposition coating with a contact angle of >90°, more preferably greater than 100 Å, is used to coat the tubing and frits of a column, or chromatographic device, as a means to improve the baseline and/or tailing factors of protein separations.

In a separate embodiment, this invention may utilize a frit material that is constructed of a specific polymer, such that an equivalently hydrophobic surface is achieved, specifically one with a contact angle greater than 90°, more preferably greater than 100 Å. Polytetrafluoroethylene (PTFE), polymethylpentene (PMP), high density polyethylene (HDPE), low density polyethylene (LDPE) and ultra high molecular weight polyethylene (UHMWPE) are examples of hydrophobic polymers that could be suitable for use as the frit or column material in other embodiments of this invention. In fact, an inlet frit constructed of porous PTFE (1.5 mm thick, Porex PM0515) was found to favorably affect protein reversed phase baselines, in a manner similar to that of the previously mentioned VPD #7 vapor deposition coated inlet frit (FIG. 17). Frits of alternative compositions are also relevant to this invention. In yet another embodiment, parylene, that is poly p-xylene polymer, coatings could be used treat column frits and to thereby improve the properties of a protein reversed phase separation. In addition, glass membranes could be used as the basis of a frit material. Onto the glass membrane substrate, silanes could be bonded to advantageously manipulate the hydrophobicity and contact angle of the material. These and other such membranes could also be used in conjunction with a backing material, like a porous polymer sheet, to lend physical rigidity to the apparatus.

Finally, vapor deposition coated hardware has been found to be of benefit to aqueous biomolecule separations, such as protein ion exchange chromatography. When looking to understand the charge heterogeneity of a sample, an analyst will often choose to resolve the components of a sample by ion exchange. In the case of protein therapeutics, this type of analysis is performed as a means to interrogate so-called charge variants, such as deamidiation variants, that can have a detrimental effect on the efficacy of the corresponding drug product. Charge variant separations by way of ion exchange can therefore be critical to the effectiveness of a characterization approach for a protein therapeutic, most particularly a monoclonal antibody. Being such an important analytical approach, protein ion exchange must be robust and able to quickly and reliably yield accurate information.

Figure 22:
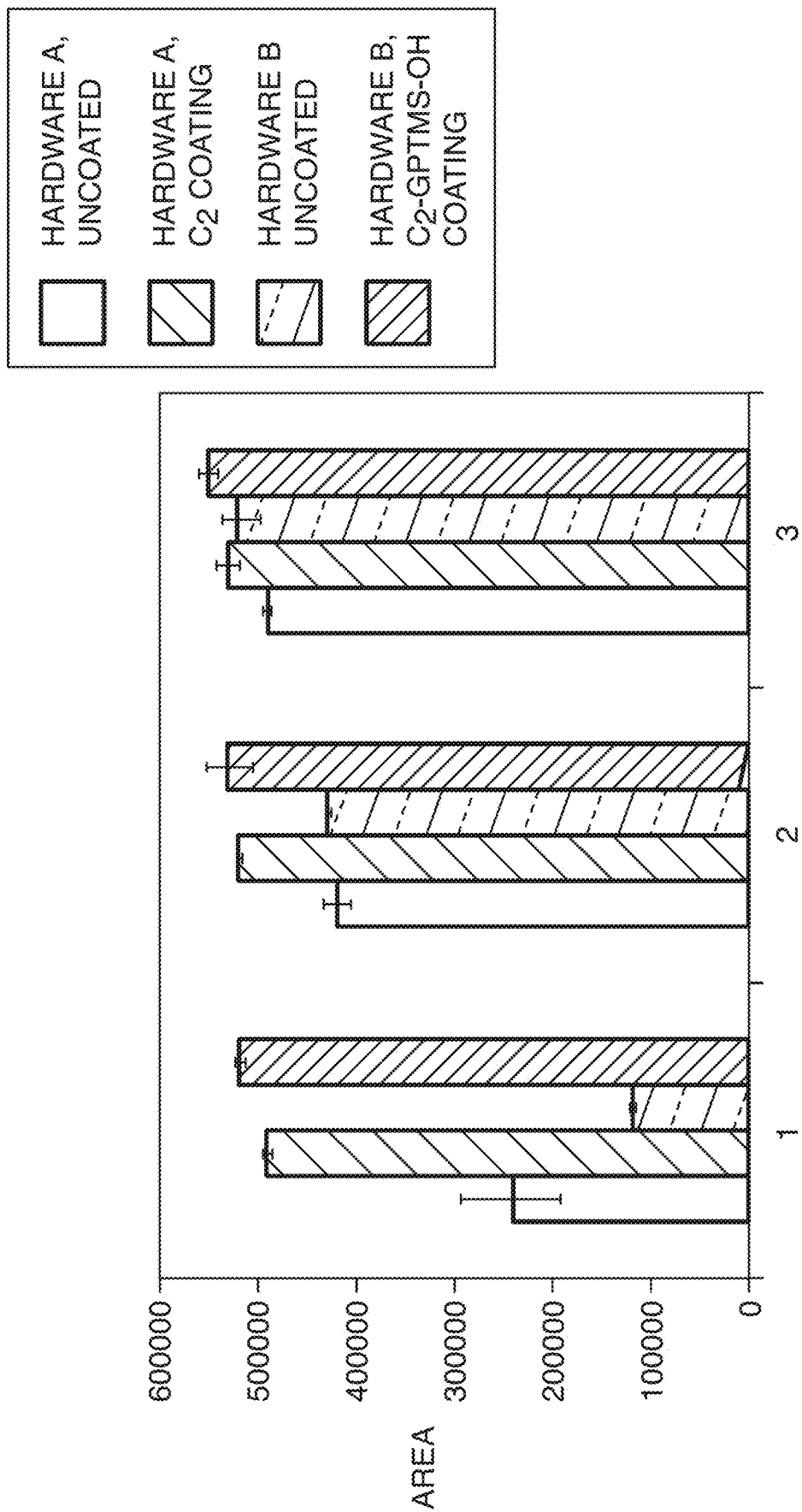
FIG. 22 presents a bar graph showing peak areas of NIST reference materials 8671 obtained from sequential cation exchange separations over three injections of the sample, in accordance with an illustrative embodiment of the technology. This bar graph compares the peak areas for four different constructions in which the left most bar in each injection is an uncoated hardware A construction. The second from the left is a coated version of hardware A. The third bar from the left is an uncoated hardware B construction and the fourth or last bar per injection is a coated hardware B construction.
Figure 23A:
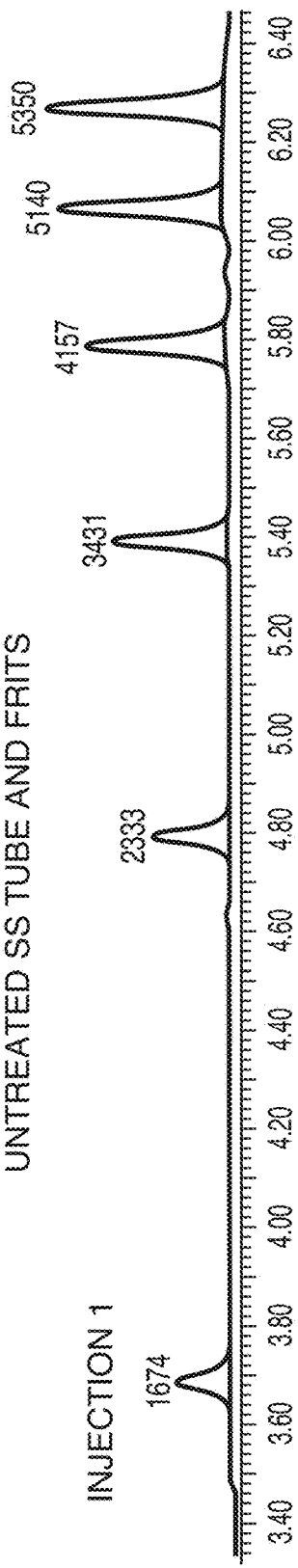
FIG. 23A is a reversed-phase chromatogram of the first injection of 5 picomoles of deoxythymidine oligomers (15, 20, 25, 30, and 35-mer) obtained from a 2.1×50 mm 1.7 μm organosilica 130 Å $C_{18}$ column constructed with an untreated stainless steel (SS) tube and frits, in accordance with an illustrative embodiment of the technology.
Figure 23B:
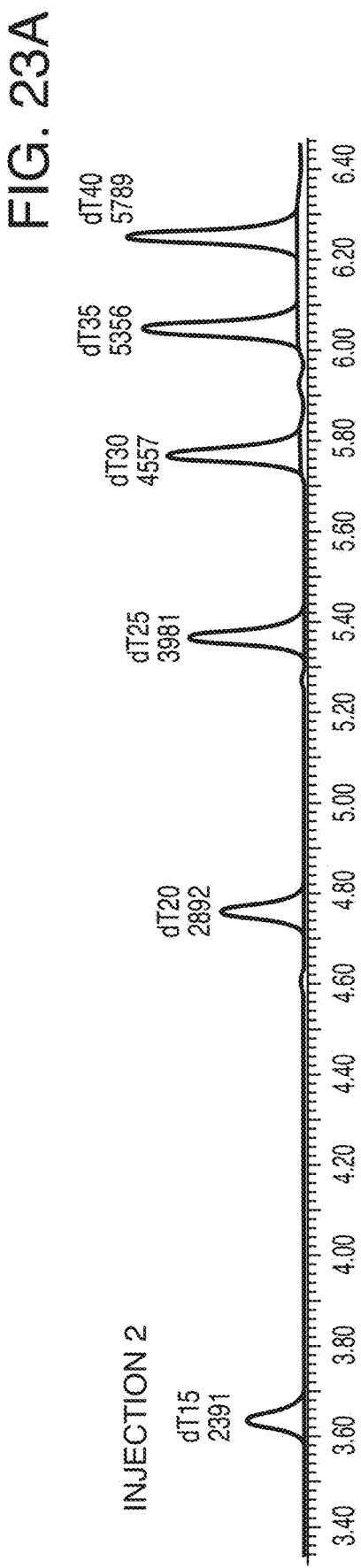
FIG. 23B is a reversed-phase chromatogram of the second injection of 5 picomoles of deoxythymidine oligomers (15, 20, 25, 30, and 35-mer) obtained from a 2.1×50 mm 1.7 μm organosilica 130 Å $C_{18}$ column constructed with an untreated stainless steel (SS) tube and frits, in accordance with an illustrative embodiment of the technology.
Figure 23C:
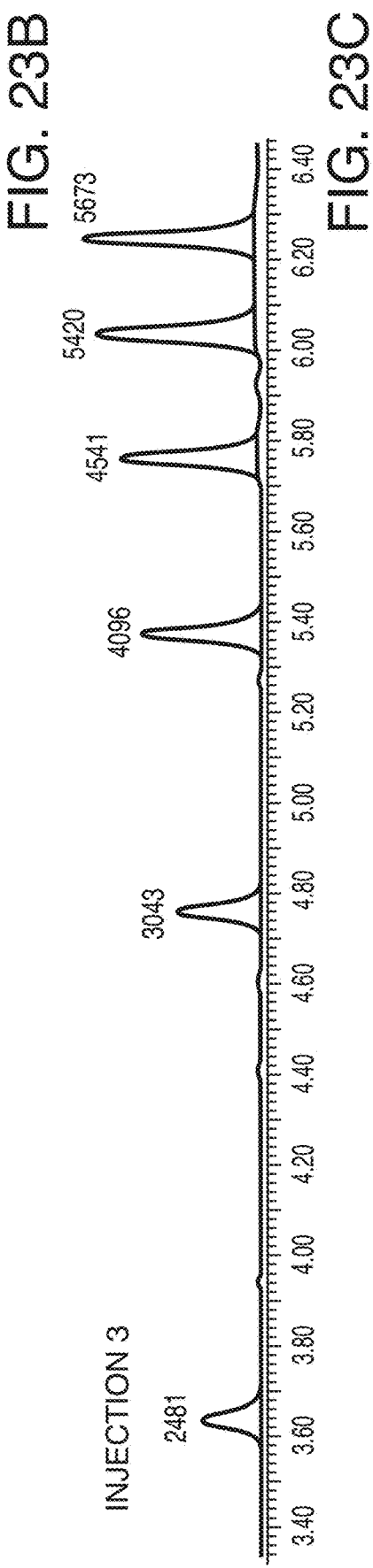
FIG. 23C is a reversed-phase chromatogram of the third injection of 5 picomoles of deoxythymidine oligomers (15, 20, 25, 30, and 35-mer) obtained from a 2.1×50 mm 1.7 μm organosilica 130 Å $C_{18}$ column constructed with an untreated stainless steel (SS) tube and frits, in accordance with an illustrative embodiment of the technology.
Figure 23D:
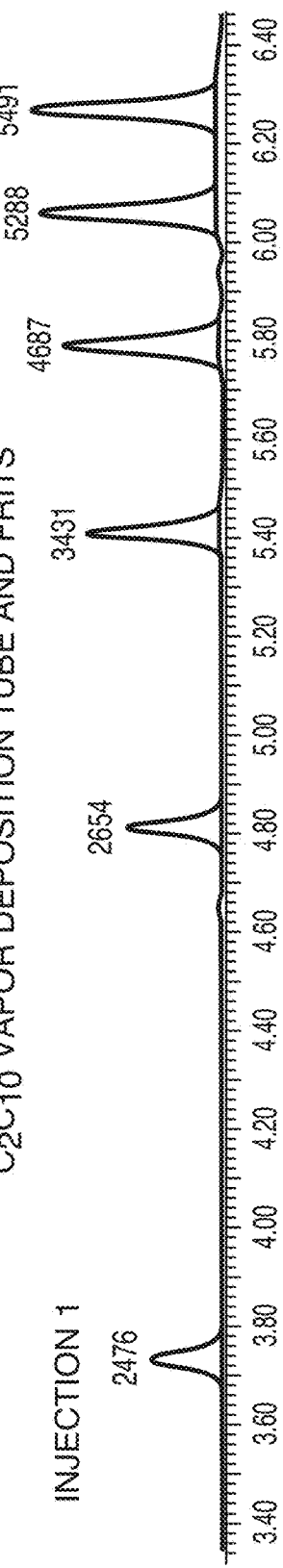
FIG. 23D is a reversed-phase chromatogram of the first injection of 5 picomoles of deoxythymidine oligomers (15, 20, 25, 30, and 35-mer) obtained from a column constructed with a $C_2C_{10}$ vapor deposition coated tube and frits, in accordance with an illustrative embodiment of the technology.
Figure 23E:
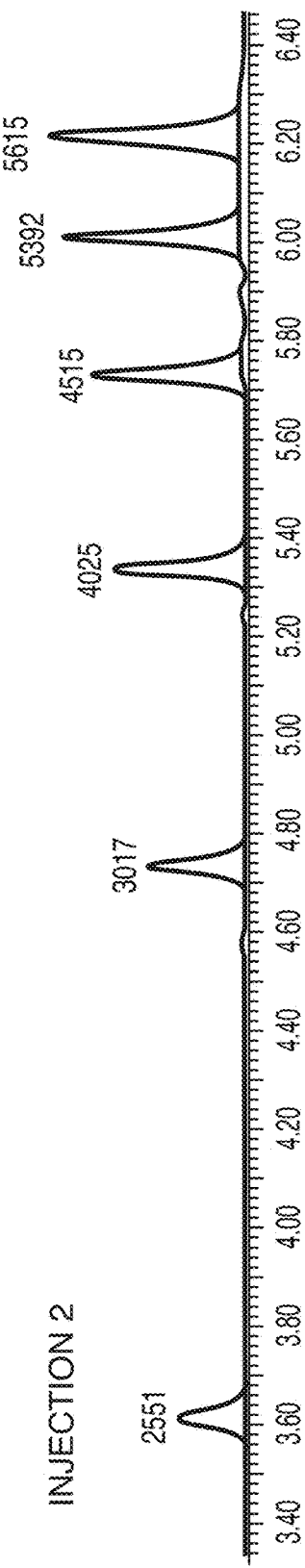
FIG. 23E is a reversed-phase chromatogram of the second injection of 5 picomoles of deoxythymidine oligomers (15, 20, 25, 30, and 35-mer) obtained from a column constructed with a $C_2C_{10}$ vapor deposition coated tube and frits, in accordance with an illustrative embodiment of the technology.
Figure 23F:
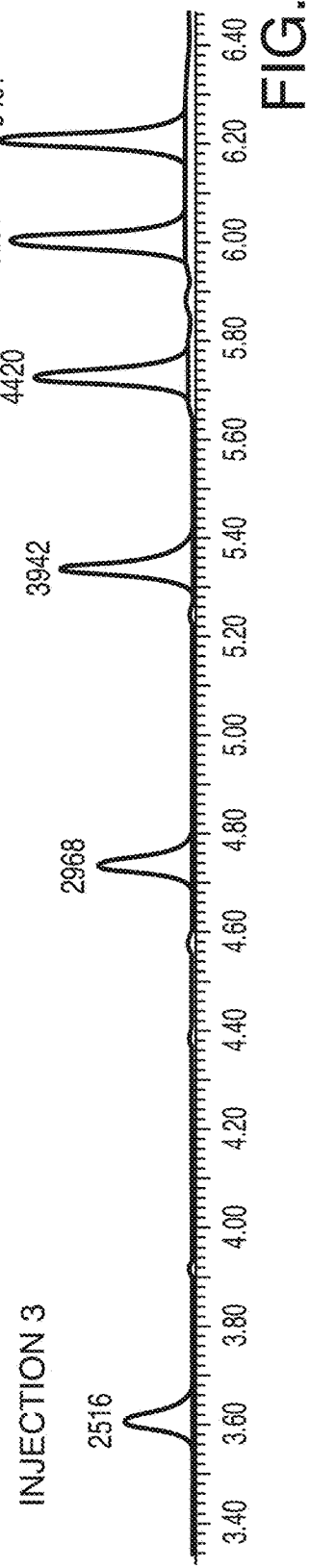
FIG. 23F is a reversed-phase chromatogram of the third injection of 5 picomoles of deoxythymidine oligomers (15, 20, 25, 30, and 35-mer) obtained from a column constructed with a $C_2C_{10}$ vapor deposition coated tube and frits, in accordance with an illustrative embodiment of the technology.
Figure 24:
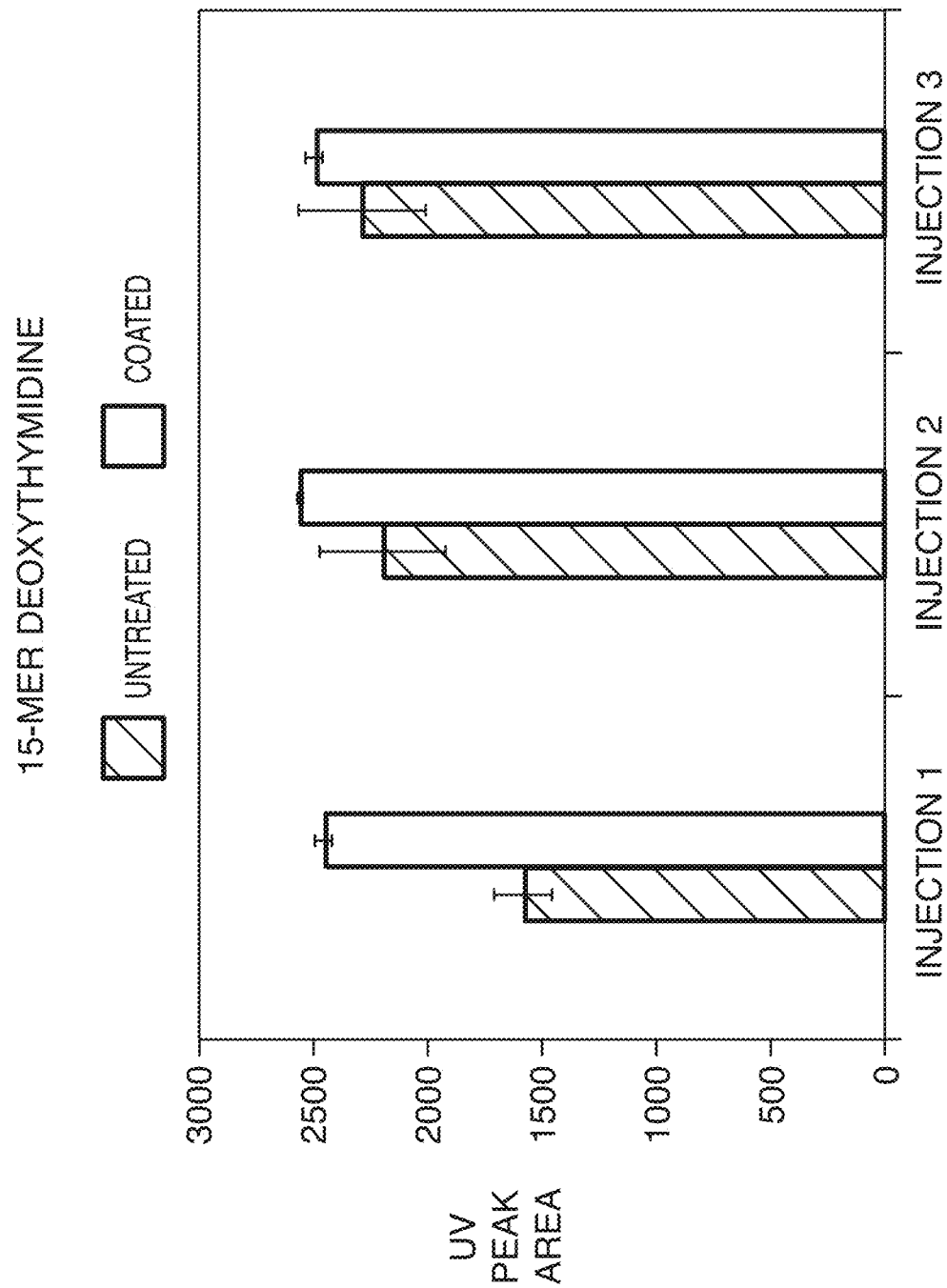
FIG. 24 is a graph showing the average UV peak areas of a 15-mer deoxythymidine analyte as observed during reversed phase chromatography and initial injections onto either a 2.1×50 mm 1.7 μm organosilica 130 Å $C_{18}$ column constructed with untreated stainless steel (SS) or $C_2C_{10}$ vapor deposition coated components, in accordance with an illustrative embodiment of the technology. Analyses were performed in duplicate using two untreated columns and two $C_2C_{10}$ vapor deposition coated columns.

To this end, ion exchange separations of a monoclonal antibody were evaluated, and the effects of using uncoated versus vapor deposition coated column hardware were contrasted. FIGS. 21A-21L presents chromatograms of NIST reference material 8671, an IgG1κ mAb, as obtained from sequential cation exchange separations and repeat injections of sample. In this evaluation, columns derived from four different constructions were tested. These columns varied with respect to both hardware design and vapor deposition coating. From the observed results, it was most apparent that uncoated hardware showed a prominent conditioning effect, as manifest in there having been low peak areas on initial injections. While not limited to theory, it is believed that the metallic surfaces of the uncoated column hardware imposed adsorptive losses on these separations and thereby hindered recovery of the sample. In contrast, vapor deposition coated hardware, both $C_2$ or $C_2$-GPTMS-OH chemistries, yielded comparatively high peak areas even on the very first runs of the columns (FIG. 22). That is, coated hardware showed no evidence of requiring a passivation step, giving it the unique advantage of more quickly providing accurate chromatographic data. Here, it is clear that the noted vapor deposition coatings enhance the chromatographic properties of metallic hardware. Little can be seen in the way of distinguishing the chromatographic performance of the two tested vapor deposition coatings, namely the $C_2$ and $C_2$-GPTMS-OH chemistries. However, the $C_2$-GPTMS-OH coating has an inordinately low contact angle (as does $C_2$PEO). It is foreseeable that certain types and classes of biomolecules will require a highly hydrophilic flow path. One such example could indeed be aqueous protein separations in which hydrophobic interactions could lead to poor recovery or peak tailing. As a whole, it is believed that vapor deposition coated hardware will show advantages for numerous forms of aqueous separations, including but not limited to ion exchange, size exclusion and hydrophobic interaction chromatography, and that the most ideal vapor deposition coating would be one that is very hydrophilic. Accordingly, in an embodiment of this invention, a vapor deposition coated column is used to improve the recovery of samples from aqueous chromatographic separations. In a more specific embodiment, a vapor deposition coating with a contact angle less than 20° is used to improve the recovery of biomolecules in ion exchange, size exclusion or hydrophobic interaction chromatography.

EXAMPLES

Example 1

$C_2$ and $C_2C_{10}$ Vapor Deposition Coatings

Prior to coating, all metal components are passivated according to a nitric acid passivation. Passivated parts and a silicon wafer are then introduced to the vapor deposition chamber and vacuum is established. The first step is a 15 minute, 200 Watt, 200 cc/min oxygen plasma cleaning step. Next is the first vapor deposition cycle. Each vapor deposition cycle contains a silane vapor deposition, followed by the introduction of water vapor for silane hydrolysis. The silane vapor is delivered at a pressure of 2.0 Torr for 5 seconds, and then the water vapor is delivered at a pressure of 50 Torr for 5 seconds. Following delivery, the silane and water is left to react with the substrate for 15 minutes. This cycle is repeated to produce the desired number of layers and coating thickness. An additional processing cycle can be implemented to functionalize the coating with yet another silane. Moreover, a post coating annealing step can be used to further cross-link and increase the hydrophobicity of the coating. Typically, the annealing cycle involves subjecting the coating to 200° C. for 3 hours under vacuum.

A silicon wafer is used as a coupon to measure the thickness and contact angle of the coating. To measure the thickness, a Gaertner Scientific Corporation stokes ellipsometer model LSE is used. By analyzing the change in polarization of light, and comparing to a model, the film thickness can be established. To measure the contact angle, a Ramé-Hart goniometer model 190 is used. After dropping a controlled amount of water onto a perfectly level silicon wafer, optical techniques are used to measure the contact angle.

Example 2

$C_2$-GPTMS-OH Vapor Deposition Coatings

Prior to coating, all metal components are passivated according to a nitric acid passivation. Passivated parts and a silicon wafer are then introduced to the vapor deposition chamber and vacuum is established. The first step is a 15 minute, 200 Watt, 200 cc/min oxygen plasma cleaning step. Next is the first vapor deposition cycle. Each vapor deposition cycle contains a silane vapor deposition, followed by the introduction of water vapor for silane hydrolysis. The silane vapor is delivered at a pressure of 2.0 Torr for 5 seconds, and then the water vapor is delivered at a pressure of 50 Torr for 5 seconds. Following delivery, the silane and water is left to react with the substrate for 15 minutes. This cycle is repeated to produce the desired number of layers and coating thickness. In this example, the bis(trichlorosilyl) ethane silane is used to build up an adhesion or primer layer of approximately 800 Å. After $C_2$ deposition, the 3-(glycidoxypropyl)trimethoxysilane is delivered anhydrously to a pressure of 0.4 Torr in the vapor deposition chamber. This silane vapor is left to react with the $C_2$ coated substrate for one hour. This process results in an epoxide terminated coating, with a contact angle of 50°. After deposition, the next step is to hydrolyze the epoxide groups. This is performed either in the liquid phase or the vapor phase, with 0.1M acetic acid. After epoxide hydrolysis, the contact angle is <20°. Contact angle measurements are taken on a silicon wafer using a Ramé-Hart goniometer model 190.

Example 3

Alternative Contact Angle Measurement

It is relatively easy to measure the contact angle on the flat silicon wafers using a goniometer. However, not all our substrates have such smooth and flat surfaces. Frits can be considered a chromatography column's most important substrate, since the fluidic surface area to mass ratio is higher in the frit than in any other column hardware component. In order to measure the solid-liquid wetting properties of frit porosity, and confirm the presence of a coating, we can use the bubble point test. The bubble point test is used to determine the largest pore diameter of a frit structure, and the bubble point pressure is related to this diameter with the following equation:

$$P = (2\gamma \cos \theta)/r$$

Where,
P=bubble point pressure, Pa (measured)
γ=surface tension of test liquid, N/m (known)
Θ=contact angle between test liquid and pore material (calculated)
r=largest pore radius, m (calculated)

This equation is from ASTM E128 and is derived from the equilibrium condition of capillary rise.

Figure 18:
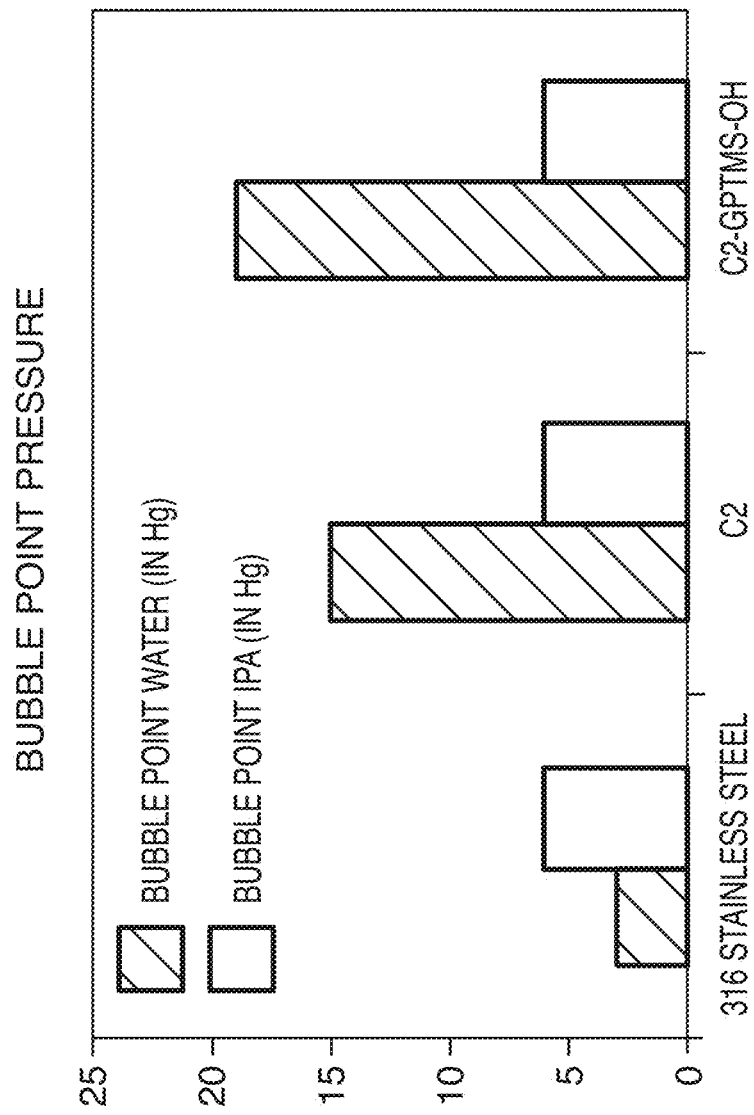
FIG. 18 is a bar graph showing bubble point pressure in each of water and IPA for a non-coated stainless steel frit and stainless steel frits coated in accordance with one or more illustrative embodiments of the technology. The bubble point in water is provided as the left bar, and the bubble point in IPA is provided as the right bar for each type of frit.
Figure 19:
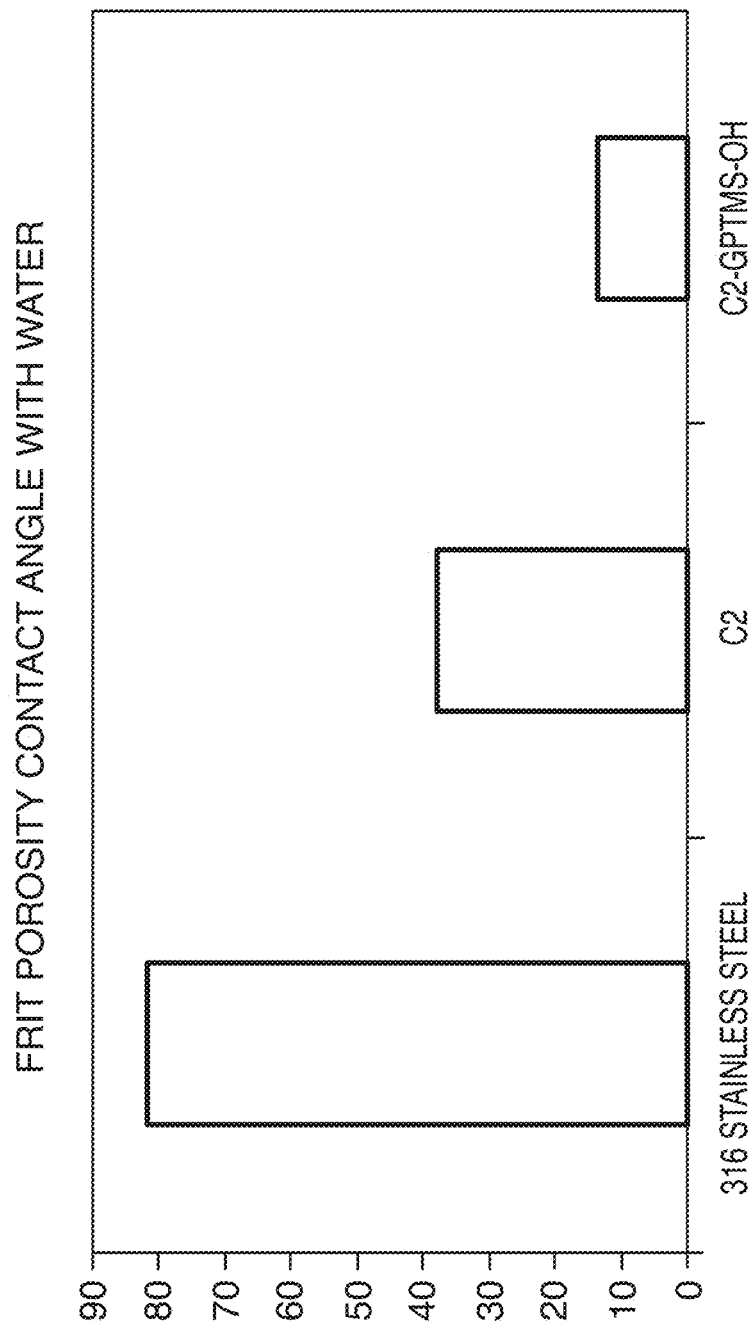
FIG. 19 is a bar graph showing a comparison of fit porosity contact angle with water for a non-coated stainless steel frit versus stainless steel frits coated in accordance with one or more embodiments of the technology.

Using the bubble point test to calculate a contact angle requires two steps. This first is to test the frit in IPA, and assume a 0 contact angle, since IPA has excellent wetting characteristics. This will yield a maximum pore diameter. The next step is to repeat the experiment with water as the test liquid, and the known pore radius. This will yield the contact angle with water, relative to the assumed 0 degree contact angle of IPA. FIG. 18 displays the different bubble point pressures recorded versus coating composition. FIG. 19 displays the derived contact angles versus coating composition. These values correlate well with measurements taken with a goniometer on a flat silicon wafer.

Example 4

Corrosion Performance of Silane Coatings

Figure 20:
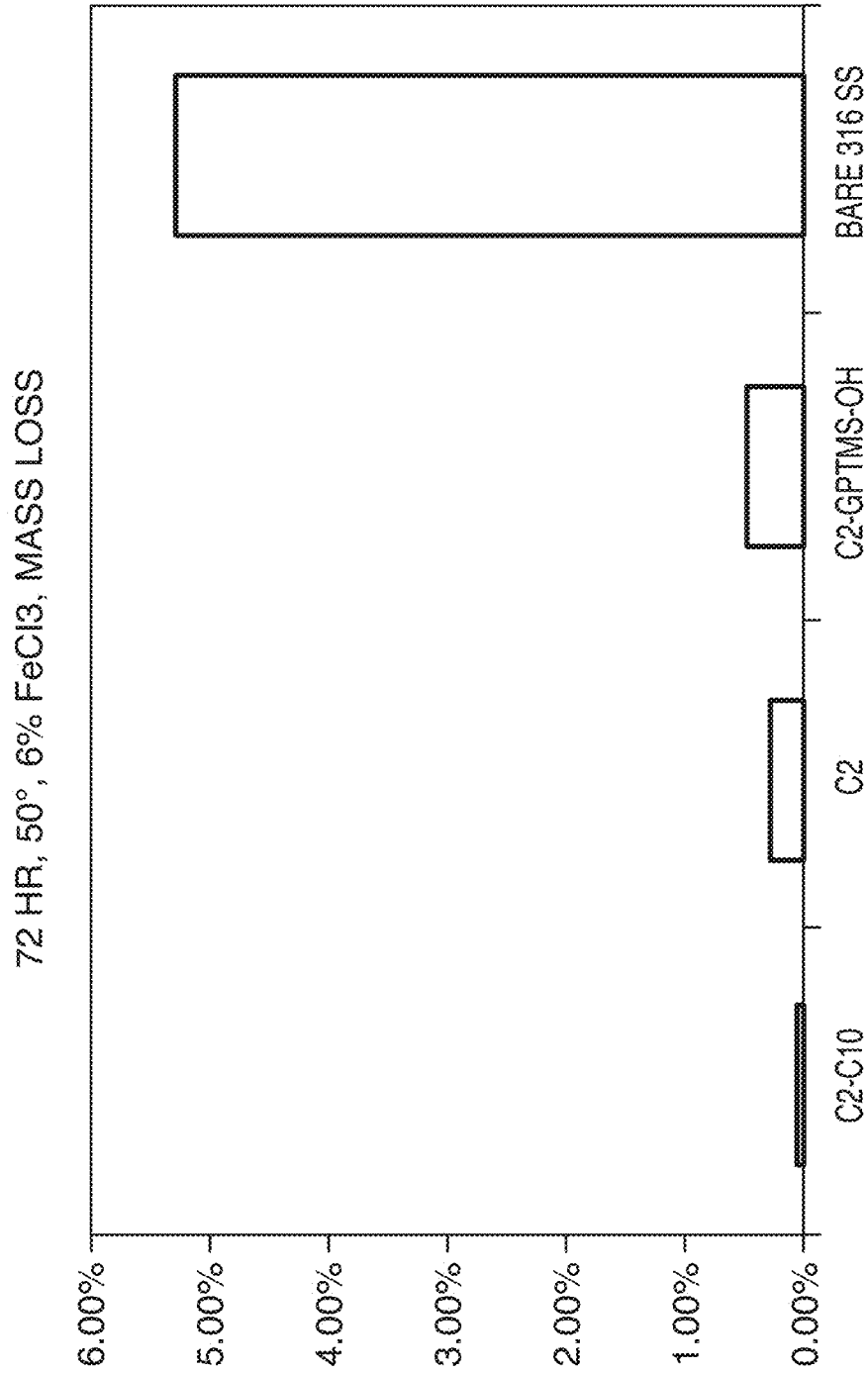
FIG. 20 is a bar graph showing a comparison of mass loss test according to ASTM G48 Method A for a bare or uncoated stainless steel frit versus stainless steel frits coated in accordance with one or more embodiments of the technology.
Figure 21A:
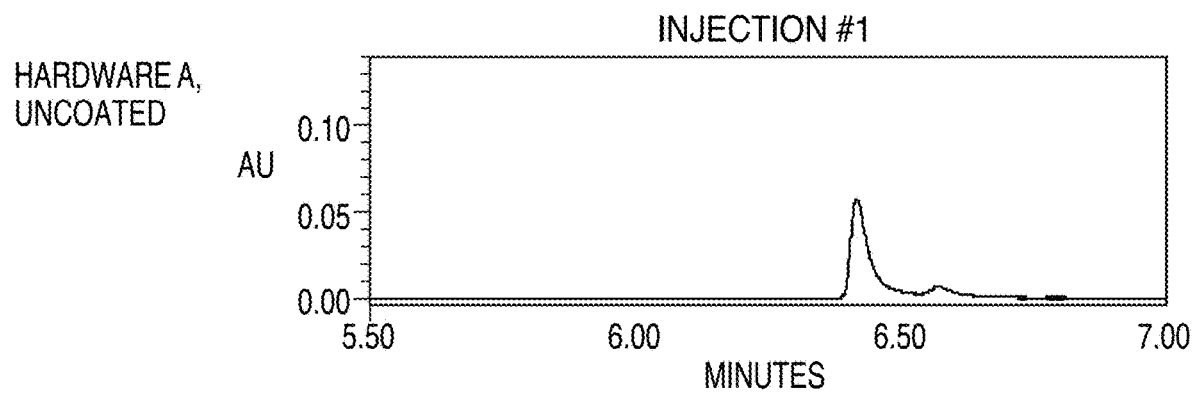
FIG. 21A is a chromatogram of NIST reference material 8671, an IgG1κ mAb, as obtained from injection 1 using hardware A, uncoated, in accordance with an illustrative embodiment of the technology.
Figure 21B:
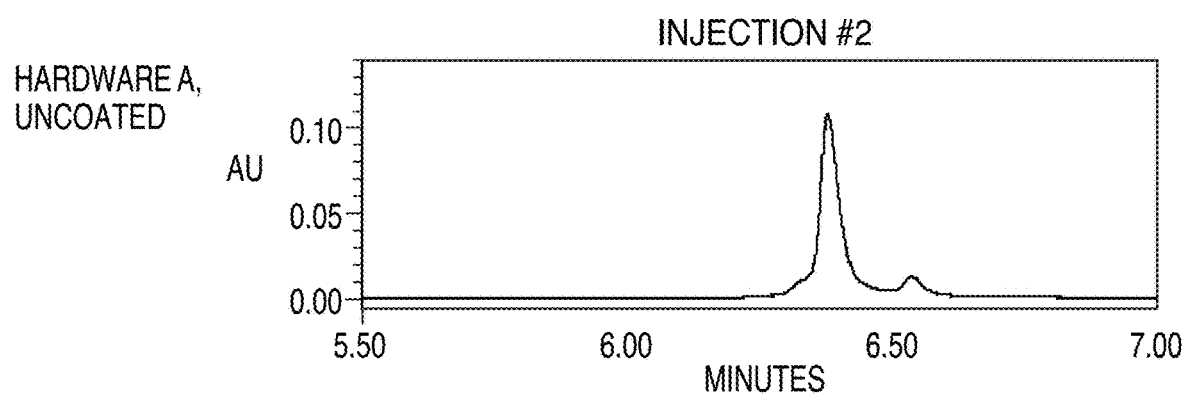
FIG. 21B is a chromatogram of NIST reference material 8671, an IgG1κ mAb, as obtained from injection 2 using hardware A, uncoated, in accordance with an illustrative embodiment of the technology.
Figure 21C:
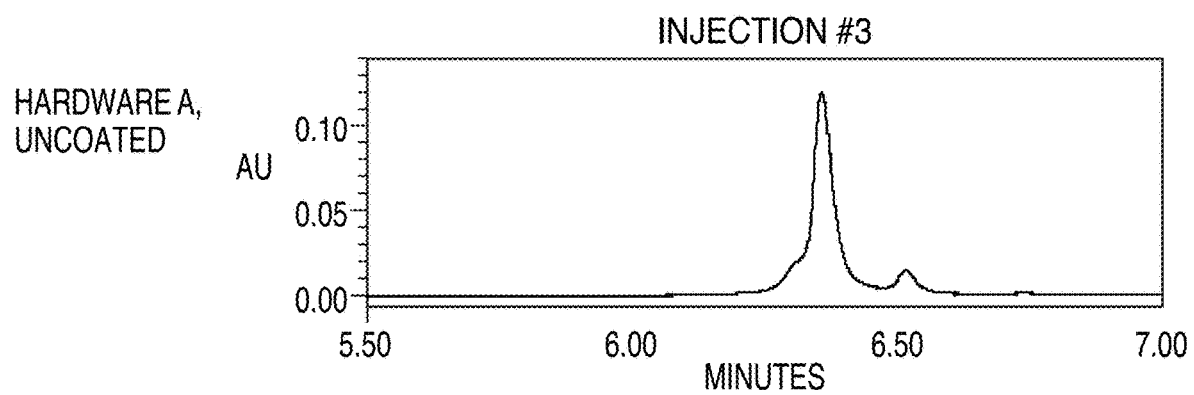
FIG. 21C is a chromatogram of NIST reference material 8671, an IgG1κ mAb, as obtained from injection 3 using hardware A, uncoated, in accordance with an illustrative embodiment of the technology.
Figure 21D:
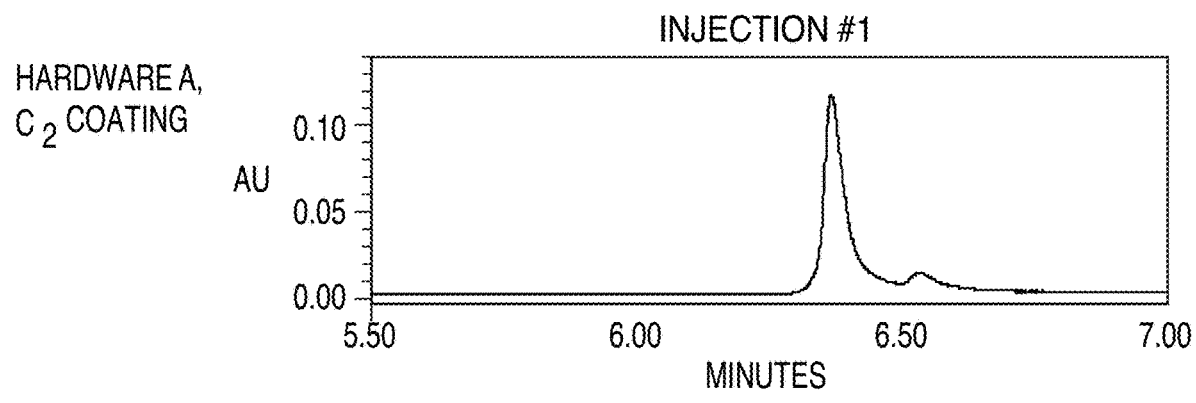
FIG. 21D is a chromatogram of NIST reference material 8671, an IgG1κ mAb, as obtained from injection 1 using hardware A, $C_2$ coating, in accordance with an illustrative embodiment of the technology.
Figure 21E:
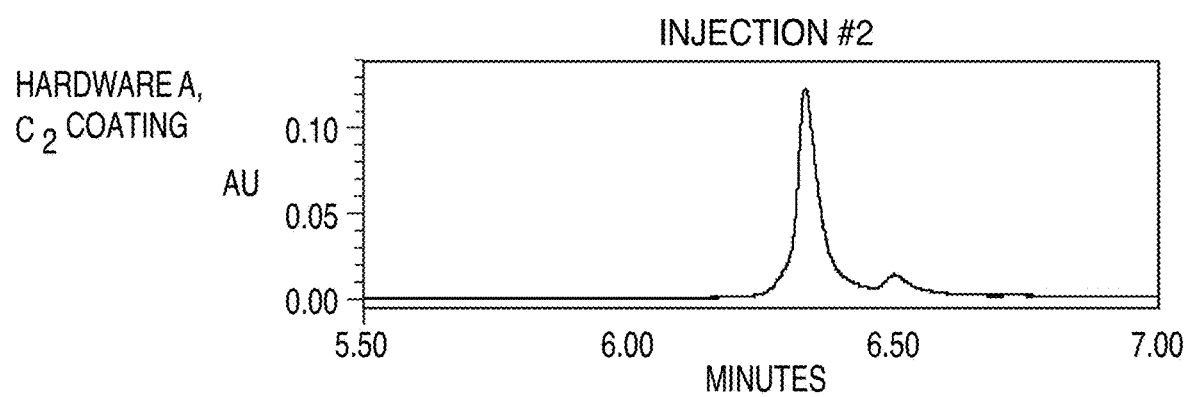
FIG. 21E is a chromatogram of NIST reference material 8671, an IgG1κ mAb, as obtained from injection 2 using hardware A, $C_2$ coating, in accordance with an illustrative embodiment of the technology.
Figure 21F:
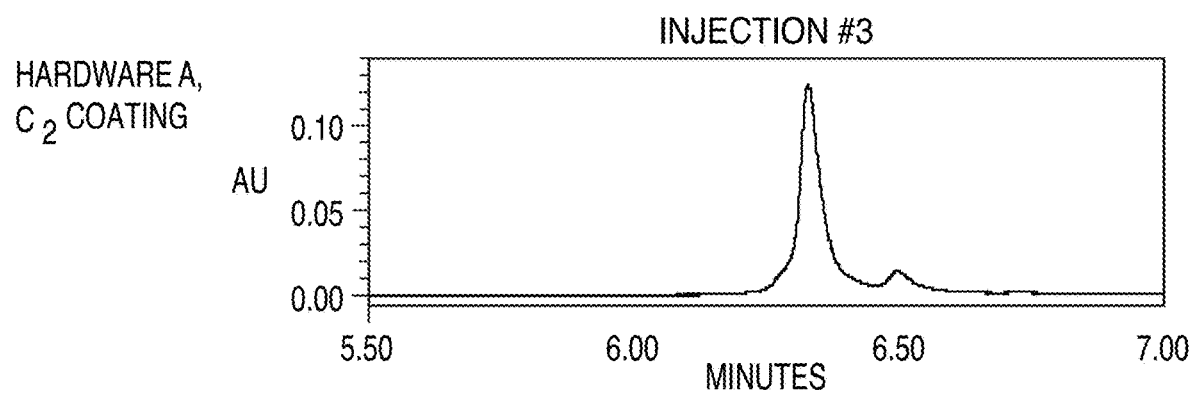
FIG. 21F is a chromatogram of NIST reference material 8671, an IgG1κ mAb, as obtained from injection 3 using hardware A, $C_2$ coating, in accordance with an illustrative embodiment of the technology.
Figure 21G:
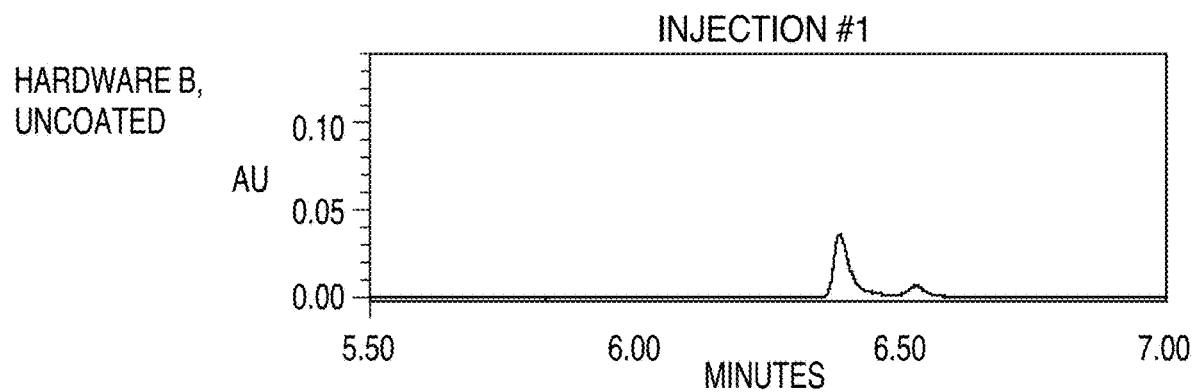
FIG. 21G is a chromatogram of NIST reference material 8671, an IgG1κ mAb, as obtained from injection 1 using hardware B, uncoated, in accordance with an illustrative embodiment of the technology.
Figure 21H:
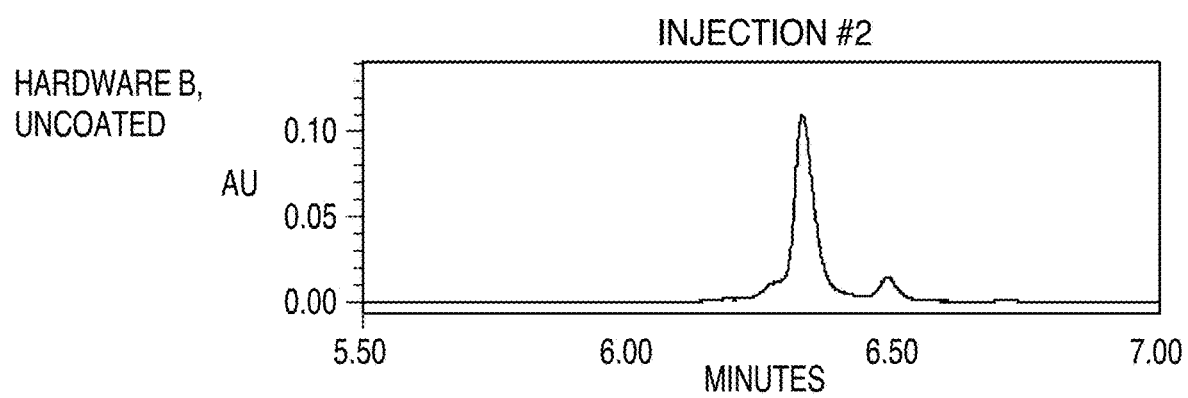
FIG. 21H is a chromatogram of NIST reference material 8671, an IgG1κ mAb, as obtained from injection 2 using hardware B, uncoated, in accordance with an illustrative embodiment of the technology.
Figure 21I:
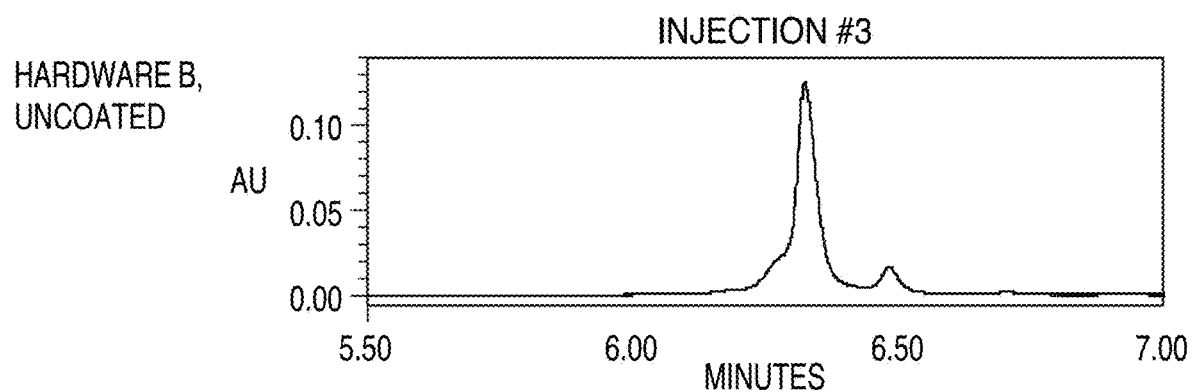
FIG. 21I is a chromatogram of NIST reference material 8671, an IgG1κ mAb, as obtained from injection 3 using hardware B, uncoated, in accordance with an illustrative embodiment of the technology.
Figure 21J:
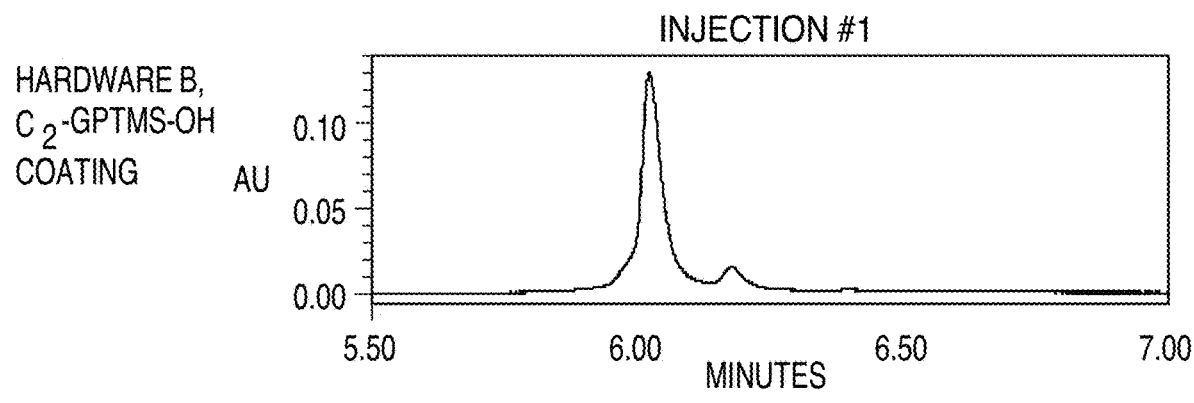
FIG. 21J is a chromatogram of NIST reference material 8671, an IgG1κ mAb, as obtained from injection 1 using hardware B, $C_2$-GPTMS-OH coating, in accordance with an illustrative embodiment of the technology.
Figure 21K:
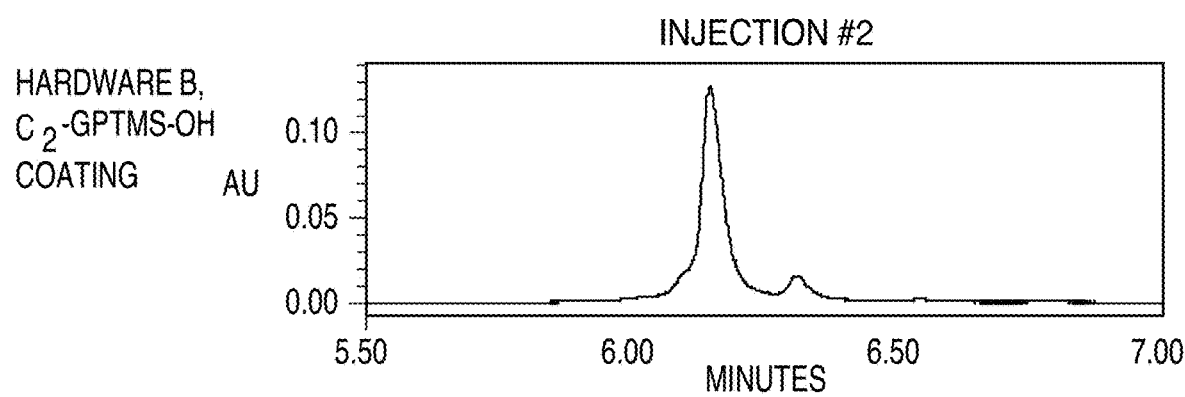
FIG. 21K is a chromatogram of NIST reference material 8671, an IgG1κ mAb, as obtained from injection 2 using hardware B, $C_2$-GPTMS-OH coating, in accordance with an illustrative embodiment of the technology.
Figure 21L:
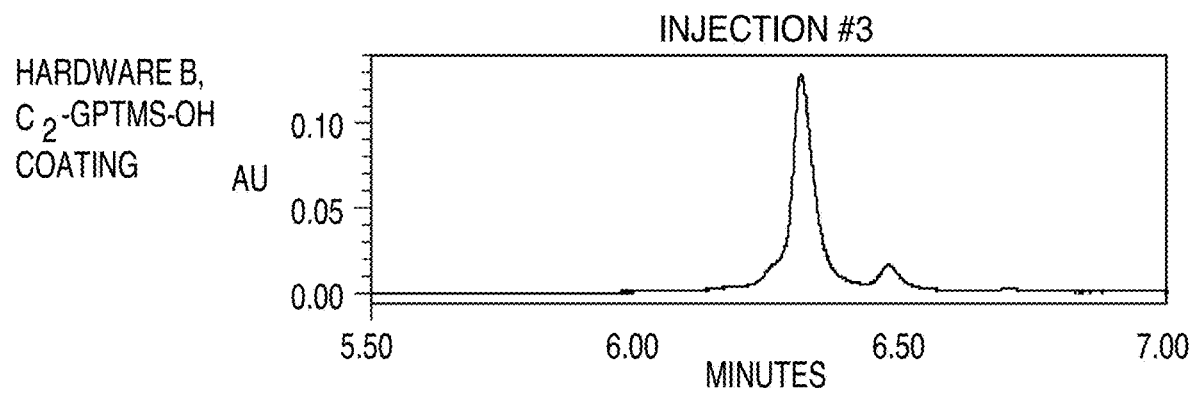
FIG. 21L is a chromatogram of NIST reference material 8671, an IgG1κ mAb, as obtained from injection 3 using hardware B, $C_2$-GPTMS-OH coating, in accordance with an illustrative embodiment of the technology.

ASTM G48 Method A is used to rank the relative pitting corrosion performance of various grades of stainless steel. It consists of placing a part in ~6% ferric chloride solution for 72 hours, and checking the mass loss of your component. The test can be run at room temperature, or at slightly elevated temperatures to increase the corrosion rate. The ferric chloride solution is similar to the environment inside a pit during "non-accelerated" pitting corrosion; an acidic, oxidizing, chloride containing environment. When an entire part of interest is submerged in the ferric chloride solution, pitting corrosion is greatly accelerated, with normal test times only being 72 hours. FIG. 20 displays the corrosion performance of a non-coated column tube, and various coatings on a column tube. The improvement ranges from ~10× to ~100×.

Example 5

HILIC-Fluorescence-MS of Phosphoglycans

A recombinant alpha-galactosidase was diluted to 2 mg/mL. A 7.5 uL aliquot of the protein solution was then added to a 1 mL reaction tube containing 15.3 μL of water and 6 μL of buffered 5% RapiGest SF solution-commercially available from Waters Corporation (Milford, Mass.) (50 mM HEPES-NaOH, pH 7.9). The mixture was placed in a heat block at 90° C. for 3 minutes. Thereafter, the reaction tube was allowed to cool at room temperature for 3 minutes. To the reaction tube, 1.2 μL of PNGase F was then added and incubated at 50° C. for 5 minutes. After incubation, the reaction was again allowed to cool at room temperature for 3 minutes. To a vial containing 9 mg of RapiFluor-MS reagent, 131 uL of anhydrous DMF was added and vortexed to create a labeling solution. A 12 uL volume of this labeling solution was next added to the reaction tube. This labeling reaction was allowed to proceed for 5 minutes to produce the final sample.

A fully porous amide HILIC stationary phase (1.7 um, 130 Å) was used in a 2.1×50 mm column dimension to chromatograph the samples at a flow rate of 0.4 mL/min and temperature of 60° C. The gradient flow conditions initiated with 75.0% organic solvent (Acetonitrile) and 25.0% aqueous eluent (50 mM ammonium formate, pH 4.4) followed by a 11.66 min linear gradient to 54.0% organic/46% aqueous eluent. The column was then cycled through an aqueous regeneration step at 100% aqueous mobile phase at a flow rate of 0.2 mL/min for one minute. After the aqueous regeneration, the column was equilibrated at initial conditions for 4 minutes. Species eluting during the above separations were detected serially via fluorescence (Ex 265/Em 425, 2 Hz) followed by online ESI-MS. Mass spectra were acquired with a Xevo G2-XS QToF mass spectrometer operating with a capillary voltage of 2.2 kV, source temperature of 120° C., desolvation temperature of 500° C., and sample cone voltage of 50 V. Mass spectra were acquired at a rate of 2 Hz with a resolution of approximately 40,000 over a range of 700-2000 m/z. FIGS. 4A-4C present comparisons of this HILIC separation of RapiFluor-MS labeled released N-glycans from a recombinant alpha-galactosidase as performed with columns constructed of varying coatings and materials. FIGS. 6A-6C present comparisons of this HILIC separation as performed with columns constructed of varying coatings and materials in conjunction with a sample needle and column inlet tubing constructed of varying coatings.

Example 6

RPLC-UV-MS of Phosphopeptides

A vial of phosphopeptide test standard (Waters Corporation, Milford, Mass.) was reconstituted with 50 uL of 0.1% formic acid. A fully porous CSH C18 stationary phase material (1.7 um, 130 Å) was used in 2.1×50 mm column dimensions to chromatograph the samples at a flow rate of 0.2 mL/min at a temperature of 60° C. The gradient flow conditions initiated with 0.7% organic mobile phase (0.075% formic acid in acetonitrile) and 99.3% aqueous mobile phase (0.1% formic acid) followed by a 30 min linear gradient to 50% organic/50% aqueous. Species eluting during the above separations were detected serially via UV (220 nm) followed by online ESI-MS. Mass spectra were acquired with a Xevo G2-XS QToF mass spectrometer operating with a capillary voltage of 1.5 kV, source temperature of 100° C., desolvation temperature of 350° C., and sample cone voltage of 50 V. Mass spectra were acquired at a rate of 2 Hz with a resolution of approximately 40,000 over a range of 500-6500 m/z. FIGS. 7A-7C present comparisons of this reversed phase separation of the phosphopeptide standard performed with columns constructed of varying coatings and materials.

Example 7

RPLC/MS of Small Biomolecules (Nucleotides and Sugar Phosphates)

RPLC/MS analyses of two nucleotides (adenosine monophosphate and adenosine triphosphate) and two sugar phosphates (glucose-6-phosphate and fructose-6-phosphate) were performed by reversed phase separations with an organosilica C18 stationary phase according to the methods parameters noted below. FIGS. 8-11 present comparisons of these reversed phase separations as performed with columns constructed of varying coatings and materials.
LC Conditions
Columns: BEH C18 130 Å 1.7 µm 2.1×100 mm
Mobile Phase A: 0.25% Octylamine in $H_2O$ pH adjusted to 9 with acetic acid
Mobile Phase B: ACN
Column Temperature: 35° C.
Injection Volume: 10 µL (100 ng/mL sample concentrations)
Sample Diluent: Water
Detection: Tandem quadrupole mass spectrometer operating in ESI negative ionization mode and with MRM acquisition.
Gradient Table:

| Time(min) | Flow Rate(mL/min) | % A | % B | Curve |
|---|---|---|---|---|
| Initial | 0.450 | 95 | 5 | Initial |
| 5 | 0.450 | 75 | 25 | 6 |
| 10 | 0.450 | 75 | 25 | 6 |
| 20 | 0.450 | 50 | 50 | 6 |
| 21 | 0.450 | 5 | 95 | 6 |
| 22 | 0.450 | 95 | 5 | 6 |
| 30 | 0.450 | 95 | 5 | 6 |

Example 8

LC-Fluorescence-MS of Highly Sialylated Glycans using Charge Surface Reversed Phase Chromatography RapiFluor-MS labeled N-glycans were prepared from bovine fetuin (Sigma F3004) according to a previously published protocol (Lauber, M. A.; Yu, Y. Q.; Brousmiche, D. W.; Hua, Z.; Koza, S. M.; Magnelli, P.; Guthrie, E.; Taron, C. H.; Fountain, K. J., Rapid Preparation of Released N-Glycans for HILIC Analysis Using a Labeling Reagent that Facilitates Sensitive Fluorescence and ESI-MS Detection. Anal Chem 2015, 87 (10), 5401-9). Analyses of these released glycans were performed using a Waters ACQUITY UPLC H-Class Bio LC system and a separation method based on a previously described charged surface reversed phase chromatographic material described in International Application No. PCT/US2017/028856, entitled "CHARGED SURFACE REVERSED PHASE CHROMATOGRAPHIC MATERIALS METHOD FOR ANALYSIS OF GLYCANS MODIFIED WITH AMPHIPATHIC, STRONGLY BASED MOIETIES" (and incorporated by reference). Specifically, RapiFluor-MS labeled glycans (e.g., glycans labeled with the labeling reagent discussed in PCT/US2017/028856 were separated according to a mixed mode separation using a fully porous (130 Å) 1.7 µm diethylaminopropyl high purity chromatographic material (DEAP HPCM) in a 2.1×100 mm column configuration. Details of the method are described below. FIGS. 12 and 13 present comparisons of this mixed mode separation of sialylated glycans as performed with columns constructed of varying coatings and materials.
LC Conditions
Column: DEAP HPCM 130 Å 1.7 µm 2.1×100 mm
Mobile Phase A: Water and 100 mM Formic Acid/100 mM Ammonium Formate in 60%
Mobile Phase B: 100 mM Formic Acid/100 mM Ammonium Formate in 60% ACN
Column Temperature: 60° C.
Injection Volume: 4 µL
Sample Concentration: 10 pmol/µL
Sample Diluent: Water
Fluorescence Detection: Ex 265 nm/Em 425 nm (10 Hz)
Gradient Table:

| Time(min) | Flow Rate(mL/min) | % A | % B | Curve |
|---|---|---|---|---|
| Initial | 0.400 | 100.0 | 0.00 | Initial |
| 24.00 | 0.400 | 78.0 | 22.0 | 6 |
| 24.20 | 0.400 | 0.0 | 100.0 | 6 |
| 24.40 | 0.400 | 0.0 | 100.0 | 6 |
| 24.60 | 0.400 | 100.0 | 0.0 | 6 |
| 30.00 | 0.400 | 100.0 | 0.0 | 6 |

Example 9

LC/MS of a Reduced, IdeS Digested Monoclonal Antibody (mAb)

Formulated NIST mAb Reference Material 8671 (an IgG1κ) was added to 100 units of IdeS and incubated for 30 minutes at 37° C. The resulting IdeS-digested mAb was then denatured and reduced by the addition of 1M TCEP and solid GuHCl. The final buffer composition for the denaturation/reduction step was approximately 6 M GuHCl, 80 mM TCEP, and 10 mM phosphate (pH 7.1). IdeS-digested NIST RM 8671 (1.5 mg/mL) was incubated in this buffer at 37° C. for 1 hour, prior to being stored at 4° C. Reversed phase (RP) separations of the reduced, IdeS-fragmented mAb were performed to demonstrate the effects of employing different vapor deposition coated column hardware pieces, namely the column tube and the frits that enclose the stationary phase into its packing.

A C4 bonded superficially porous stationary phase (2 µm, Rho 0.63, 290 Å) was used in a 2.1×50 mm column dimension to chromatograph the samples at a flow rate of 0.2 mL/min and temperature of 80° C. across a linear gradient consisting of a 20 min linear gradient from 15 to 55% organic mobile phase (aqueous mobile phase: 0.1% (v/v) formic acid in water; organic mobile phase: 0.1% (v/v) formic acid in acetonitrile). Species eluting during the above separations were detected serially via fluorescence (Ex 280/Em 320, 10 Hz) followed by online ESI-MS. Mass spectra were acquired with a Synapt G2-S mass spectrometer operating with a capillary voltage of 3.0 kV, source temperature of 150° C., desolvation temperature of 350° C., and sample cone voltage of 45 V. Mass spectra were acquired at a rate of 2 Hz with a resolution of approximately 20,000 over a range of 500-4000 m/z. FIGS. 14-17 present comparisons of this reversed phase C4 separation of reduced, IdeS-digested NIST Reference Material 8671 as performed with columns constructed of varying coatings and materials.

Example 10

Ion Exchange Chromatography

NIST mAb Reference Material 8671 (an IgG1κ) was separated using columns constructed from a 3 μm non-porous cation exchange stationary phase packed into either uncoated or vapor deposition coated hardware. Separations were performed with an ACQUITY UPLC H-Class Bio instrument according to the experimental conditions outlined below. FIGS. 21 and 22 present comparisons of these separations and their resulting data as obtained with columns constructed of varying coatings and materials.

LC Conditions

Columns: 3 μm non-porous cation exchange stationary phase in a 2.1×50 mm column dimension
Sample: NIST mAb Reference Material 8671 diluted to 2.5 mg/mL with 20 mM MES pH 6.0 buffer
Gradient: 20 mM MES pH 6.0, 10-200 mM NaCl in 7.5 min
Flow Rate: 0.2 mL/min
Column Temperature: 30° C.
Injection Volume: 1 μL (2.1 mm ID columns)
Detection: 280 nm
Hardware Design: Hardware A—Identical to ACQUITY UPLC BEH C18 column hardware
Hardware B—A design with an alternative sealing mechanism and some alternative material compositions.

Example 11

Oligonucleotide Ion Pair RPLC

Testing has shown that flow paths modified with the vapor deposition coatings of this invention are also helpful in improving oligonucleotide separations. Example 11 provides evidence of such as observed in the form of improved recoveries and more accurate profiling of a sample's composition, particularly with respect to the first chromatograms obtained with a column.

In this work, a mixture of 15, 20, 25, 30, 35 and 40-mer deoxythymidine was separated using columns constructed from a 1.7 μm organosilica 130 Å $C_{18}$ bonded stationary phase packed into either uncoated or vapor deposition coated hardware. Separations were performed with an ACQUITY UPLC H-Class Bio instrument according to the experimental conditions outlined below. FIGS. 23A-F and 24 present comparisons of these separations and their resulting data as obtained with columns constructed of varying coatings and materials.

LC Conditions

Columns: 1.7 μm organosilica 130 Å $C_{18}$ bonded stationary phase in a 2.1×50 mm column dimension
Sample: 15, 20, 25, 30, 35 and 40-mer deoxythymidine (0.5 pmol/μL)
Column Temperature: 60° C.
Flow Rate: 0.2 mL/min
Mobile Phase A: 400 mM HFIP, 15 mM TEA in water
Mobile Phase B: 400 mM HFIP, 15 mM TEA in methanol
Gradient: 18 to 28% B in 5 min
Injection volume: 10 μL
UV Detection: 260 nm

Example 12

RPLC of Citric and Malic Acid

It should also be pointed out that the benefits of this invention are not limited to only biomolecules or phosphorylated/phospho group containing analytes. In fact, numerous types of so-called "small molecules" can be seen to have their separations improved through the adoption of vapor deposition coated flow paths and column hardware. One notable class of small molecules corresponds to compounds having a carboxylic acid moiety. By their nature, these are ubiquitous compounds and some, like citric acid and malic acid, are important metabolites of living organisms, given that they are constituents of the Kreb's cycle.

Herein, we have investigated the effects of separating citric acid and malic acid with untreated versus vapor deposition coated columns. Citric acid and malic acid were analyzed by LC-MS with columns constructed from a 1.8 μm silica 100 Å $C_{18}$ bonded stationary phase packed into either uncoated or $C_2C_3$ vapor deposition coated hardware. Separations were performed with an ACQUITY UPLC I-Class PLUS instrument, and eluting analytes were detected with a Xevo TQ-S triple quadrupole mass spectrometer according to the experimental conditions outlined below. FIGS. 25A-D presents a comparison of these separations and their resulting data. It can be observed from these results that use of the vapor deposition coated column hardware led to improvements in recovery and peak shape and thus sizable increases in MS intensity. This is noteworthy as it highlights the fact that the vapor deposition coating can be used to facilitate the development of a more sensitive and more accurate quantitation assay of these and other chemically similar compounds, including but not limited to isocitric acid, α-ketoglutaric acid, succinic acid, fumaric acid, lactic acid, aconitic acid, itaconic acid, oxaloacetic acid, pyruvic acid, pantothenic acid, biotin, and folic acid. It is reasonable to assume that even zwitterionic small molecules would benefit from this invention. This class of compounds includes but is not limited to amino acids and neurotransmitters. Likewise, it is envisioned that this invention will be advantageous to be used to separate and analyze compounds containing metal binding moieties, such as cobalamin and the various types of porphyrins. Lastly, these same compounds would exhibit improved separations whether analyzed by RPLC or other modes of chromatography, such as hydrophilic interaction chromatography (HILIC), ion exchange, or mixed mode LC separations (i.e. ion exchange/reversed phase or ion exchange/HILIC).

LC Conditions

Columns: 1.8 μm silica 100 Å $C_{18}$ bonded stationary phase in a 2.1×50 mm column dimension
Sample: Citric acid
Malic acid
Column Temperature: 30° C.
Flow Rate: 0.5 mL/min
Mobile Phase A: 0.1% formic acid, water
Mobile Phase B: 0.1% formic acid, acetonitrile
Injection volume: 2 μL
Gradient Table:

| Time(min) | Flow Rate(mL/min) | % A | % B | Curve |
|---|---|---|---|---|
| Initial | 0.500 | 100.0 | 0.00 | Initial |
| 0.25 | 0.500 | 100.0 | 0.00 | 6 |
| 2.00 | 0.500 | 75.0 | 25.0 | 6 |

-continued

| Time(min) | Flow Rate(mL/min) | % A | % B | Curve |
|---|---|---|---|---|
| 2.50 | 0.500 | 5.0 | 95.0 | 6 |
| 3.00 | 0.500 | 5.0 | 5.0 | 6 |
| 3.10 | 0.500 | 100.0 | 0.0 | 6 |

MS Conditions
MS1 Resolution: 1 Da
MS2 Resolution: 0.75 Da
Capillary Voltage: 1 kV
Source Offset: 50
Desolvation Temp.: 600° C.
Desolvation Gas Flow: 1000 L/hr
Cone Gas: 150 L/hr
Nebulizer: 7 bar
Source Temp.: 150° C.
MRM (Citric Acid): 191.2>87.1
MRM (Malic Acid): 133.2>115.2

Example 13

Mixed Mode Chromatography of Pesticides

Glyphosate is non-selective broad spectrum herbicide which is widely used across the globe as a crop desiccant. Maximum residue limits (MRLs) are enforced globally on various commodities of interest because of the potential health consequences posed to consumers. Glyphosate and its metabolite aminomethylphosphonic acid (AMPA) require unique approaches for sample preparation and chromatography separation. Various methods can be employed for quantitation, whether they are based on reversed phase, porous graphitizes carbon, ion chromatography, hydrophilic interaction chromatography (HILIC) or mixed mode retention mechanisms. No matter the separation mode, assays for glyphosate and other related herbicide compounds can prove to be problematic. First, polar pesticides are difficult to retain on reversed phase columns without derivatization. Second, glyphosate interacts with active metal surfaces. As a result, it is notoriously observed in the form of a broad peak or one with pronounced tailing.

Herein, we have investigated the separation of glyphosate with untreated versus vapor deposition coated mixed mode HILIC columns. Glyphosate was analyzed by LC-MS with 1.7 µm diethylamine bonded organosilica 130 Å columns constructed from either uncoated or $C_2C_{10}$ vapor deposition coated stainless steel hardware. Separations were performed with an ACQUITY UPLC H-Class Bio coupled with a Xevo TQ-XS triple quadrupole mass spectrometer according to the experimental conditions outlined below.

FIGS. 26A-B and 27A-B show a comparison of coated and uncoated column performance for glyphosate in a solvent standard. As seen in FIG. 26B, glyphosate appears as a severely tailing, broad peak. In contrast, as seen in FIG. 26B, glyphosate is separated with much improved peak shape on the vapor deposition coated column. It can be observed from these results that the use of the vapor deposition coated column hardware led to significant improvements in peak shape, reduced peak widths and thus sizable increases in MS intensity (FIGS. 27A-B). It is reasonable to assume that the vapor deposition coated column also yielded higher recovery. These results are noteworthy as they demonstrate a means to developing more sensitive and more accurate quantitation assays for glyphosate and other chemically similar compounds, including but not limited to pesticides such as Ethephon, 2-Hydroxyethyl phosphonic acid (HEPA), Glufosinate-Ammonium, N-Acetyl-glufosinate, 3-Methylphosphinicopropionic acid (MPPA), Aminomethylphosphonic acid (AMPA), N-Acetyl-glyphosate, N-Acetyl-AMPA, Fosetyl-aluminium, Phosphonic acid, Maleic hydrazide, Perchlorate, and Chlorate.

LC Conditions
Columns: 1.7 µm diethylamine bonded organosilica 130 Å stationary phase in a 2.1×100 mm column dimension
Sample: Glyphosate
Column Temperature: 50° C.
Flow Rate: 0.5 mL/min
Mobile Phase A: 0.9% formic acid, water
Mobile Phase B: 0.9% formic acid, acetonitrile
Injection volume: 10 µL
Gradient Table:

| Time (min) | Flow Rate (mL/min) | % A | % B | Curve |
|---|---|---|---|---|
| Initial | 0.500 | 10 | 90 | Initial |
| 4.00 | 0.500 | 85 | 15 | 2 |
| 10.0 | 0.500 | 85 | 15 | 6 |
| 16.0 | 0.500 | 10 | 90 | 1 |
| 20.0 | 0.500 | 10 | 90 | 1 |

MS Conditions
MS1 Resolution: 1 Da
MS2 Resolution: 0.75 Da
Capillary Voltage: 2.4 kV
Ionization: ESI−
Desolvation Temp.: 600° C.
Desolvation Gas Flow: 1000 L/hr
Cone Gas: 150 L/hr
Nebulizer: 7 bar
Source Temp.: 150° C.
MRM 1: 168.0>62.6
MRM 2: 168.0>149.8

Example 14

Minimizing Adsorptive Losses of Antibodies in Sample Preparation

Immunoglobulin G (IgG) is the most common antibody found within blood circulation. Diagnostic testing of patient's blood samples analyzes the concentration of IgG to detect the possibility of certain diseases, infection, or cancer possibility. As a result, losses of IgG to labware and sample preparation devices can impact or have a negative effect on the results.

One piece of labware that is very frequently used to manipulate samples is the disposable pipette tip. While commonly used to aspirate, measure, transfer and dispense liquids, a pipette tip can also be used as a housing for solid phase extraction media or affinity resin. Most pipette tips are made of polypropylene, as this material exhibits chemical resistance to common acids, bases and organic solvents. However, the hydrophobicity of polypropylene is known to cause high levels of adsorptive losses when used with biological analytes, like proteins and peptides. Similarly, frits used to secure solid phase extraction media or affinity resin within a housing is also commonly made from polypropylene or polyethylene (another known material that causes adsorptive losses).

Herein, we have investigated the adsorptive losses with untreated versus vapor deposition coated fritted disposable pipette tips. To address adsorptive losses, the wetted surfaces of fritted pipette tips were modified with a $C_2$-GPTMS-OH coating (See Example 2 above). The coating was applied using vapor deposition through the interior of fritted pipette. That is, the wetted surfaces of the pipette tips were coated with C$_2$-GPTMS-OH with the frits installed within the devices; the vapors infiltrating into the pipette and coating walls and the frit along the fluidic path. Tests were performed on the C$_2$-GPTMS-OH coated tips (in two sizes 200 μL and 1000 μL), and compared to plasma treated devices, and untreated devices.

The adsorptive losses resulting in the C$_2$-GPTMS-OH coated tips, the plasma-treated (oxygen plasma with water vapor), and untreated tips were measured by passing 20 μg of rabbit IgG (rIgG, Equitech-Bio, SLR56) through each tip for 5 aspiration/dispensing cycles with a multi-channel pipette. The flow-through fraction was collected to determine the amount of IgG recovered from each tip. The concentration of rig in each fraction was measured using a fluorometer (Gemini XPS, Molecular Devices). The amount of igG lost during the sample preparation was calculated by comparing the amount of rIgG loaded versus the amount of IgG recovered in the flow-through.

In this comparative test, 200 μL of 0.1 mg/mL IgG solution was applied to the 200 μL injection-molded tips (in coated, plasma-treated, and untreated formats) and 1 mL of 0.02 mg/mL of IgG solution was applied to the 1000 μL tips. The rIgG solutions were first transferred to a 96-well plastic plate (commercially available from Waters Corporation, Milford, Mass.) using either 200 μL or 1000 μL untreated polypropylene pipette tips, then loaded to the test tips. Six replicates were tested for the coated and plasma treated tips and four replicates were tested for the untreated tips.

FIGS. 28A-B show a comparison of recovery and adsorptive losses of coated, plasma-treated, and uncoated/untreated fritted pipette tips. These graphs indicated that the adsorptive loss of rIgG to the fritted pipette tip decreased dramatically with the application of the alkylsilyl coating. Comparing the results for the 200 μL format, the C$_2$-GPTMS-OH coating appeared to eliminate the loss of approximately 2.7 μg of rIgG. A similar result was observed with the 1000 μL fritted tips. Somewhat surprisingly, the plasma-treated tip appeared to cause adsorptive losses comparable to that of the untreated tip. Thus, it appears that the application of a vapor deposition coating to pieces of labware is an effective approach to minimizing adsorptive analyte losses during sample preparations (and or other processing). It is noted that any background sample loss can be attributed to the use of untreated polypropylene vessels to transfer the samples to untreated well plates. While this example demonstrates the utility of this approach for improving the recovery of a biological analyte, it need not be limited to any singular class of molecules. Benefits are likely to be found in the preparation of both small and large molecules derived from both synthetic and biological origins.

Alternatives:

There are a number of alternative methods and uses for the present technology. While the above methods have generally been discussed with respect to chromatography, the use of a column, or labware, such as beakers, pipettes, and extraction devices, other types of fluid components having an internal flow path may benefit from the present technology. For example, it is generally thought that capillary electrophoresis, such as capillary zone electrophoresis, exhibits relatively poor reproducibility. Much of the reproducibility issues can be reasoned to originate from irreproducible surface chemistry on the inner diameter of the tubular capillaries that are used to perform the separation. A vapor deposition coating on capillaries intended for a CE separation may therefore circumvent reproducibility issues as it can yield an inordinately thick, rugged coating. The inventions described herein may consequently be applicable to improving CE separations of both small and large biomolecules.

Moreover, while many of the examples of the described aspects employ comparatively hydrophobic coatings, with water contact angles ranging from 50° to 115°, it is reasonable to suggest that some separations could be enhanced through the application of hydrophilic or other types of coatings, including but not restricted to diol, ethers, esters, amide/ureido type, and polyethylene oxide/glycol bondings and, in some embodiments, coatings having contact angles between 0.1 to about 60°.

Other analytes, not yet explicitly described, may also benefit from vapor deposition coated chromatographic flow paths, for instance phosphorothioated oligonucleotides. Nucleic acids inherently contain repeating phosphodiester bonds as part of their backbone. In some case, the phosphodiester backbone is replaced in part with a phosphorothioate backbone, which can impart in itself unique challenges for a separation. Similarly, intact and proteolytically digested antibody conjugates may benefit from methods entailing the use of vapor deposition chromatographic flow paths. Lastly, biomolecules containing histidine residues are likely to benefit from this invention as, like phosphorylated and carboxylate containing residues, they have a propensity for binding to metal.

What is claimed is:

1. A sample preparation device comprising wetted surfaces defining a fluidic path extending within an interior of the sample preparation device,
   wherein a material forming the wetted surfaces of the fluidic path prior to coating is formed of a polymeric material, and
   wherein at least a portion of the wetted surfaces of the fluidic path are coated with an alkylsilyl coating having Formula I:

wherein
   $R^1$, $R^2$, $R^3$, $R^4$, $R^5$, and $R^6$ are each independently selected from (C$_1$-C$_6$)alkoxy, —NH(C$_1$-C$_6$)alkyl, —N((C$_1$-C$_6$)alkyl)$_2$, OH, OR$^A$, and halo;
   $R^A$ represents a point of attachment to the fluidic path; at least one of $R^1$, $R^2$, $R^3$, $R^4$, $R^5$, and $R^6$ is OR$^A$; and
   X is (C$_1$-C$_{20}$)alkyl, —O[(CH$_2$)$_2$O]$_{1-20}$—, —(C$_1$-C$_{10}$)[NH(CO)NH(C$_1$-C$_{10}$)]$_{1-20}$—, or —(C$_1$-C$_{10}$)[alkylphenyl (C$_1$-C$_{10}$)alkyl]$_{1-20}$-.

2. The sample preparation device of claim 1, wherein the polymeric material comprises polyether ether ketone, polypropylene, or polyethylene.

3. The sample preparation device of claim 1, wherein the alkylsilyl coating has a contact angle of at least 15°.

4. The sample preparation device of claim 3, wherein the alkylsilyl coating has a contact angle of less than or equal to 60°.

5. The sample preparation device of claim 1, wherein the alkylsilyl coating has a thickness of at least 100 Å.

6. The sample preparation device of claim 1, wherein the alkylsilyl coating of Formula I is bis(trichlorosilyl)ethane or bis(trimethoxysilyl)ethane.

7. The sample preparation device of claim 1, further comprising a second alkylsilyl coating in direct contact with the alkylsilyl coating of Formula I, the second alkylsilyl coating having Formula II:

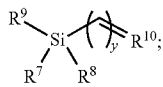
(II)

wherein

R$^7$, R$^8$, and R$^9$ are each independently selected from —NH(C$_1$-C$_6$)alkyl, —N[(C$_1$-C$_6$)alkyl]$_2$, (C$_1$-C$_6$) alkoxy, (C$_1$-C$_6$)alkyl, (C$_1$-C$_6$)alkenyl, OH, and halo;

R$^{10}$ is selected from (C$_1$-C$_6$)alkyl, —OR$^B$, —[O(C$_1$-C$_3$) alkyl]$_{1-10}$O(C$_1$-C$_6$)alkyl, —[O(C$_1$-C$_3$)alkyl]$_{1-10}$OH and phenyl, wherein said (C$_1$-C$_6$)alkyl is optionally substituted with one or more halo and wherein said phenyl is optionally substituted with one or more groups selected from (C$_1$-C$_3$)alkyl, hydroxyl, fluorine, chlorine, bromine, cyano, —C(O)NH$_2$, and carboxyl;

R$^B$ is —(C$_1$-C$_3$)alkyloxirane, —(C$_1$-C$_3$)alkyl-3,4-epoxycyclohexyl, or —(C$_1$-C$_4$)alkylOH;

the hashed bond to R$^{10}$ represents an optional additional covalent bond between R$^{10}$ and the carbon bridging the silyl group to form an alkene, provided y is not 0; and y is an integer from 0 to 20.

8. The sample preparation device of claim 7, wherein the alkylsilyl coating of Formula II is (3-glycidyloxypropyl) trimethoxysilane, n-decyltrichlorosilane, trimethylchlorosilane, trimethyldimethylaminosilane, methoxy-polyethyleneoxy(1-10) propyl trichlorosilane, or methoxy-polyethyleneoxy(1-10) propyl trimethoxysilane.

9. The sample preparation device of claim 8, wherein the alkylsilyl coating of Formula II is (3-glycidyloxypropyl) trimethoxysilane followed by hydrolysis.

10. The sample preparation device of claim 7, wherein the alkylsilyl coating of Formula I and II provides a desired contact angle of about 5° to about 60°.

11. The sample preparation device of claim 7, wherein the alkylsilyl coating of Formula I is bis(trichlorosilyl)ethane or bis(trimethoxysilyl)ethane and the alkylsilyl coating of Formula II is (3-glycidyloxypropyl)trimethoxysilane.

12. The sample preparation device of claim 7, wherein the alkylsilyl coating of Formula I is bis(trichlorosilyl)ethane or bis(trimethoxysilyl)ethane and the alkylsilyl coating of Formula II is (3-glycidyloxypropyl)trimethoxysilane followed by hydrolysis.

13. The sample preparation device of claim 2, wherein the wetted surfaces prior to coating include two or more different polymeric materials.

* * * * *